United States Patent
Shim et al.

(10) Patent No.: US 12,399,294 B1
(45) Date of Patent: Aug. 26, 2025

(54) PROJECTED DIELECTRIC SENSOR FOR MATTER DETECTION, PROXIMITY DETECTION, AND GESTURE CONTROL

(71) Applicant: Studio 1 Labs Inc., Markham (CA)

(72) Inventors: Edward Sup Shim, Toronto (CA); Marouane El Kamel, Drancy (FR)

(73) Assignee: Studio 1 Labs Inc., Markham (CA)

( * ) Notice: Subject to any disclaimer, the term of this patent is extended or adjusted under 35 U.S.C. 154(b) by 0 days.

(21) Appl. No.: 18/894,876

(22) Filed: Sep. 24, 2024

(51) Int. Cl.
| | |
|---|---|
| *G01V 3/08* | (2006.01) |
| *A61B 5/00* | (2006.01) |
| *G01R 27/26* | (2006.01) |
| *G06F 3/01* | (2006.01) |
| *G06F 3/044* | (2006.01) |

(52) U.S. Cl.
CPC ............ *G01V 3/088* (2013.01); *A61B 5/6802* (2013.01); *G01R 27/2617* (2013.01); *G06F 3/017* (2013.01); *G06F 3/0445* (2019.05); *G06F 2203/04112* (2013.01)

(58) Field of Classification Search
CPC ....... G01V 3/088; G06F 3/0445; G06F 3/017; G06F 2203/04112; A61B 5/6802; G01R 27/2617
See application file for complete search history.

(56) References Cited

U.S. PATENT DOCUMENTS

| | | | |
|---|---|---|---|
| 5,878,620 A | 3/1999 | Gilbert | |
| 7,395,717 B2 | 7/2008 | DeAngelis | |
| 7,500,536 B2 | 3/2009 | Bulgajewski | |
| 8,599,165 B2 * | 12/2013 | Westhues | G06F 3/0446 345/87 |
| 8,711,105 B2 * | 4/2014 | Gray | G06F 3/0445 345/173 |
| 8,711,121 B2 * | 4/2014 | Gray | G06F 3/0446 345/173 |
| 8,991,917 B2 | 3/2015 | Kato | |
| 9,266,454 B2 | 2/2016 | Barfuss | |
| 9,511,732 B2 | 12/2016 | Dolcetti | |

(Continued)

FOREIGN PATENT DOCUMENTS

| | | | | |
|---|---|---|---|---|
| CN | 107847164 A | * | 3/2018 | ......... A61B 5/02141 |
| CN | 113785179 A | * | 12/2021 | ............ G01M 3/165 |

(Continued)

*Primary Examiner* — Octavia Hollington
(74) *Attorney, Agent, or Firm* — Smart & Biggar LP

(57) ABSTRACT

Systems and methods for a projected dielectric sensor comprising a first conductive path with a first conductive mesh, a second conductive path with a second conductive mesh, and a dielectric gap between them. The dielectric gap functions as an open circuit in a resting state, offering a broader detection range compared to traditional sensors. The sensor includes a power drive connected to the first conductive path and a collector connected to the second conductive path. The first and second conductive meshes include sheets that are positioned longitudinally side-by-side, enhancing sensitivity and simplifying manufacturing. In an example, the sheets are separated by at least 10 cm of dielectric material. The sensor can detect off-axis objects such as conductors, vehicles, humans, and baby seats, making it suitable for various applications including vehicle safety, biometric systems, gesture and mid-air control, and machine learning integration.

28 Claims, 32 Drawing Sheets

(56) References Cited

U.S. PATENT DOCUMENTS

| | | | |
|---|---|---|---|
| 9,519,361 B2* | 12/2016 | Harley | G06F 3/0442 |
| 9,791,494 B2 | 10/2017 | Deumal Herraiz | |
| 10,019,110 B2* | 7/2018 | Weaver | G06F 3/041 |
| 10,076,982 B2 | 9/2018 | Barfuss | |
| 10,124,758 B2 | 11/2018 | Lamesch | |
| 10,126,149 B2 | 11/2018 | Virnich | |
| 10,330,813 B2 | 6/2019 | Wilson | |
| 10,386,224 B2* | 8/2019 | Shim | G01L 1/205 |
| 10,386,976 B2* | 8/2019 | Peng | G06F 3/0443 |
| 10,457,164 B2 | 10/2019 | Moenkemueller | |
| 10,627,957 B2* | 4/2020 | Khazeni | G06F 3/0443 |
| 10,670,448 B2 | 6/2020 | Aina | |
| 10,696,186 B2 | 6/2020 | Wilson | |
| 10,765,334 B2 | 9/2020 | Sugiyama | |
| 10,836,401 B1 | 11/2020 | Christensen | |
| 10,863,913 B2 | 12/2020 | Sugiyama | |
| 10,926,662 B2 | 2/2021 | Maguire | |
| 10,946,769 B2 | 3/2021 | Althaus | |
| 11,130,424 B2 | 9/2021 | Salter | |
| 11,133,800 B2 | 9/2021 | Salter | |
| 11,162,858 B2 | 11/2021 | Wettels | |
| 11,214,172 B2 | 1/2022 | Althaus | |
| 11,250,685 B2 | 2/2022 | Taylor | |
| 11,314,355 B2* | 4/2022 | Wilkinson | G06F 3/0443 |
| 11,565,626 B2 | 1/2023 | Cech | |
| 11,718,255 B2 | 8/2023 | Dias Da Cruz | |
| 11,719,557 B2 | 8/2023 | Wilson | |
| 11,787,311 B2 | 10/2023 | Wilson | |
| 2016/0364078 A1* | 12/2016 | Krah | G06F 3/0446 |
| 2017/0361744 A1 | 12/2017 | Persson | |
| 2018/0319365 A1 | 11/2018 | Derieux | |
| 2021/0086721 A1 | 3/2021 | Carraro | |
| 2021/0213853 A1 | 7/2021 | Balde | |
| 2023/0215615 A1* | 7/2023 | Lekas | H01L 23/492 |
| 2023/0238377 A1* | 7/2023 | Price | H01L 28/20 |
| | | | 257/379 |

FOREIGN PATENT DOCUMENTS

| | | | |
|---|---|---|---|
| KR | 20160105947 A * | 9/2016 | |
| WO | 2022181440 A1 | 9/2022 | |
| WO | 2022218886 A1 | 10/2022 | |

* cited by examiner

PROJECTED DIELECTRIC SENSOR FOR MATTER DETECTION, PROXIMITY DETECTION, AND GESTURE CONTROL

CROSS-REFERENCE

None.

TECHNICAL FIELD

Example embodiments relate to the field of sensor technology, for example to projected dielectric sensors used for detecting physical phenomena.

BACKGROUND

Dielectric sensors have become increasingly important in various fields, including automotive safety, biometric systems, and gesture control interfaces. The ability to detect matter such as conductors, other vehicles, humans, and baby seats, is desired in sensor technology.

SUMMARY

Example embodiments relate to dielectric sensor technology, for example to dielectric sensors used for detecting physical phenomena. These sensors are applicable in various fields such as automotive safety, biometric systems, gesture and/or mid-air control interfaces, human machine interface and machine learning systems, smart home technologies, industrial automation, and healthcare monitoring devices. Some example embodiments may relate to the field of variable pressure sensors and functional textile and, for example, to conductive apparatus and systems for detecting external force.

Examples of the dielectric sensor can address limitations of conventional sensors, particularly in applications requiring wide-area detection and precise spatial awareness.

Example embodiments relate to systems and methods involving projected dielectric sensors. These sensors utilize configurations of conductive paths and dielectric gaps to provide enhanced detection capabilities. Unlike traditional capacitive sensors, which arrange conductive paths on a Y-plane (transverse plane), or require a dielectric medium with a consistent resistance such as a resistor, as a reference baseline measurement, at least some examples of the projected dielectric sensor positions its conductive paths on the same X-plane (longitudinal plane). This arrangement allows for improved sensitivity and a broader detection range.

In an example, the dielectric gap in the projected dielectric sensor is an open circuit when in a resting state, over some conventional methods that would otherwise create a continuous circuit through the dielectric medium. This feature, combined with the large size of the gap compared to traditional sensors, can enhance the sensor's ability to detect changes in the environment over a broader range.

An example embodiment is a dielectric sensor, comprising: a first conductive path including a first conductive mesh, the first conductive mesh including a first sheet; a second conductive path including a second conductive mesh, the second conductive mesh including a second sheet, which are generally co-planar; a dielectric gap formed of matter which physically separates the first conductive path and the second conductive path, wherein the dielectric gap longitudinally separates the first sheet from the second sheet; and a collector connected to the second conductive path.

Another example embodiment is a dielectric sensor comprising: a first conductive path including a first conductive mesh, the first conductive mesh including a first sheet; a second conductive path including a second conductive mesh, the second conductive mesh including a second sheet; a dielectric gap formed of matter which physically separates the first conductive path and the second conductive path, wherein the first sheet and the second sheet are separated by at least 10 cm by the dielectric gap; and a collector connected to the second conductive path.

Some embodiments include a sensor capable of detecting a conductor or matter that is off-axis to the dielectric gap. Some embodiments include a sensor capable of detecting a second vehicle that is off-axis to the dielectric gap. Some embodiments include a sensor capable of detecting a human that is off-axis to the dielectric gap. Some embodiments include a sensor capable of detecting a baby seat that is off-axis to the dielectric gap.

Some embodiments include a sensor used in vehicle applications to detect the presence and position of occupants. Some embodiments include a sensor used in biometric applications for shape detection. Some embodiments include a sensor used in biometric applications for proximity detection.

Some embodiments include a sensor used in gesture and mid-air control interfaces. Some embodiments include a sensor used in human machine interface and machine learning systems. Some embodiments include a sensor used for social interaction in public spaces. Some embodiments include a sensor used in smart home systems for managing lighting. Some embodiments include a sensor used in smart home systems for climate control. Some embodiments include a sensor used in smart home systems for security.

Some embodiments include a sensor embedded in medical devices for monitoring vital signs. Some embodiments include a sensor used in industrial automation for detecting the position and orientation of components. Some embodiments include a sensor used in quality control to identify defects and inconsistencies in products. Some embodiments include a sensor integrated into flexible and wearable materials for continuous monitoring of physical activity, health metrics, and environmental conditions. Some embodiments include a sensor integrated into exterior vehicle bumpers for proximity detection. Some embodiments include a sensor facilitating gesture and mid-air control for interior vehicle settings such as temperature, audio, and navigation.

BRIEF DESCRIPTION OF THE DRAWINGS

A detailed description of the example embodiments is provided herein below by way of example only and with reference to the following drawings, in which.

Similar reference numerals may be used in different figures to denote similar components.

DETAILED DESCRIPTION OF EXEMPLARY EMBODIMENTS

Figure 1:
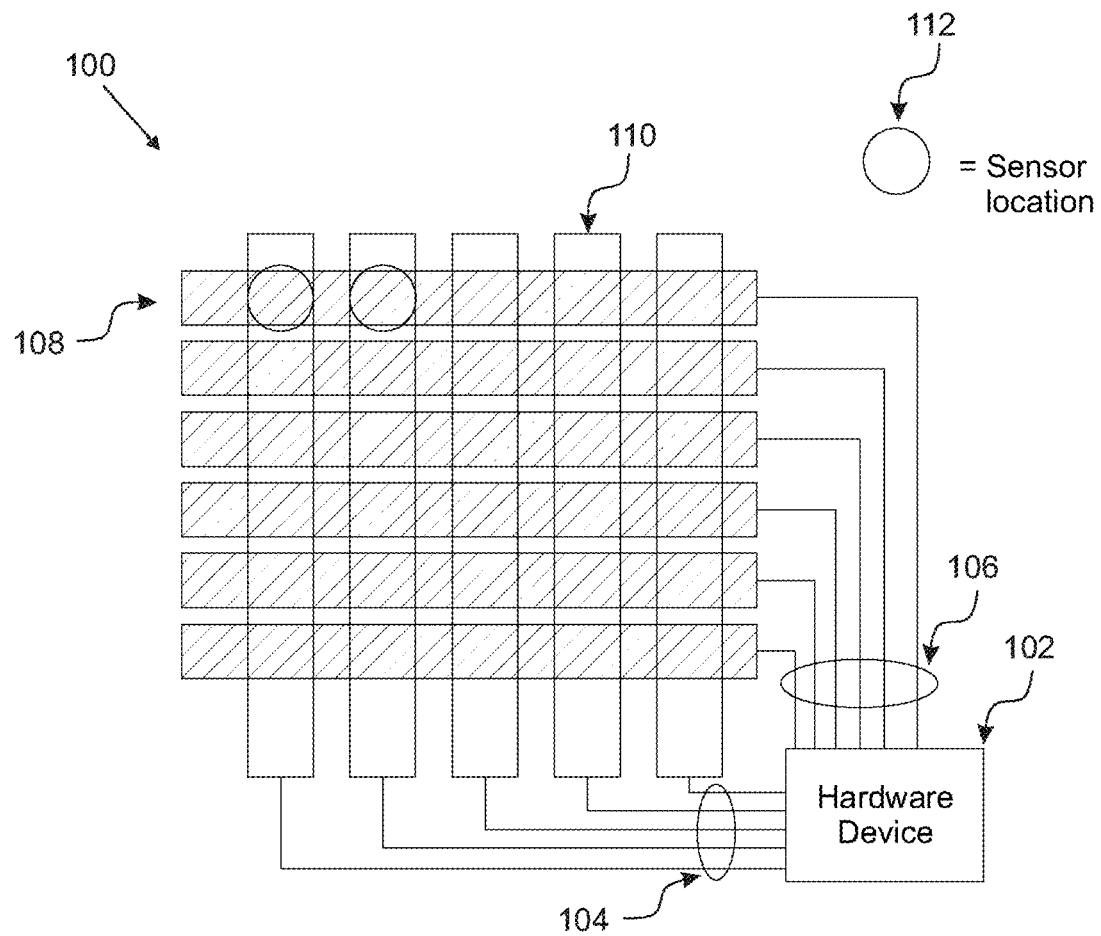
FIG. 1 shows an example pattern of overlapping first and second conductive paths for an embodiment of a flexible conductive apparatus, forming sensor areas at each intersecting points.

The figures are described below. Before the embodiments are to be explained in detail, it is to be understood that the presently disclosed subject matter is not limited in application or process to the details stated, as there are other embodiments and methods of carrying out and practicing the presently disclosed subject matter than those described. As such, the language used below is not limiting and states what may be used but may not necessarily be completely exhaustive.

Throughout the specification, wherever practicable, like structures will be identified with reference numbers. In some figures, components, such as additional electrical connections or fasteners have been omitted for clarity in the drawings. Unless expressly stated otherwise, the term "or" means "either or both" such that "A or B" includes A alone, B alone, and both A and B together.

Although the example embodiments of methods and systems will be described in terms of various examples, it is to be understood that such methods and systems are not intended to be limiting. Various alterations and modifications will be readily apparent to those of skill in the art. Accordingly, it is intended that the appended claims be interpreted as covering all alterations and modifications that fall within the spirit and scope of the example embodiments.

An example embodiment is a dielectric sensor, comprising: a first conductive path including a first conductive mesh, the first conductive mesh including a first sheet; a second conductive path including a second conductive mesh, the second conductive mesh including a second sheet, which are generally co-planar; a dielectric gap formed of matter which physically separates the first conductive path and the second conductive path, wherein the dielectric gap longitudinally separates the first sheet from the second sheet; and a collector connected to the second conductive path.

In another example embodiment of the dielectric sensor of any of the above, the dielectric gap does not constitute a vacuum.

In another example embodiment of the dielectric sensor of any of the above, air occupies the dielectric gap.

In another example embodiment of the dielectric sensor of any of the above, the dielectric sensor further includes fabric, foam, or other materials with physical form flexibility disposed within the dielectric gap.

In another example embodiment of the dielectric sensor of any of the above, the first conductive mesh and the second conductive mesh are each made of conductive fabric.

In another example embodiment of the dielectric sensor of any of the above, the first conductive mesh and the second conductive mesh are each made of conductive tape.

In another example embodiment of the dielectric sensor of any of the above, the first conductive mesh and the second conductive mesh are each made of conductive liquid.

In another example embodiment of the dielectric sensor of any of the above, the first conductive mesh and the second conductive mesh are each made of conductive metal.

In another example embodiment of the dielectric sensor of any of the above, the first sheet and the second sheet are generally coplanar.

In another example embodiment of the dielectric sensor of any of the above, the dielectric gap is at least 10 cm between the first sheet and the second sheet.

In another example embodiment of the dielectric sensor of any of the above, the first sheet and the second sheet are separated by at least 20 centimeters, 50 centimeters, 1 meter, 2 meters, 3 meters, 4 meters, or 5 meters.

In another example embodiment of the dielectric sensor of any of the above, the dielectric sensor further comprises a power drive connected to the first conductive path.

In another example embodiment of the dielectric sensor of any of the above, the first conductive path terminates at the first sheet and the second conductive path terminates at the second sheet.

In another example embodiment of the dielectric sensor of any of the above, the dielectric sensor is configured to detect a conductor or second matter that is off-axis to the dielectric gap.

In another example embodiment of the dielectric sensor of any of the above, the dielectric gap is an open circuit of the dielectric sensor in the absence of second matter at the dielectric gap.

In another example embodiment of the dielectric sensor of any of the above, the dielectric sensor is configured to detect a vehicle or a human that is off-axis to the dielectric gap.

In another example embodiment of the dielectric sensor of any of the above, the dielectric sensor is in at least one vehicle to detect presence and/or position of at least one occupant.

In another example embodiment of the dielectric sensor of any of the above, the dielectric sensor is integrated into at least one exterior vehicle bumper for proximity detection.

In another example embodiment of the dielectric sensor of any of the above, the dielectric sensor is used for shape detection in at least one biometric application.

In another example embodiment of the dielectric sensor of any of the above, the dielectric sensor is used for proximity detection in at least one biometric application.

In another example embodiment of the dielectric sensor of any of the above, the dielectric sensor is configured to interface with at least one gesture or mid-air control interface.

In another example embodiment of the dielectric sensor of any of the above, the at least one gesture or mid-air control interface is configured to manage mobility and interactivity with a vehicle.

In another example embodiment of the dielectric sensor of any of the above, the dielectric sensor is integrated in a medical device configured for monitoring at least one vital sign, the vital sign being one of heart rate, blood pressure, respiratory rate, body temperature, oxygen saturation (SpO2), electrocardiogram (ECG) signals, blood glucose levels, heart rate variability (HRV), end-tidal CO2 (ETCO2), respiratory effort, airflow, cardiac output, blood volume, hematocrit levels, skin conductance, galvanic skin response, intracranial pressure (ICP), arterial stiffness, or pulse wave velocity (PWV).

In another example embodiment of the dielectric sensor of any of the above, the dielectric sensor is integrated into at least one flexible and wearable material for continuous monitoring of at least one of physical activity, health metrics, or environmental conditions.

In another example embodiment of the dielectric sensor of any of the above, the dielectric sensor is a projected dielectric sensor.

In another example embodiment of the dielectric sensor of any of the above, the dielectric gap is an open circuit of the dielectric sensor when in a resting state.

In another example embodiment of the dielectric sensor of any of the above, the first sheet is shaped in a first pillar and the second sheet is shaped in a second pillar.

In another example embodiment of the dielectric sensor of any of the above, is integrated into a human machine interface and machine learning system.

Another example embodiment is a dielectric sensor comprising: a first conductive path including a first conductive mesh, the first conductive mesh including a first sheet; a second conductive path including a second conductive mesh, the second conductive mesh including a second sheet; a dielectric gap formed of matter which physically separates the first conductive path and the second conductive path, wherein the first sheet and the second sheet are separated by at least 10 cm by the dielectric gap; and a collector connected to the second conductive path.

In another example embodiment of the dielectric sensor of any of the above, the dielectric gap longitudinally separates the first sheet from the second sheet.

In another example embodiment of the dielectric sensor of any of the above, the first sheet and the second sheet are generally coplanar.

In another example embodiment of the dielectric sensor of any of the above, the first sheet and the second sheet are separated by at least 20 centimeters, 50 centimeters, 1 meter, 2 meters, 3 meters, 4 meters, or 5 meters.

In another example embodiment of the dielectric sensor of any of the above, the dielectric sensor is configured to detect a conductor or second matter that is off-axis to the dielectric gap.

In another example embodiment of the dielectric sensor of any of the above, the first sheet is shaped in a first pillar and the second sheet is shaped in a second pillar.

Exemplary embodiments are intended to cover all software or computer programs capable of performing the various heretofore-disclosed determinations, calculations, etc., for the disclosed purposes. For example, exemplary embodiments are intended to cover all software or computer programs capable of enabling processors to implement the disclosed processes. In other words, exemplary embodiments are intended to cover all systems and processes that configure a document operating system to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed above.

In accordance with the exemplary embodiments, the example computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The example computer programs can be written in exemplary programming languages that execute from memory on the device or from a hosted server, such as BASIC, COBOL, C, C++, Java, Pascal, or scripting languages such as JavaScript, Python, Ruby, PHP, Perl or other sufficient programming languages.

Some of the example embodiments include or otherwise involve data transfer over a network, such as communicating various inputs over the network. The network may include, for example, one or more of the Internet, Wide Area Networks (WANs), Local Area Networks (LANs), analog or digital wired and wireless telephone networks (e.g., a PSTN, Integrated Services Digital Network (ISDN), fiber, a cellular network, and Digital Subscriber Line (xDSL)), radio, television, cable, satellite, and/or any other delivery or tunneling mechanism for carrying data. Network may include multiple networks or subnetworks, each of which may include, for example, a wired or wireless data pathway. The network may include a circuit-switched voice network, a packet-switched data network, or any other network able to carry electronic communications. For example, the network may include networks based on the Internet protocol (IP) or asynchronous transfer mode (ATM), and may support voice using, for example, VoIP, Voice-over-ATM, or other comparable protocols used for voice data communications. In one implementation, the network includes a cellular telephone network configured to enable exchange of text or SMS messages.

Examples of a network include, but are not limited to, a personal area network (PAN), a storage area network (SAN), a home area network (HAN), a campus area network (CAN), a local area network (LAN), a wide area network (WAN), a metropolitan area network (MAN), a virtual private network (VPN), an enterprise private network (EPN), Internet, a global area network (GAN), Cel-Fi™, and so forth. Example embodiments may also include the use of networks such as LoRaWAN™, Wi-SUN™™, EnOcean™, Io-homecontrol™, ONE-NET, INSTEON™, Z-Wave™, or other Sub-GHz standards-based solutions.

The client and server devices are intended to include or otherwise cover all software or computer programs capable of performing the various heretofore-disclosed determinations, calculations, etc., for the disclosed purposes. For example, exemplary embodiments are intended to cover all software or computer programs capable of enabling processors to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed above.

In this specification, the term "force" and "pressure" are referring to the same notion of an intentional and unintentional interaction with an apparatus, and may be used interchangeably as applicable.

Sensors and switches have been used to understand information with regards to surrounding environments, or to control the outcome of an intended task. More information provides greater understanding, which normally results in greater amounts of sensors being added to increase understanding of further information at a higher degree. The basic fundamentals of electronic sensors are devices that determines electrical signals that are transformed into meaningful output that is used for a specific purpose or outcome. An example embodiment is a flexible conductive apparatus and systems for detecting pressure.

As individual sensors each require a minimum of two electrical connections in order to function, increasing the amount of sensors would result in doubling the amount of electrical connections for each additional sensor added. The purpose of adding further sensors is to have a greater understanding of external factors towards the intended purpose. An example, one sensor may be used to determine presence of an object but would provide limited information. To understand greater information such as the amount of pressure being applied by the presence of the object, additional sensors may be added.

A method and system of having increased amount of sensors while minimizing electrical connections per sensor is having the electrical connections in a matrix setup with a first and second conductive path intersecting, yielding a plurality of sensor areas at each intersection of the first and second conductive paths as shown in FIG. 1. In FIG. 1, an example system 100 of a flexible apparatus and system for detecting pressure is illustrated. An electronic controller 102 directs electrical current along conductive paths, conductive path 106 to second conductive path 108 leading in one direction, and conductive path 104 to first conductive path 110 leading in a direction perpendicular to conductive path 108, thereby creating a sensor at each intersecting point 112. Conductive textile strips define conductive paths 108 and 110 are an example embodiment used in a grid where each intersecting point determines the surface coverage of the sensing area 112. The sensing area 112 can be adjusted to cover less surface area coverage by reducing the sizes of the conductive textiles that define conductive paths 108 and 110. At each sensing area 112, the conductive paths 108 and 110 can include respective exposed conductive surfaces at each sensing area 112. Conductive paths 108 and 110 can be defined by other conductive elements in other example embodiments.

Figure 2A:
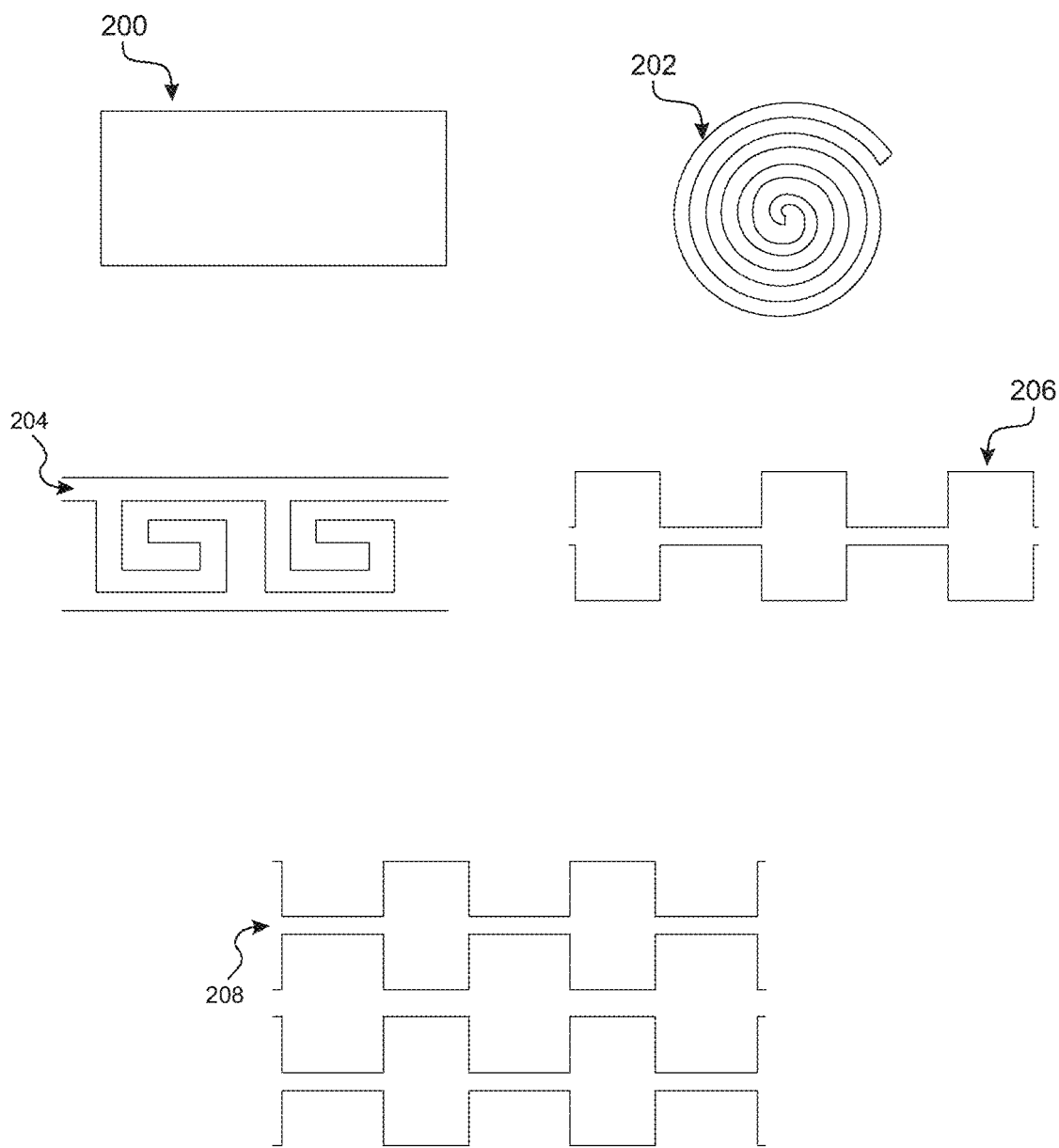
FIGS. 2A, 2B, 2C, 2D, 2E and 2F show examples of repeating pattern units for a conductive path.

FIG. 2A illustrates different patterns that can be used as examples, where efficiency can be improved with a reduction of materials used. A conductive textile strip 200 as an example can be utilized more efficiently by using less materials and accomplish the same intended outcome or effective sensor coverage area. A spiral pattern 202 is an example of a circle that can be split and divided into two equal parts while covering the same effective area of detectability with half the amount of material, for example.

An example is demonstrated with one conductive textile strip 200 being divided efficiently using the spiral concept into two equal parts 204 using half the amount of materials to cover the same effective area of detectability in an embodiment demonstrated in conductive paths 108 and 110. A further demonstration of a conductive textile strip 200 being divided efficiently is 206 with less of the conductive textile material in gaps that may be placed on a grid where there is no intersecting conductive textile material, where the area with greater amounts of the conductive textile materials may be placed at intersecting points for conductive paths 108 and 110 to maximize surface area to increase the sensor area coverage. A conductive textile strip 200 may be divided for efficiency in the example 206 through the example demonstration pattern 208.

An illustration of an example embodiment of a setup using the conductive textile strip 200 divided for efficiency 204 is demonstrated. An illustration of an example embodiment of a setup using the conductive textile strip 200 divided for efficiency pattern 206 and pattern 208 is demonstrated. An illustration of an example embodiment of a setup using the conductive textile strip 200 on second conductive path 108 and overlap of a conductive textile strip 204 on first conductive path 110 is demonstrated.

Figure 2B:
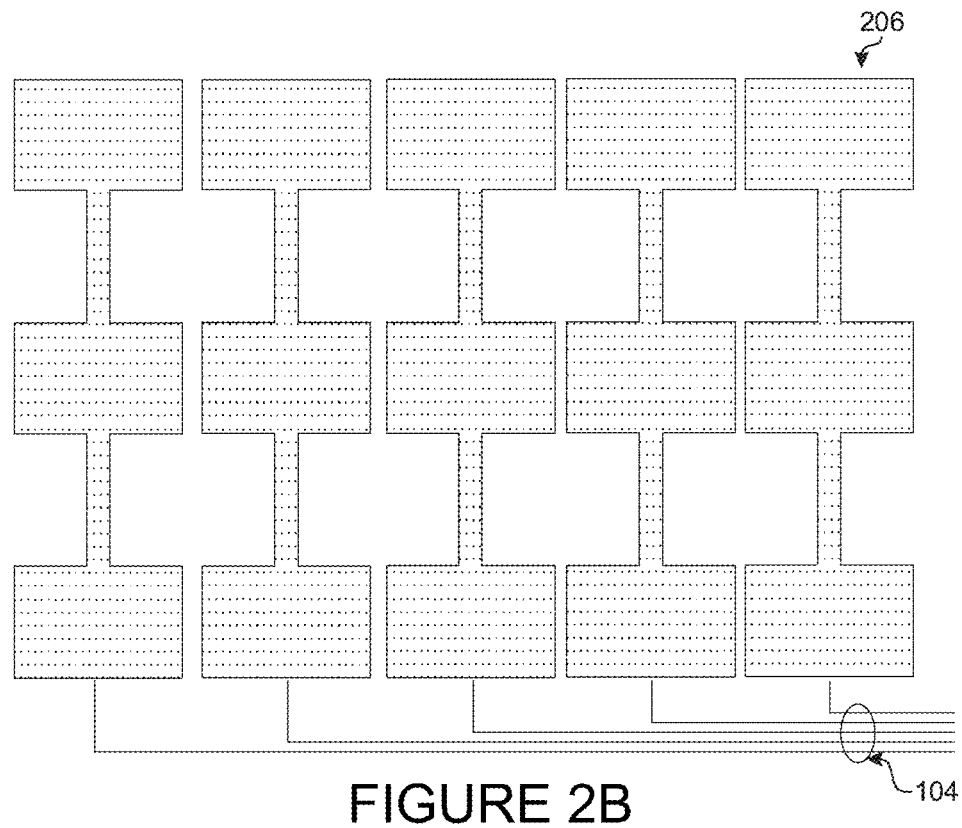

FIG. 2B illustrates an example conductive strip 200 that is divided with a design pattern 206 for efficiency to cover same effective surface area coverage at intersecting points that create a sensor location 112, with using less materials in the empty gaps where illustrated in the pattern 206.

Figure 2C:
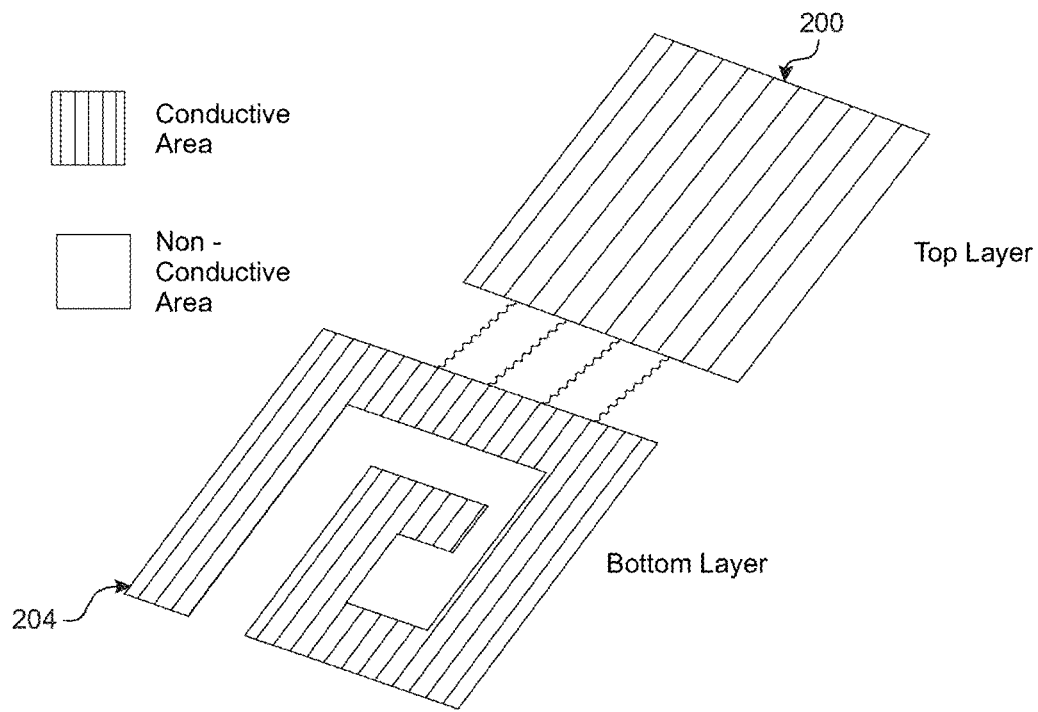

FIG. 2C illustrates an example conductive strip 200 that is used on one conductive path, and a textile strip that is divided using half the material 204 for a second conductive path, while covering the same surface area as the first conductive path 200.

Figure 2D:
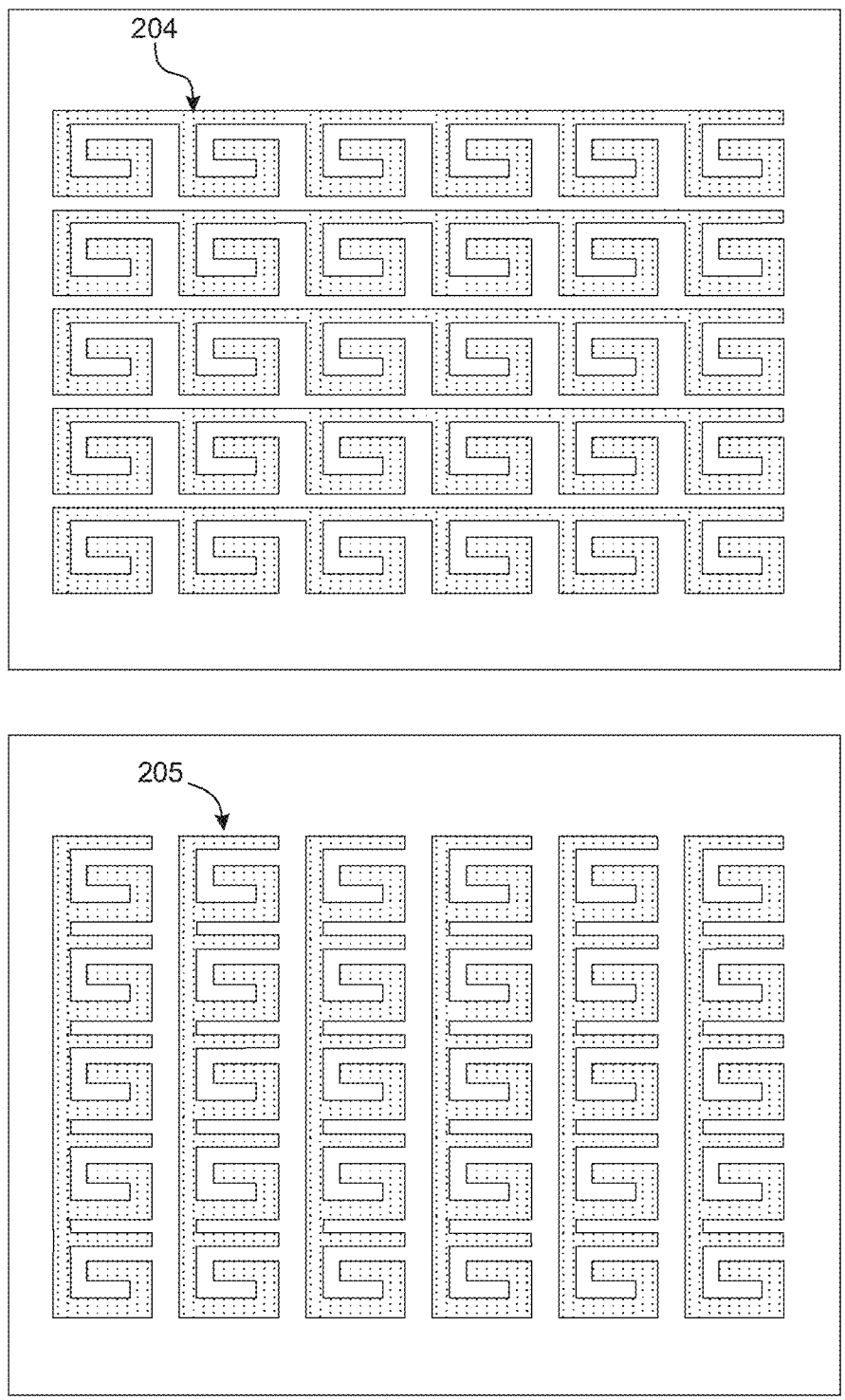

FIG. 2D illustrates an example of a conductive strip 200 that is divided and used for first conductive path 204 leading in one direction and second conductive path 205 leading in a perpendicular direction to 204, demonstrating that the same surface area coverage could be achieved using half the materials.

Figure 2E:
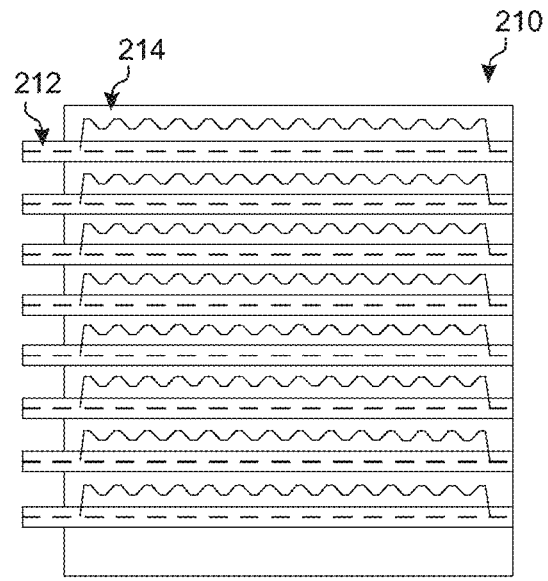
Figure 2E:
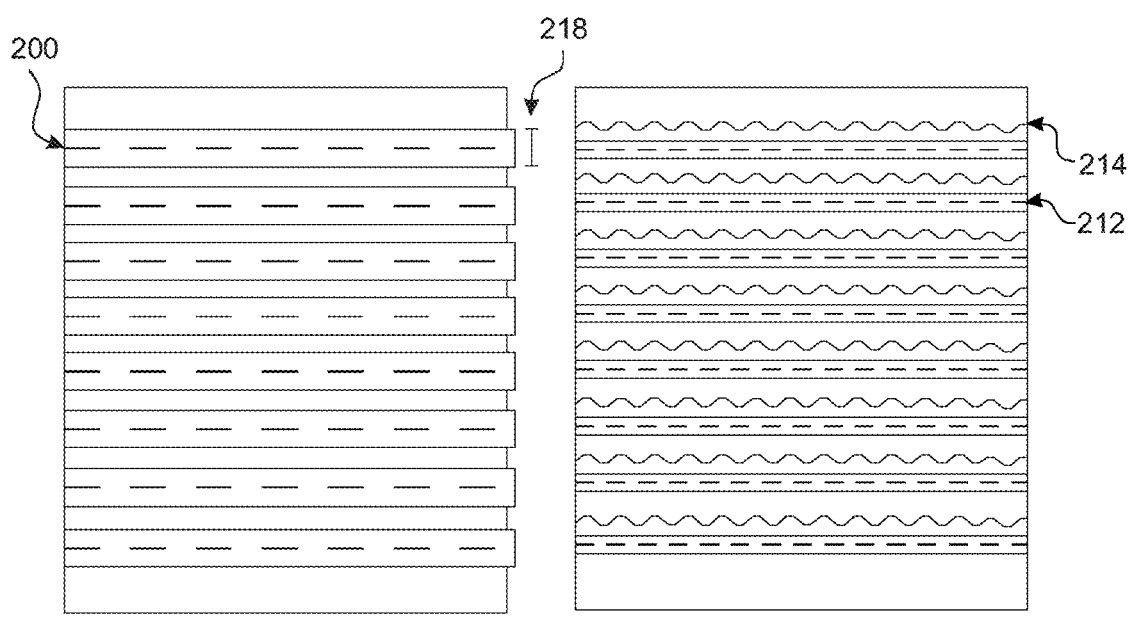

FIG. 2E illustrates an example using conductive fabrics 212 and conductive threads 214 for a more efficient method of covering greater surface area of sensing using less materials for one conductive path, as compared 218 to a conductive strip 200.

Figure 2F:
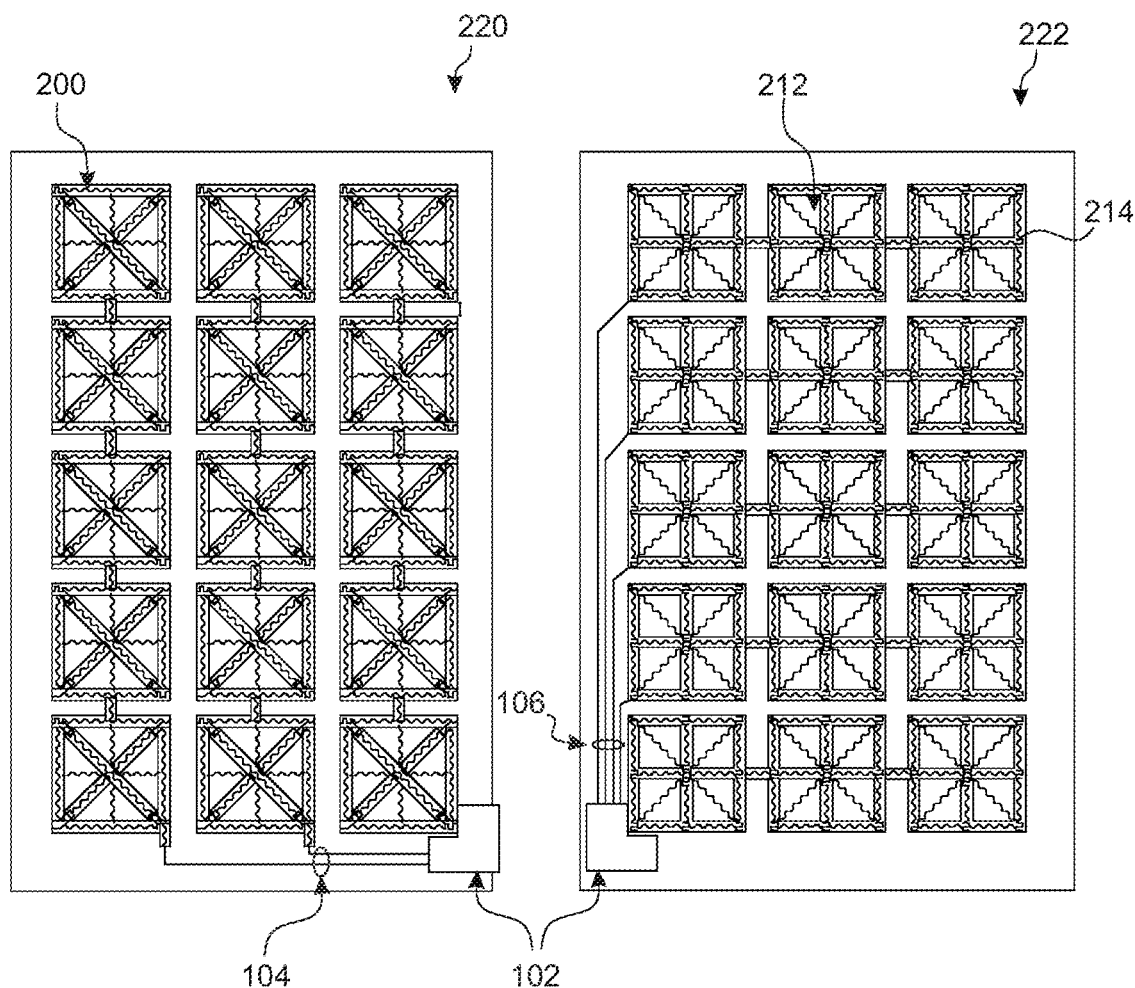

FIG. 2F illustrates an example using conductive fabrics 212 and conductive threads 214 in a second example conductive path design 220 and 222 using conductive fabrics and threads for a more efficient method of covering greater surface area of sensing using less materials.

Figure 3:
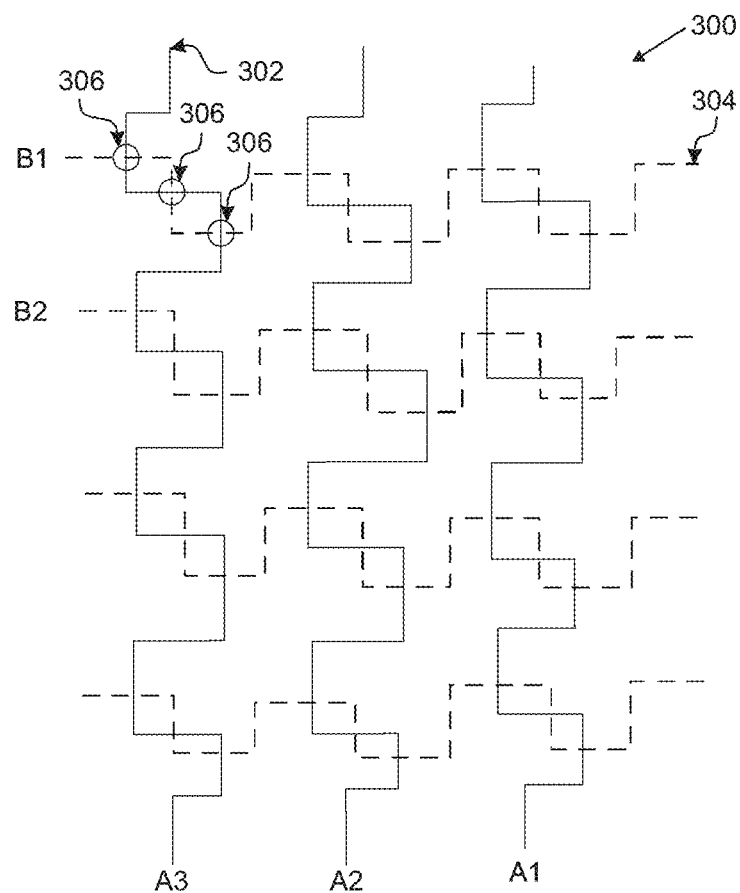
FIG. 3 shows by way of an example embodiment in a matrix format, where a setup requiring multiple points of contact to make complete electrical connection such that reaching a maximum electrical signal will result from all points coming into contact.
Figure 3:
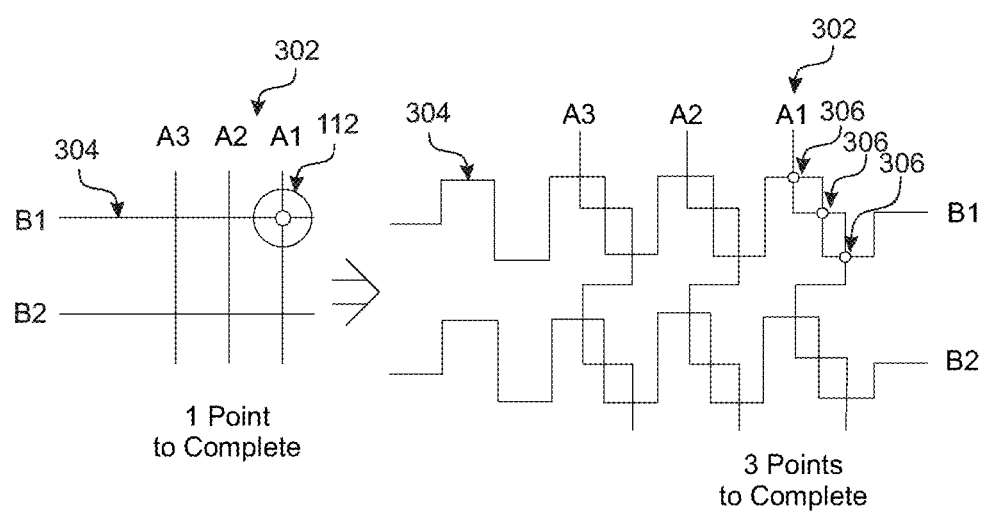

Generally a conductive path of a current carrying conductor has consistent voltage wherein when used alone for a single circuit or in a matrix would yield a result of sensing from two points coming into contact determining minimal electrical signal variance such as being on or off. There is the ability of determining signal variance based on the amount of force or pressure applied at each intersecting point that creates a sensor by increasing the contact points at each intersection as illustrated in FIG. 3. This illustration is an example embodiment 300 of a matrix setup in an intersecting grid 302 and 304 like that of conductive textile strips defining conductive paths 110 and 108.

For example, a cross-sectional area of a conductive material is proportional to the resistance. For example, the resistance R of any material with a uniform cross-sectional area A and length L is directly proportional to the length and inversely proportional to its cross-sectional area. In mathematical form, $R = \rho * L/A$, wherein the Greek letter rho ($\rho$) is known as the resistivity of the material. Resistivity is a physical property of the material and is measured in ohm-meters.

For example, liquids flow through large-diameter pipes easier than they do through small-diameter pipes. The same general principle holds for the flow of electrons through conductors. The broader the cross-sectional area (thickness) of the conductor, the more room for electrons to flow, and consequently, the greater the conductance and the easier it is for flow to occur (e.g. less resistance).

By a similar principal, the amount of surface area contact between the first conductive path 110 and second conductive path 108 determines the amount of resistance or conductivity there between. When a DC power source or charge is applied to the first conductive path 110, a resultant voltage signal is detectable from the second conductive path 108.

Conductive materials have varying levels of conductivity and electrical resistance. Utilizing the physical properties of natural resistance to the benefit of electrical sensing, variable signal detection can be performed through corresponding with the amount of points coming into contact at each intersecting point creating a sensor area 112 as illustrated in FIG. 3. Each contact point 306 comprises an exposed surface area of each of the conductive paths. An example being if one of three of the points 306 come into contact, the effective resistance will be greater and only approximately ⅓ of the voltage signal will be detected. As illustrated, an example embodiment of a conductive path design in a matrix setup 302 and 304 requiring multiple points of contact 306 to make connection at each intersection of first conductive path 110 and second conductive path 108 will result in such that reaching a maximum electrical signal at each intersecting sensor area 112 requires all points 306 (three in this example) being in contact, and the voltage signal detection will correspond with the amount of points that are in contact with each of the corresponding points 306 in the individual sensor area 112.

Figure 4A:
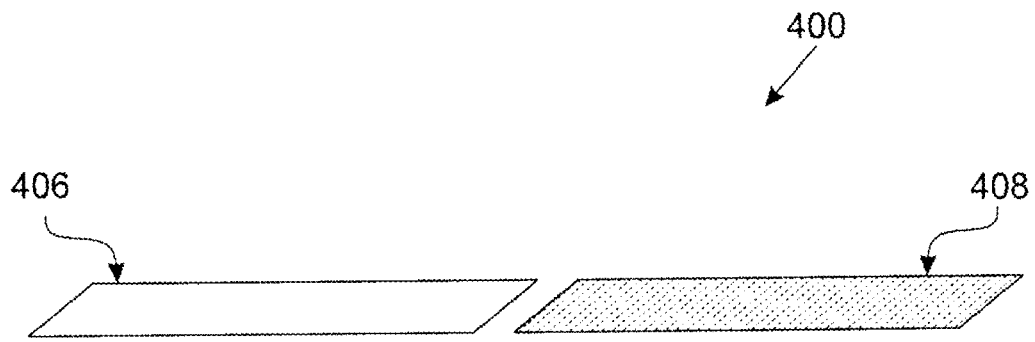
FIGS. 4A, 4B, and 4C shows an example embodiment of measuring higher electrical signal variance with first conductive path overlapping second conductive path to increase surface area contact.
Figure 4B:
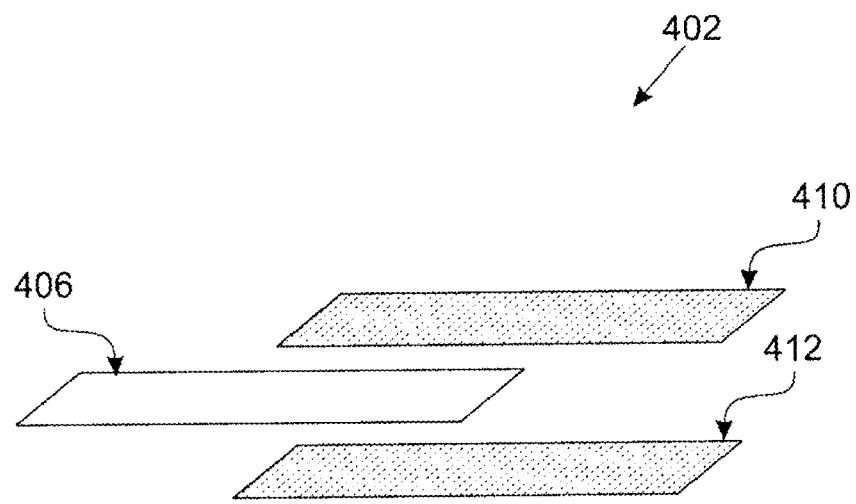
Figure 4C:
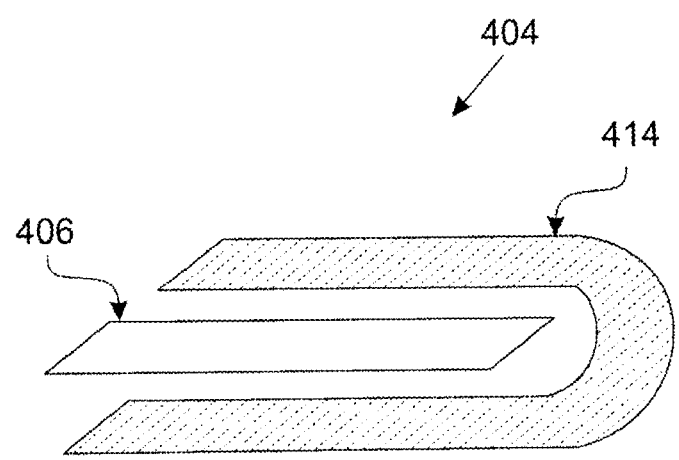

FIG. 4 illustrates examples of conductive path designs beginning with a first design 400 where a first conductive path 406 input and a second conductive path 408 output is demonstrating a connection, in an example being a circuit, that results in a completion of a circuit.

An example of a second conductive path design 402 is illustrated with a first conductive path 406 input, a second conductive path 410 output, and a third conductive path 412 output whereby if the first conductive path 406 has an input electrical signal, the second 410 and third 412 conductive paths coming into contact with the first conductive path 406 will result in a higher electrical signal output due to greater surface area contact, similar to increasing a diameter of a wire to increase conductivity and decrease resistance. This may be beneficial to increase sensitivity and data range in sensor applications, but for data range would require the sum of the data output of the circuit of conductive path 406 and conductive path 410, and the circuit output of conductive path 406 and conductive path 412. By increasing the amount of contact surface area of the second conductive path 410 and third conductive path 412 coming into contact with the first conductive path 406, similar to increased contact points 306, will allow an increase of voltage signal due to the greater conductivity and lower resistance at the contact points.

An example of a third conductive path design 404 illustrates an example of a first conductive path 406 input and a second conductive path 414 output, where increasing the amount of contact surface area of the second conductive path 414 coming into contact with the first conductive path 406, similar to increased contact points 306, allows an increase of resultant voltage potential and extracting unspent energy due to increased conductivity and decreasing resistance. This design 404 may be beneficial to increase sensitivity and data range in sensor applications, and for data range where it also improves efficiency over conductive path design 402 as it reduces the amount of electrical connections required whereby a second conductive path 414 combines two required connections of a second 410 and third 412 conductive path into one conductive path 414.

As even conductive materials have some natural resistance, increasing cross-sectional area contact size is to provide additional conductive paths for the electricity to flow over greater distances. Similar to this is increasing the amount of contact points 306 correlating to each intersecting point 112 from the first and second conductive paths 110 and 108 coming into contact to create a greater signal output, and increasing the amount of surface area contact 414 correlating to the first conductive path 406. More contact points increases conductivity between the first and second conductive paths 110 and 108. Through this aspect of greater surface area contact 404 and multiple points of contact 306 at each intersecting point, voltage potential increases at each additional contact point with resistance changing as a result of the corresponding applied force.

Figure 5A:
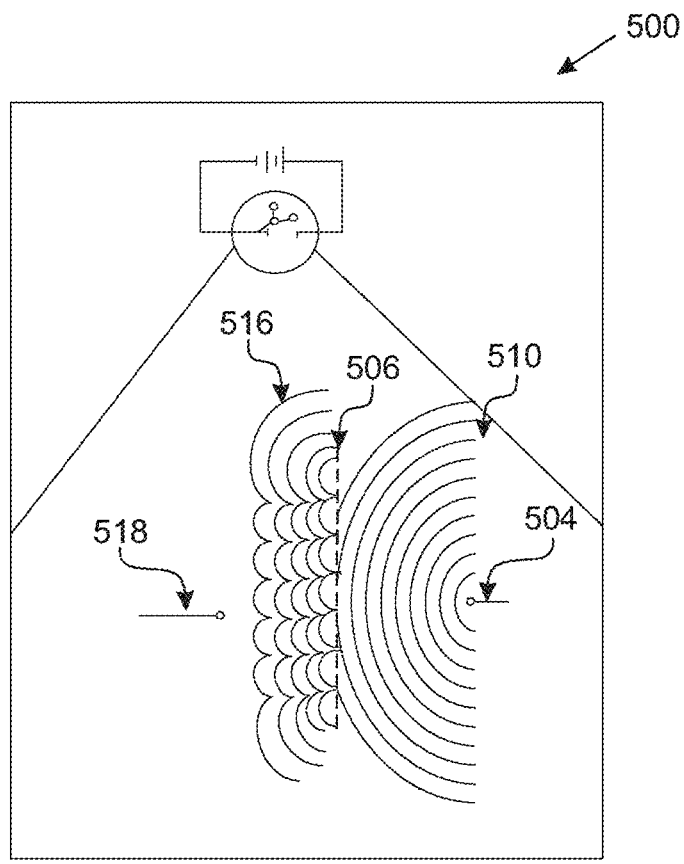
FIGS. 5A and 5B show example diagrams of measuring electrical signal variance while the apparatus remains in constant electrical contact.
Figure 5A:
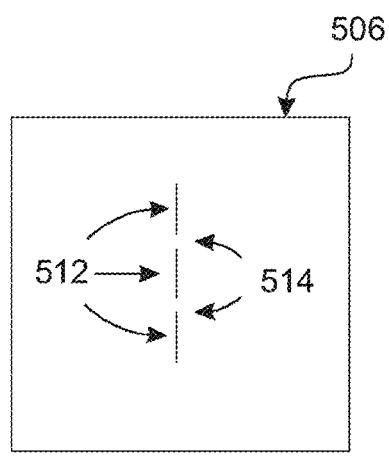

Sensor drift and creep is a common occurrence for pressure sensors over periods of time. In situations where there is constant contact, in an example embodiment, electrical paths can be diverted through dispersion to reduce strain on the conductive paths in order to minimize wear from constant electrical contact. FIG. 5A illustrates a diagram of a circuit 500 with the effect of a conductor 504 with an electrical path that is distributed by conduction layer 510. Conductive layer 510 is, for example, a conductive material or a fabric with many densely packed conductive threads. The electrical path through the conductive layer 510 is configured to come into contact with a load, which will be referred by way of this example as a resistive layer 506 that contains distributed conductive threads 512 spaced out and separated by non-conductive threads 514, and the electrical path is then further distributed by conduction layer 516 and continues to the output conductor 518 providing an electrical signal output that is detectable. Electrical path distribution by conduction layer 510 through a resistive layer 506 is dispersed with distributed electrical contact through conductive threads 512 and separation with non-conductive threads 514 through insulation by the non-conductive threads and insulation through natural air separation. To lessen electrical resistance and increase electrical signal conductance, further contact through external environments, by way of example of pressure being applied, will compress input conductor 504, resistive layer 506, and output conductor 518 together as if all combined elements were one larger single conductor, and result in an increase of electrical signal conductance as more surface area contacts are made as a result of the applied pressure. When full pressure is applied, conductance along input conductor 504, resistive layer 506, and output conductor 518 is maximized and the detectable electrical signal from output conductor 518 is at maximum, e.g. on or about maximum 5 V or a maximum calibrated value of 1024.

Figure 5B:
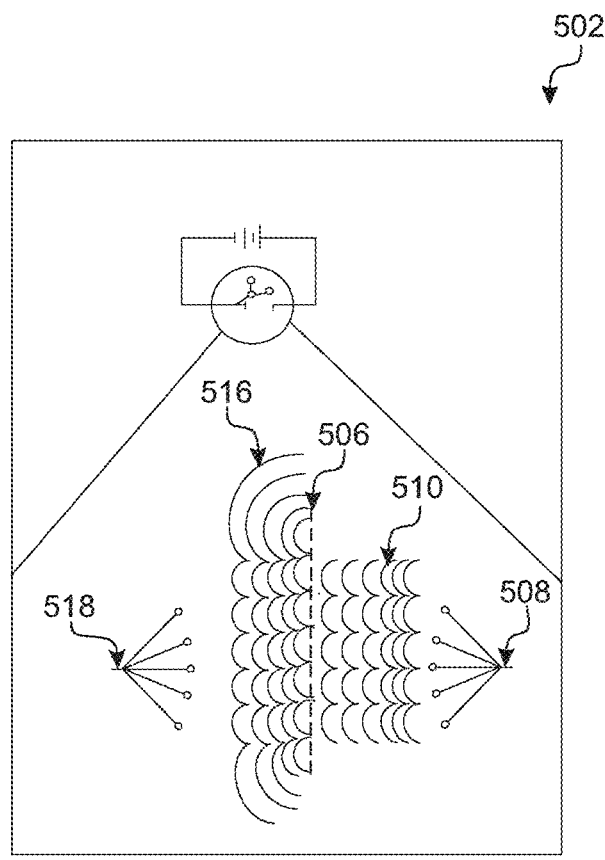
Figure 5B:
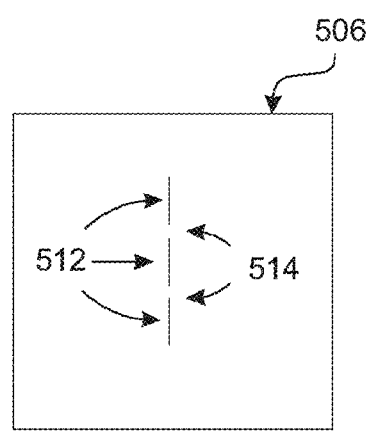

FIG. 5B further illustrates a diagram of a circuit 502 with the effect of a conductor 508 that demonstrates the ability to detect signal variance by increasing the amount of different input paths of a conductor 508 with electrical path distribution by conduction layer 510 that is distributed through the middle resistive layer 506 and continues with further distribution by conduction layer 516 through conductor 518, where electrical signal output will vary correlating to the amount of input conductor 508, resistive layer 506, and output conductor 518 that are in conductive contact. It follows the previous example FIG. 5A that the increasing surface area of points of contact of all combined elements will result in acting as a single conductor having greater conductance and lower resistance, resulting in an outcome of a greater electrical signal output. When full pressure is applied, for example, conductance along input conductor 508, resistive layer 506, and output conductor 518 is maximized and the detectable electrical signal from output conductor 518 is at maximum, e.g. on or about maximum 5 V or a maximum calibrated value of 1024.

Example embodiments of systems and methods demonstrated in FIGS. 3, 4, 5A, and 5B are also beneficial to be used in printed circuit board and electronic chips to allow greater signal variance to increase the functioning capability of integrated circuits that are generally limited to performing binary tasks.

Figure 6A:
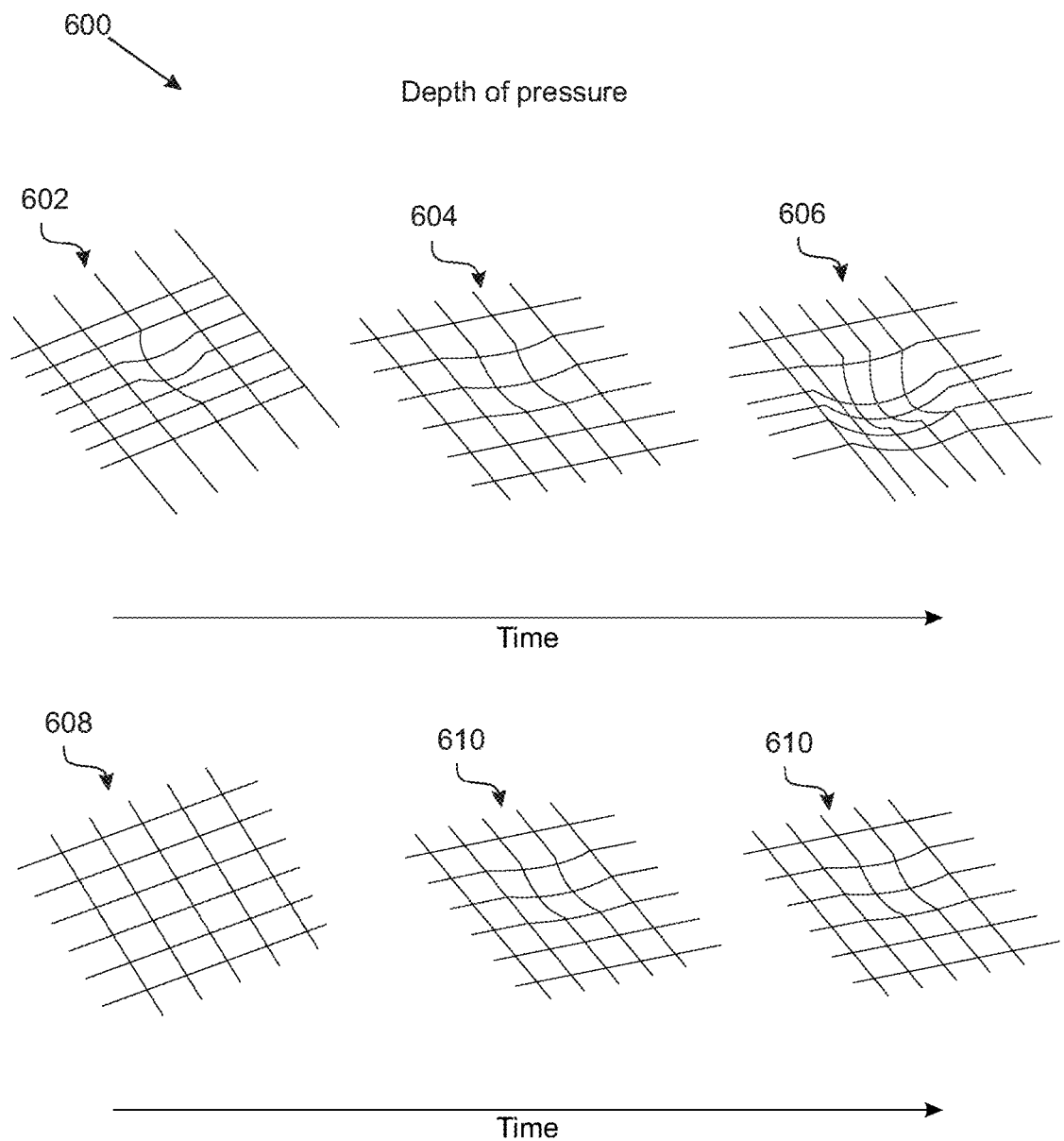
FIG. 6A shows representative illustrations of the distortions that the flexible conductive apparatus undergoes when pressure/force is applied.

FIG. 6A illustrates distortions of the flexible conductive apparatus by way of demonstrating different forces of pressure applied on the apparatus over time 600. When pressure is applied on the apparatus 602, represented is a visual demonstration as what is detectable with the apparatus. As further pressure is applied on the apparatus, there is further distortion 604 with the ability to detect increasing amounts of pressure 606 on the apparatus, thereby representing the ability for the apparatus to determine depth and volume corresponding to the amount of pressure applied. When there is no pressure applied 608, and then consistent pressure is applied as could be due to by way of example a still object over time, the detection of amount of pressure remains stable 610.

Figure 6B:
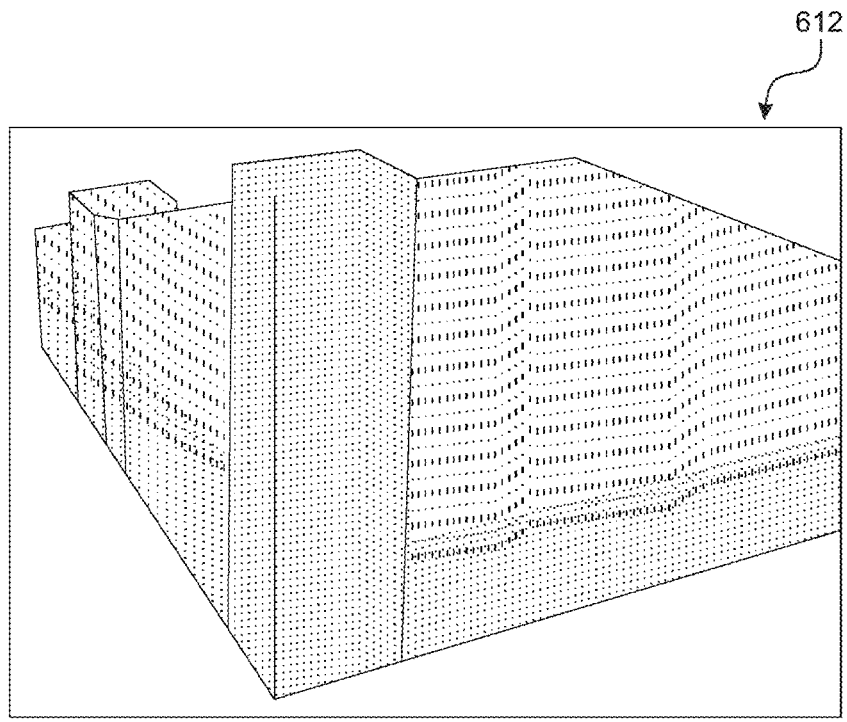
FIG. 6B shows an example of the flexible conductive apparatus in three-dimensional imaging.

FIG. 6B illustrates distortion of the flexible conductive apparatus by way of demonstrating different forces correlating to the amount of pressure applied on a three dimensional graph 612 with the highest amount of pressure applied at the corner as represented in the figure, demonstrating the ability for detecting three-dimensional mapping, location, and weight differential throughout the apparatus.

Figure 6C:
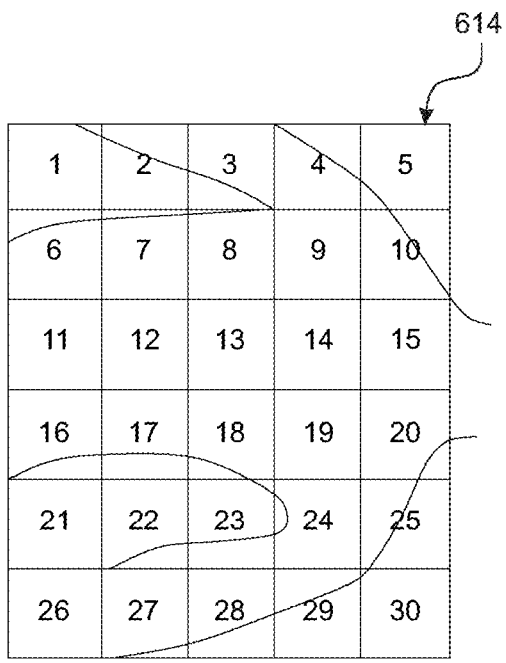
FIG. 6C shows an outline of a two dimensional mapping of a body lying on the flexible conductive apparatus.

FIG. 6C illustrates a two-dimensional mapping, with an outline of the body, through determining active sensors in one example embodiment of controlled testing of the flexible conductive apparatus as a health monitor application. In this example configuration, the flexible conductive apparatus system consisted of 30 sensors configured in a 5×6 matrix.

It will be demonstrated further, for applications in healthcare patient monitoring. Each individual sensor has the ability to detect depth and variations of pressure, where sensor regions can be segmented to determine active versus inactive sensors corresponding to applied pressure areas versus no pressure areas 614, and changes in pressure levels among the sensor areas. This is a beneficial outcome by demonstrating in an example of a human body that lays on a bed and rolls to their side or around to other parts of a bed, there will remain continuous output of electrical signals where the flexible conductive apparatus system is in contact with the body to provide continuous monitoring of a patient/user. An additional benefit is providing further indication of signal noise such as jumps or spikes of the electrical signal outputs, where the two-dimensional mapping will provide reference as to originating signal noise that may be attributed to movement on the flexible conductive apparatus.

Figure 7:
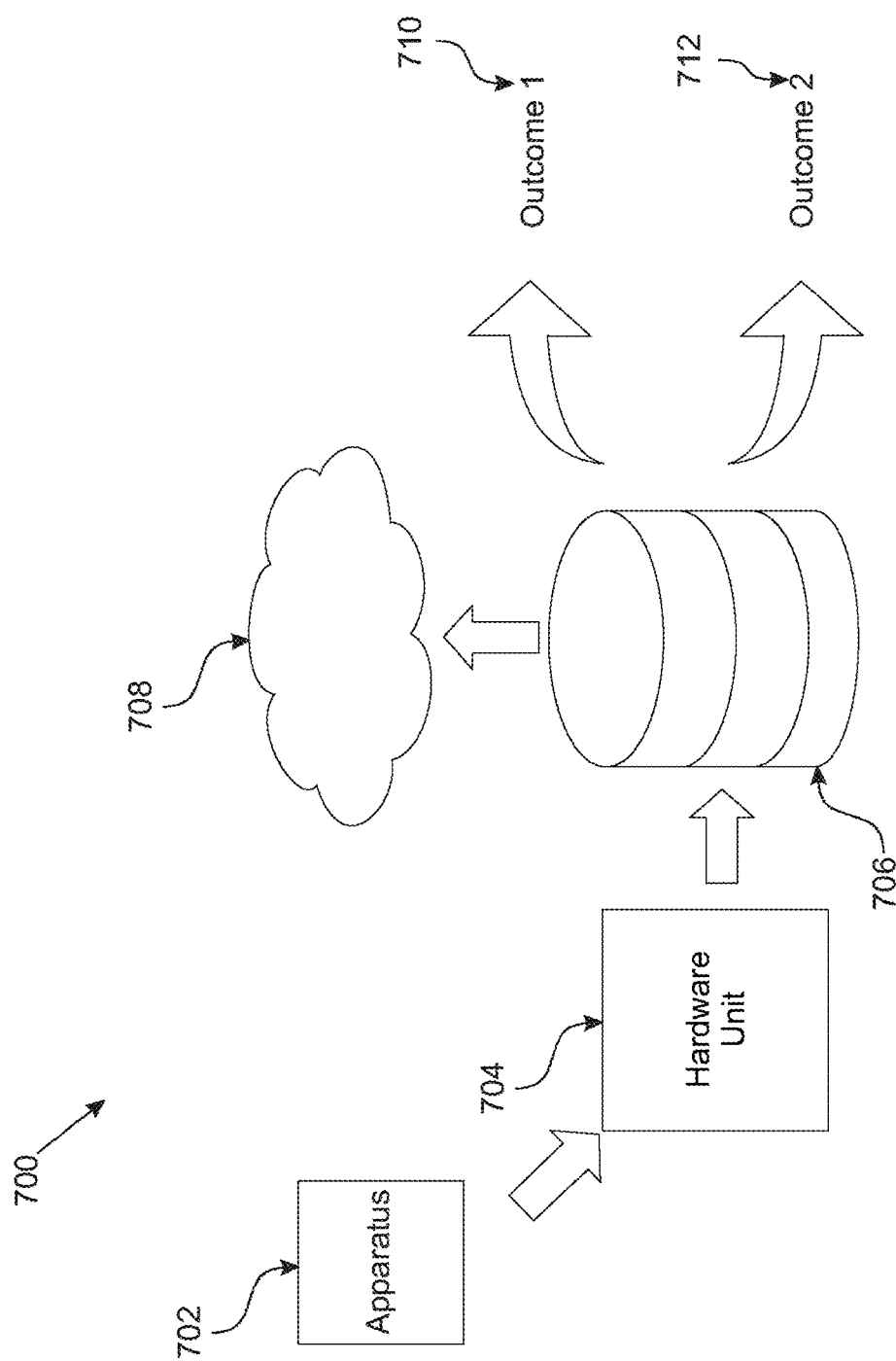
FIG. 7 shows an embodiment of a system incorporating a flexible conductive apparatus as a mat or a functional bed sheet health monitoring device, a hardware unit, a database, and a cloud server.

FIG. 7 illustrates an example embodiment of a flexible conductive apparatus 702 in a monitoring system 700. The flexible conductive apparatus 702 outputs electrical signals to the hardware unit 704, that may process the signal information on the hardware unit 704 and/or transmit the raw electrical signal information to a database 706. The database 706 may then conduct further processing of information and/or transmit the information to a cloud server 708, for further analysis that may produce by way of example in this illustration one intended outcome 710, or an alternative intended outcome 712. Data stored in the database can be used for health analysis, as well as for customized output functions such as notifications and/or alerts.

Another example embodiment of a system incorporating a flexible conductive apparatus 702 for a monitoring system 700 is for a surface area detecting three dimensional mapping, location, and weight differential throughout the apparatus with data analysis that can be used for monitoring inventory levels or presence of inventory items on an intelligent shelving unit, for an automated process of inventory control as one potential outcome 710, and/or the pre-ordering process for restocking inventory as an alternative potential outcome 712. In an example embodiment, rather than a flexible supporting layer, a rigid material (e.g. low or non-perceivable flexibility) such as a shelf incorporates the variable pressure sensor, and the minor deformations in the rigid material are detectable.

The flexible conductive apparatus is connected to a hardware unit which includes a microcontroller, a processor, a single board computer that comprises a wireless and wired network capabilities, multiplexers, analog-digital converters, amplifiers, alerting device, speakers, buzzers, LEDs/LED strips, accelerometer, gyroscope, or combinations thereof. The conductive apparatus serves as a resistance for current to pass through.

In a matrix design, for example, one side of the electrical connections of a second conductive path 108 (e.g., rows) to the conductive apparatus serves as an input signals and is connected to one MUX whereas the other side of the connections of a first conductive path 110 (e.g., columns) serves as the output and is connected to the other MUX. The MUX is then interconnected to the other components in the hardware unit. Through multiplexing signals very rapidly, one side of the connections for the second conductive path 108 (input) is sending voltage and the other side first conductive path 110 (output) is reading signals and determining if any intersection between the column and row is pressed along with the amount of pressure is applied. As an analogy, the conductive apparatus serves as an array of piezo sensors and/or variable resistors that allows passage of current through to complete the circuit and output a signal. The amount of force and/or pressure applied dictates how much current is passing through with greater pressure allowing more current flow to output a greater electrical signal.

Pull-down resistors are included with the analog input signal to stabilize and improve the consistency of the values across all signals. Pull-up resistors are also included with the input signals in order to increase the range of sensitivity.

Figure 8A:
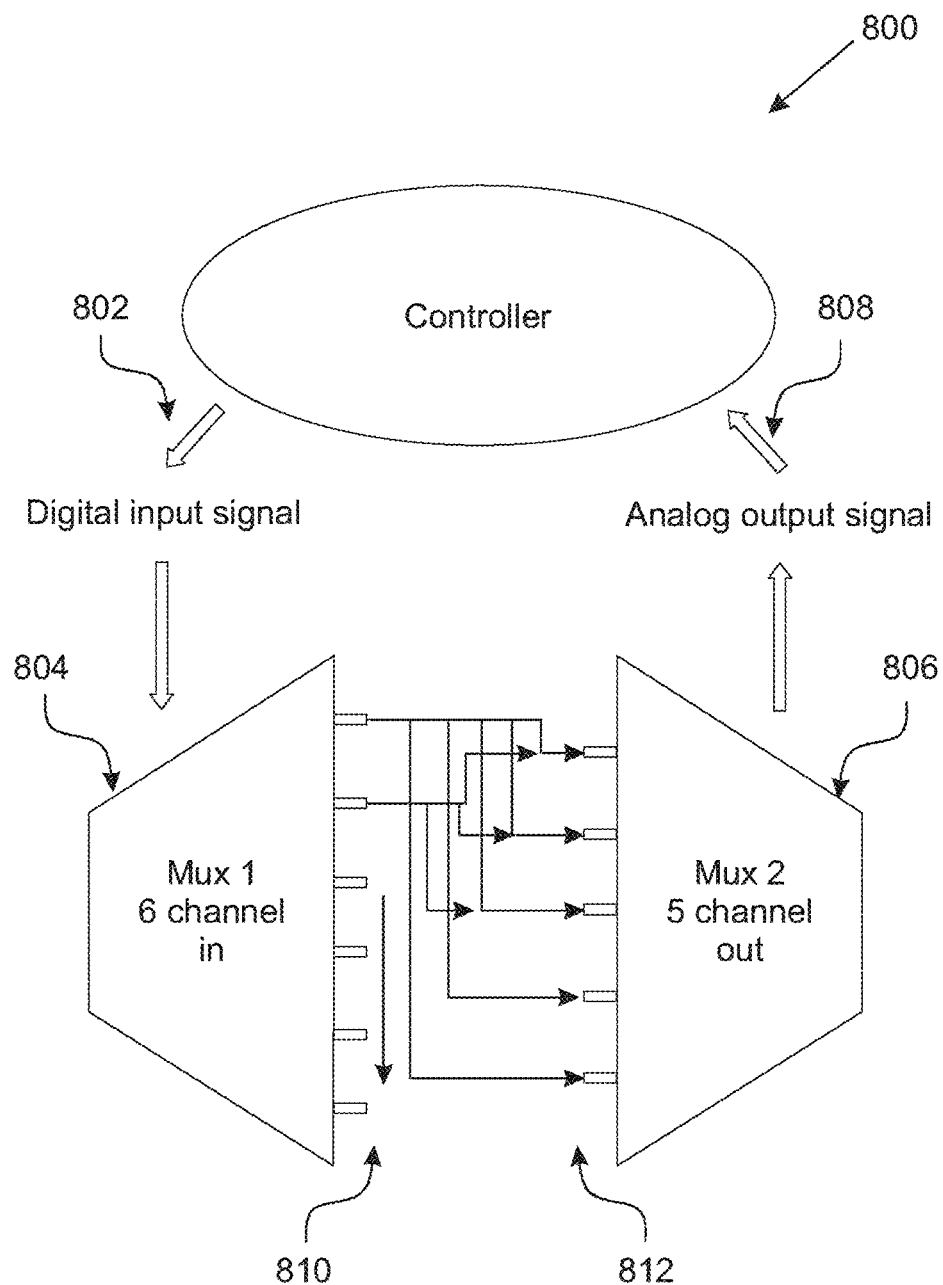
FIGS. 8A, 8B and 8C show an example of the conductive paths in a matrix grid, where the power signal is input into one multiplexer and the output signal is read from the other multiplexer, thereby being able to read multiple electrical signals with fewer connections for each sensor point.
Figure 8B:
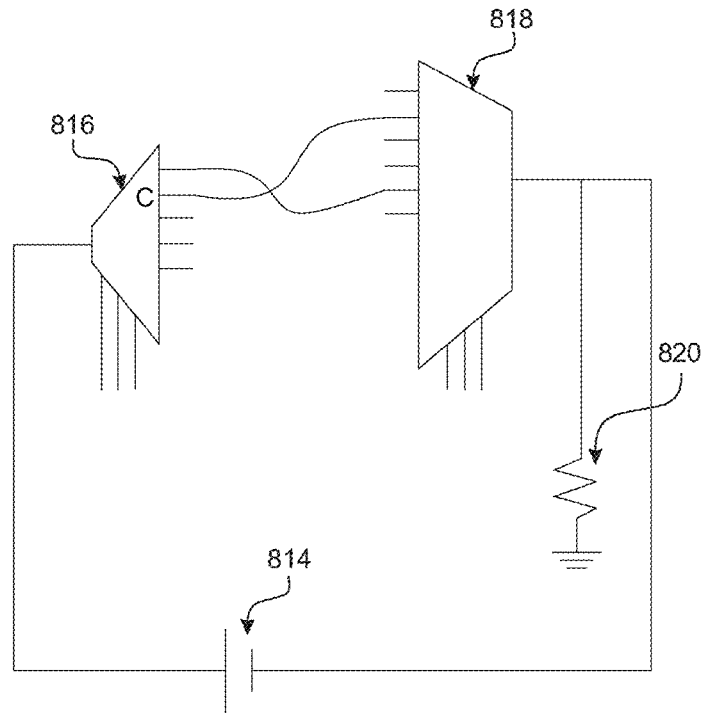
Figure 8C:
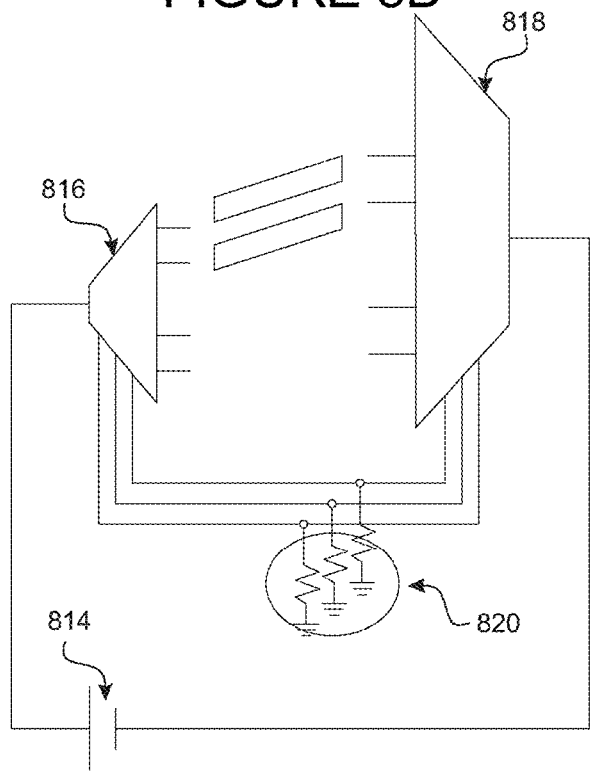

With the many applications the flexible conductive apparatus can be applied, FIGS. 8A, 8B and 8C illustrate the functioning of circuitry 800 that minimizes the electrical connections required by using a matrix setup that multiplexes electrical signals, while maintaining higher data range of output signals.

Example circuit setup using two multiplexers are illustrated in FIGS. 8A, 8B and 8C. Power is connected to multiplexers (MUX). In the example 800, two multiplexers take digital and/or analog inputs where the first conductive path 802 will input a single digital signal into MUX 804, and multiply the digital signals into the amount of combinations as in this example of 6 channel inputs 810, and be collected through a secondary MUX 806 that will receive multiple digital signals through the amounts of combinations as in this example of 5 channel outputs 812, thereby creating a 6×5 matrix outputting a combination of 30 sensors in this example. Between MUX 804 and MUX 806, there will be signal output of variable electrical signals corresponding to the amount of sensor areas coming into contact, along with the amount of pressure applied at each sensor area.

FIGS. 8B and 8C further illustrate the circuitry in an example setup with a power source 814, an input MUX 816, an output MUX 818, and pull-down resistors 820.

Functional textiles are useful in manufacturing instruments that can generate information from an input signal resulting from contact with the textile. Such instruments can detect the amount or variations of force/pressure applied and may also have a stimulus response built in. An example of an application of such an instrument is embedding a flexible conductive apparatus in accordance with an example embodiment into everyday furnishings such as couch lining, carpets, mats, flooring, or linen to detect when there is presence of a force/pressure applied. Such an application can be useful in monitoring behavior to create real-time information of the presence of individuals in a building or the location of an individual. It can also monitor if there is a fall, and continue monitoring while emergency responders are dispatched. All of these may be useful in monitoring, for example, Alzheimer or dementia patients, or in conserving energy by powering devices based on real-time information of the presence of individuals in a location.

Another example application involves embedding a flexible conductive apparatus in medical devices such as a compression instrument, bedding, or leads to monitor levels of pressure or changes in pressure arising from heart rate or pulses, or a body contact during inhalation and exhalation or other respiratory changes. This opens up the potential for future applications in general patient health monitoring without the need for any leads and/or attachments to the patient body.

Figure 9:
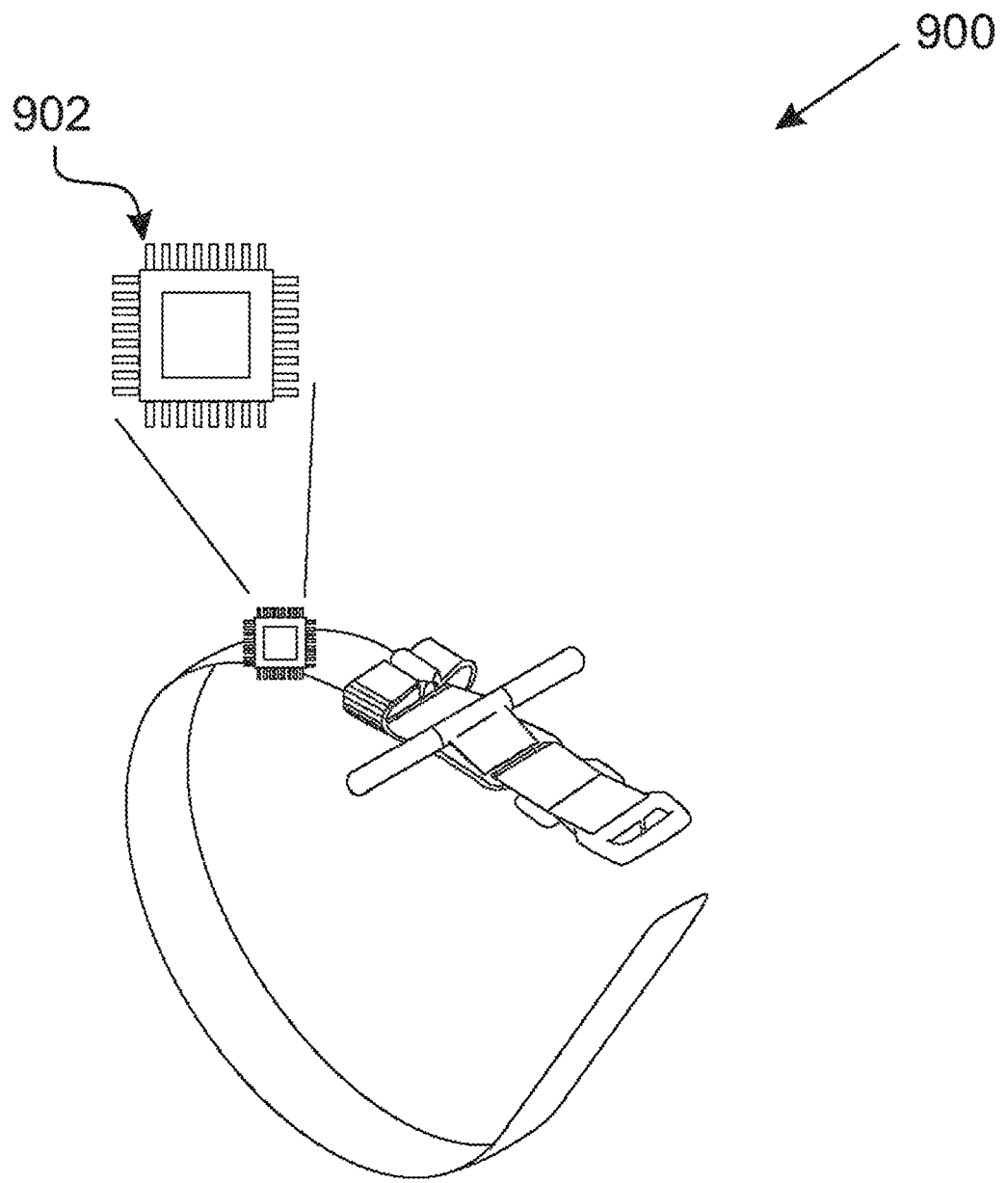
FIG. 9 shows an example embodiment of a flexible conductive apparatus system that can be attached to an existing device without alteration, to increase the efficiency for measuring such device outcomes as intended.

For example, illustrated in FIG. 9 is where a compression instrument tourniquet 900 is shown, where a tourniquet 900 when used requires a consistent amount of pressure to be applied and maintained on a body part to occlude blood vessels, preventing bleeding such as traumatic bleeding in emergency situations. This example embodiment demonstrates a flexible conductive apparatus system 902 that can be attached to existing devices such as the compression instrument tourniquet 900 to improve outcomes of providing continuous monitoring, rather than having to make alterations on the devices. The flexible conductive apparatus system 902 can comprise any of the described flexible conductive apparatus 702. This can be helpful in military applications or for emergency personnel who use combat application tourniquets (CAT) in situations where the monitoring of pressure is difficult to attend to in high-stress situations requiring CATs, and often when muscles contract, pressure from CATs require retightening to prevent further bleeding that would otherwise increase the risk of fatality. The flexibility of the conductive apparatus can be applied in any location or on any part of the body as it can take any form factor, and monitor applied pressure continuously and notify if there is a decrease in pressure that falls below a set parameter, alerting for the need for attending to, in order to maintain the required level of pressure. In addition, the apparatus can monitor the length of time of application of the tourniquet 900, where extended periods of time being applied may result in potential risks of amputation.

In example embodiments, beddings incorporating functional textiles can provide information regarding, for example, respiratory changes or length of time of complacency. While other devices require direct attachments to the body, the functional textiles of example embodiments maintain contact with the body while measuring changes in pressure and weight distribution from expansion and contraction of the body, and can be useful for long term research with events leading up to health outcomes, or alerting irregular breathing, or mitigating pressure ulcers from forming due to limited movements. Measuring vibrations emitted by pulses in the body using techniques such as ballistocardiography may be one method that can provide information regarding heart rate. One benefit of using such functional textiles is the replacement of conventional approaches to vital sign monitoring which requires leads and attachments to the body, and offers a non-invasive solution using a common everyday item such as a bed sheet that has been made into a functional device using functional textiles. It would also provide more accurate information with a consistent baseline comparison, by limiting user bias while using the example embodiment while asleep. Temperature can also be monitored and determined using a thermoresistor (thermistor) or alternatively two differing conductive fabrics and/or threads, to measure electrical resistance at varying temperatures.

Pressure sensors, such as functional textiles, can also be embedded in shelving units to monitor inventory levels when they are running low or when items are not being renewed over a period of time. A real-time inventory system using a SMART shelving system can communicate inventory levels and a software component can be built to automate the ordering process.

Figure 10:
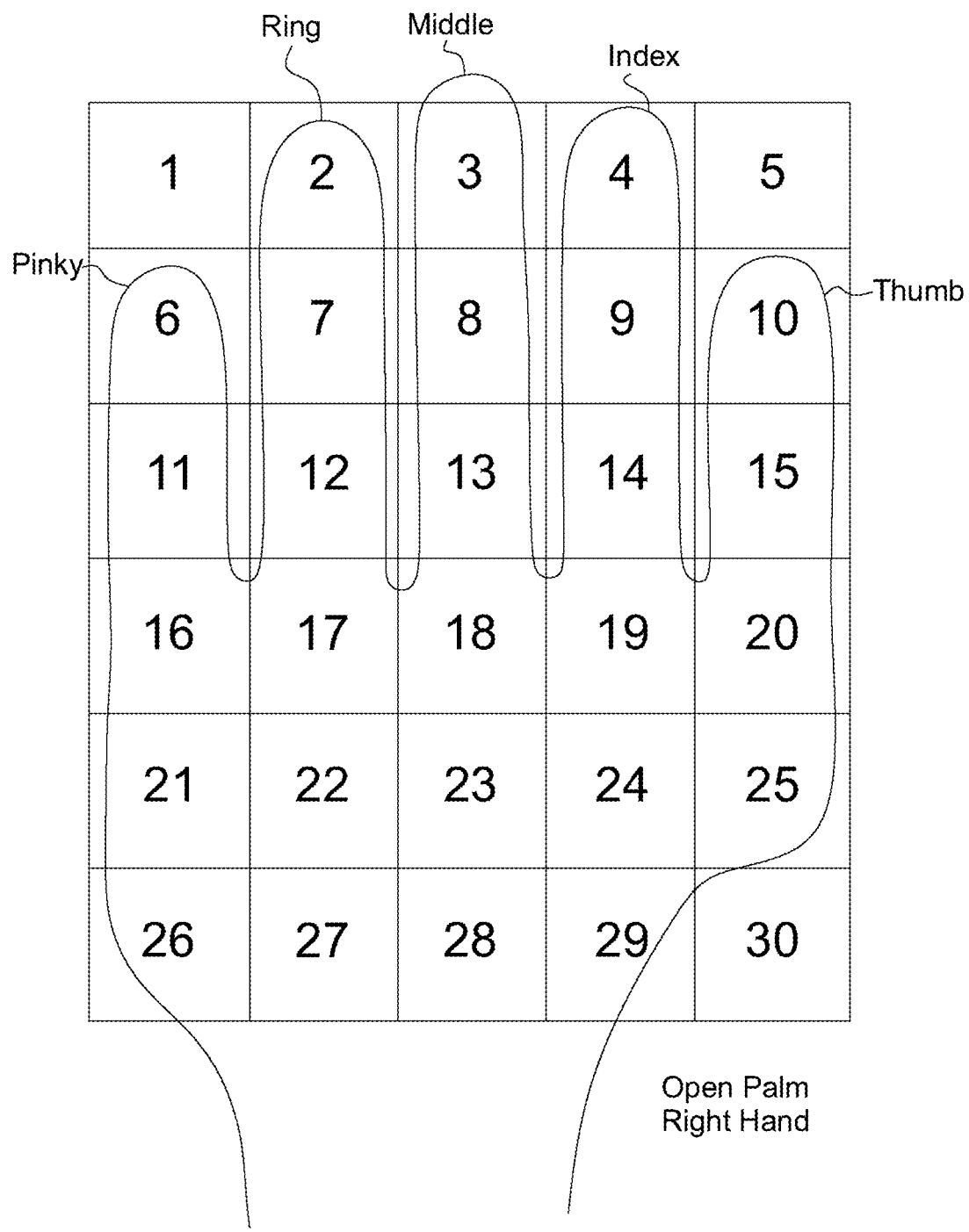
FIG. 10 shows an example embodiment of a flexible conductive apparatus system for artificial exterior skin allowing a robotic hand to have the sense of touch.

Yet another example application as shown in FIG. 10 is a flexible conductive apparatus system of an example embodiment in artificial exterior skin layers to provide the sense of touch to a robotic component such as a robotic hand. With the ability to determine amount of pressure with the sense of touch, a robot is configured to perform tasks that require further sensitivity such as being able to pick up delicate materials such as glass objects, without shattering the delicate materials as a result of too much force applied. The robotic component may also comprise a stimulus feedback response mechanism, communicating with an external element such as a user, a person, a device, and/or system. This is also a beneficial component in settings where having haptic feedback is advantageous. For example, in remote control settings for improving the safety of controlling robotics in explosive ordinance disposal (EOD) situations that may require a degree of sensitivity in handling delicate objects and knowing how much pressure is being applied. Another example embodiment is for clinical settings where a robotic component may be controlled from remote regions by surgeons that have specific expertise in performing certain types of operations. Another example embodiment is in manufacturing that requires the sensitivity of touch to improve the efficiency of tasks on a production line.

The flexible conductive apparatus can be used by itself, or it can be integrated with other objects to create functional textile instruments.

Two Layer Flexible Conductive Apparatus

Another example embodiment of a pressure sensor is described, comprising two layers of conductive materials with same or different levels of conductivity, and a design/setup with increased points of contact at each intersection of the two layers as a method combining a capacitive method of sensing to determine location, and resistive method of sensing to determine variability of force or pressure applied based on the amount of points in contact corresponding proportionally with the amount of points coming into contact at the intersecting point. In one embodiment, the pressure sensor comprises a conductive fabric or textile sensor.

With the development of interactive and smart textiles by integrating metallic type fibers with textiles as one method, electrical circuitry has changed how materials operate with conducting electrical currents. Levels of conductivity differ among the many materials available, and which also adds to the varied levels of inherent air resistance and insulation, or resistance of the materials relative to the conductive components by weight.

Having this difference in levels of conductivity between the two layers of highly conductive material eliminates, in an example embodiment, the need for a middle layer of resistive material, since this difference effectively acts as a barrier to a complete circuit and functionally carries out the same purpose as a middle resistive layer. In turn, in an example embodiment, this elimination of the middle layer reduces production costs. Current passing from a material having a lower level of conductivity will never reach a level higher than its own capacitance, when in contact with a material having a higher level of conductivity. Differences in capacitance can be measured and monitored during application of pressure where the two materials come further into contact.

In an example embodiment, the sensor or apparatus can be supported by one or more rigid layers for each conductive path. Rigid means a non-compressible surface, or a surface that is sufficiently rigid and low elasticity so as to be perceived to be non-compressible, without bending or stretching of the sensor apparatus.

In one embodiment of a flexible conductive apparatus in accordance with an example embodiment for detecting force or pressure applied to said apparatus, the apparatus comprises a first conductive path having a first level of conductivity and a second conductive path having a second level of conductivity different from the first. The first and second conductive paths are positioned such that they are in contact with each other. The apparatus also comprises a plurality of sensor areas. Wherever the first conductive path contacts the second conductive path and is in electrical communication, each of these contact intersections gives rise to a sensor area which generates a signal corresponding to the applied force or pressure.

As used herein, a "conductive path" refers to an electrical conductive path. In example embodiments, the conductive paths are made from conductive fabrics or textiles arranged in a particular pattern. Alternatively, conductive threads can be used to create conductive paths; however conductive threads are not used in some example embodiments since they have limitations in maintaining voltage strength through the conductive path over a distance, (approximately exceeding 10 cm in length for some conductive threads). In some embodiments, the conductive paths are made from a combination of conductive fabrics and threads to overcome this limitation. Connecting a conductive fabric with a conductive thread acts as one conductive path with a larger surface area. In example embodiments, a conductive path is provided as a layer or supported on a layer, and placed in contact with a second such layer of conductive path, forming a flexible conductive apparatus in the form of a sensor sheet.

As used herein, "sensor areas" refers to intersections or areas of contact where a first conductive path is in electrical contact with a second conductive path to complete a circuit. Each sensor area generates a signal corresponding to the applied force or pressure.

The flexible conductive apparatus functions contrarily to conventional wires. Conductive components are blended with non-conductive components to create the conductive paths, which provides a level of surface area resistivity. The greater the surface area of each sensor area, the less the resistance the current experiences when passing from the first conductive path to the second conductive path. The resulting signal when the circuit completes is then processed to determine the amount of force/pressure applied.

Applied force or pressure resulting in one hundred percent contact between the conductive paths will create the maximum threshold for a complete circuit. On the other hand, due to natural surface area resistance of a conductive path, a less than one hundred percent electrical contact results in a complete circuit that is less than the maximum threshold. This is made possible by varying the levels of conductivity of the materials. Material specifications differ when conductive components are combined with non-conductive components thereby creating natural air resistance and insulation. In turn different materials require different amounts of force to be applied in order for a circuit to complete and reach its maximum threshold.

In one embodiment of the flexible conductive apparatus, a complete electrical contact between the first and second conductive path at any one of the plurality of sensor areas will generate a maximal signal. Where there is partial electrical contact between the first and second conductive path at any one of the plurality of sensor areas, this will generate a less than maximal signal.

Conductive Material

A minimum of two conductive paths are required to make contact and complete a circuit. Sensitivity of the flexible conductive apparatus of force or pressure can be adjusted by using different materials with different levels of resistivity to make a conductive path, which also results in different levels of surface area resistivity. Selection of a different material will yield a flexible conductive apparatus with a different level of sensitivity, and in turn a different conductivity and therefore different surface area resistivity. For example, using a material having a lower conductivity and higher surface area resistivity for one of the two conductive paths will decrease the level of sensitivity of the apparatus since there is greater resistance to completing a circuit. In an alternate embodiment where a conductive layer is provided between the two conductive paths, using a material having a lower conductivity and higher surface area resistivity than the two conductive paths, this will also decrease the level of sensitivity of the apparatus.

Conductive Path Design

In a two-dimensional plane, the design of a conductive path can be manipulated in patterns such that when the conductive path is provided as a layer or supported on a layer, there are conductive areas and non-conductive areas. For example, in some embodiments the conductive path runs linearly with gaps in between each linear segment. Turning to FIG. 1, in the illustrated embodiment, a vertical conductive path overlaps with a horizontal conductive path in a grid pattern. The resulting sensor areas, where the two conductive paths are in electrical contact, are arranged in a matrix. In other embodiments, repeating patterns and units can be used as shown in FIGS. 2A, 2B, 2C, 2D, 2E and 2F, or other variations or shapes separated by spaces of non-conductive areas. Other patterns and shapes such as squares, rectangles, diamonds, and circular designs can be customized to accommodate needs. In some embodiments, the circuit setup for the conductive paths includes a pair of multiplexers (MUX), where the power signal is input into one (MUX) and the output signal is read from another MUX. Single and multiple combination of multiplexers can also be used.

Turning to FIG. 2D, in one embodiment for a two-dimensional plane, the first conductive path has a repeating spiral design to halve the amount of material being used. In some embodiments, the second conductive path also has a pattern design. In an example embodiment, to maximize the surface area of each contact point or sensor area, the second conductive path is provided as a continuous sheet. In another example embodiment, the second conductive path has a repeating square design, wherein each square unit of the repeating square design of the second conductive path overlaps with a spiral unit of the repeating spiral design of the first conductive path. In this manner, the total surface area of all the sensor areas is determined by the surface area of the spiral conductive path. A maximal signal is generated when there is 100% contact at all the sensor areas (and along the entire surface area of the spiral conductive path). Accordingly, when pressure/force is applied and the two conductive paths contact to complete the circuit, the output signal value reading is proportionate to the total surface area of the sensor area that is in contact.

In a three-dimensional plane, curvature and/or contours of the conductive paths and sensor areas are determinants of variations in the output signal value which would be distinguishable in three-dimensional space. For example, in an application of the flexible conductive apparatus as an artificial exterior skin layer for a robotic hand, positioning can be differentiable between a finger pointing straight or a finger being curled. The curvature at the tip of a finger would read a signal value that is different, thereby differentiating a pointing finger over a finger being curled. Another example application is visualization of three-dimensional mapping based on the amount of force/pressure applied on the sensor areas. As each sensor area can differentiate amount of force/pressure applied, a three-dimensional image can be outlined to demonstrate that an artificial exterior skin layer can determine where on a robotic hand an object exists in one example, and how heavy that object may be.

In accordance with general electrical circuitry, the flow of electrical charge has voltage that travels at a relatively quick speed as compared to the speed of light. Manipulation of design and the path of travel can alter the outcome of the speed of travel of electricity in a single circuit and create a delay in the path and slow down the speed of travel of electricity that is noticeable to the human eye. An example of the manipulation of design to alter the outcome of the speed of travel of electricity is that if a setup with only one point of contact for a sensor area 112 at which a connection would need to exist for electricity to travel to its destination, the speed of travel would be relatively fast as compared to the speed of light. Through manipulation of the design, an example requiring three points of contact 306 to make connection, a completed circuit with the electrical output signal will depend on the number of points being in contact. (See FIG. 3).

To further add to the manipulation in the time it takes for an electrical charge to reach its destination in a completed circuit, materials with varying levels of conductivity can also impact the speed of travel.

Sensor Areas

Each sensor area is unique at each intersecting or contact point. The signal generated by each sensor area can be manipulated by the applied force or pressure applied. By way of analogy, the location of an applied force or pressure on a weight scale will influence the weight reading. For example, standing on the edge of a weight scale will output a value different than standing in the center area of the weight scale. Increasing the surface area of each sensor area along with modifying the designs of the conductive paths will change the output value of the signal when a circuit completes (see Table 1 below). With the increased surface area of each sensor area acting similar to that of a weight scale, movement is detected by monitoring for variations in the output signals due to redistribution of applied pressure/force or contact over the sensor area. In contrast a stationary object will output a consistent signal value.

Hardware and Data Systems

In one example embodiment of a system, a flexible conductive apparatus 702 is attached to a hardware unit 704. The hardware unit has a receiver for receiving a signal from each sensor area, and a processor for processing the signals into pressure data. The pressure data is then stored and analyzed in a database network 706 and 708 each comprising one or more databases. An example system is illustrated in FIG. 7.

In some embodiments, the flexible conductive apparatus is connected to a hardware unit comprising components including a microcontroller, a single board computer that comprises of a wireless and wired network capabilities, a processor, multiplexers, analog-digital converters, amplifiers, alerting device, speakers, buzzers, LEDs/LED strips, accelerometer, gyroscope, or combinations thereof. The signals are read through a microcontroller and microprocessors and the signals are optionally amplified with amplifiers, resistors, and op amps that are converted to digital signals. The signals are optionally passed through a band-pass filter, filtering high frequency and low frequency signals.

In an example embodiment, the system has sensory feedback system. For example, the system may have lights and sound that is embedded for user interaction and communication of information (See FIG. 7). An example of such a sensory feedback system for user interaction may be an outcome 710 by way of example as an alarm that can be set in the event of a health related incident such as a fall, or a heart attack, or a stroke. Another example of an alternative outcome 712 may be for a baby that experiences apnea after X number of seconds of no movement, the device can activate an alarm. Outcomes may be customized to fit suitable applications as needed.

Sensory feedback is customizable to accommodate different conditions and the needs of the user receiving the feedback. The hardware unit may also optionally comprise of LED lights and speakers which can be activated to indicate and/or communicate different conditions of respiration, posture, location and movements. For example, breathing within a normal range can indicate a neutral color such as green, whereas a higher or lower than normal respiration rate can be orange or red to signal caution.

Figure 11:
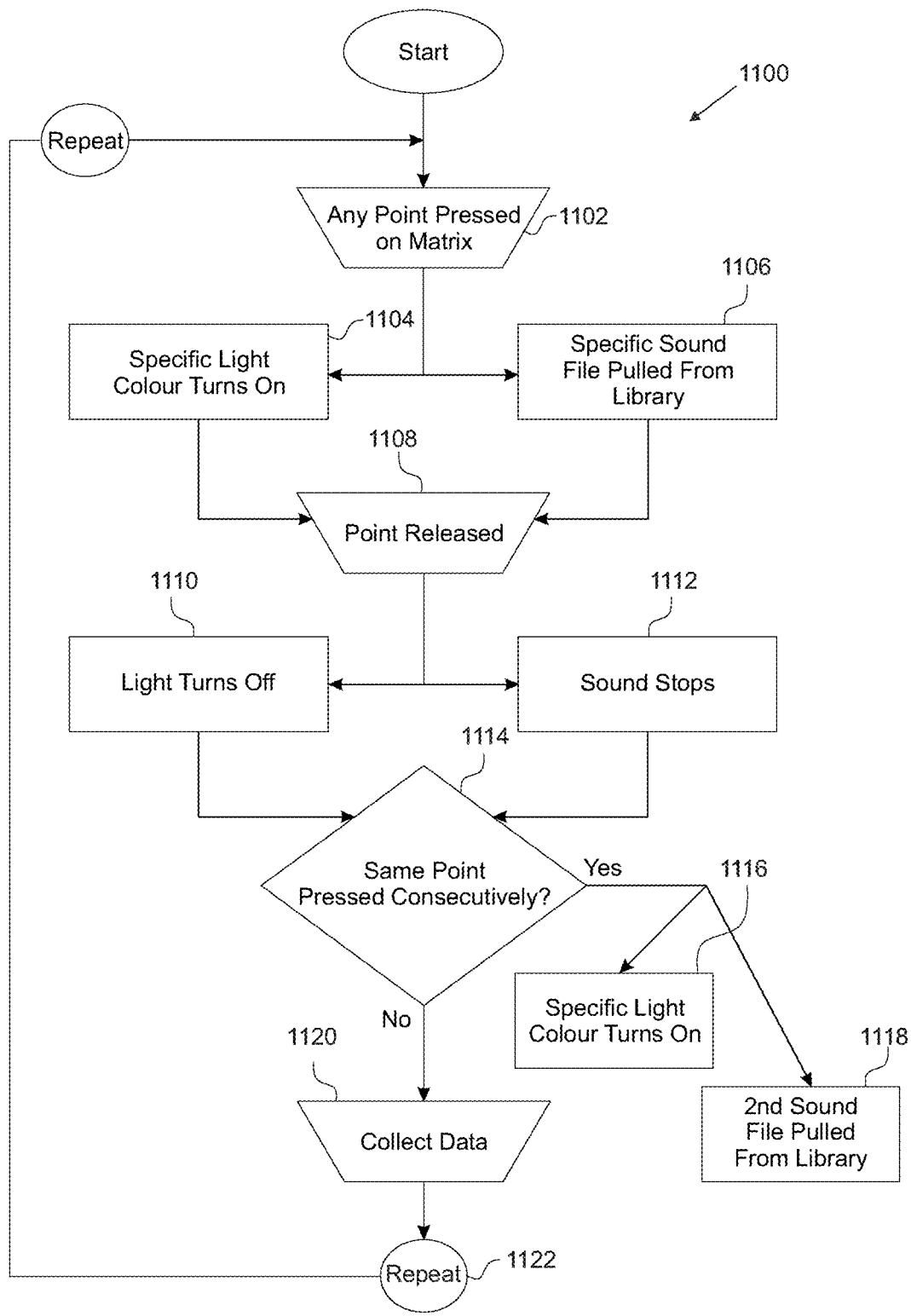
FIG. 11 shows a flow chart for an example sensory feedback system.

FIG. 11 illustrates an example flowchart 1100 of a method for a sensory feedback system with lights and sound using the flexible conductive apparatus 702 and system 700. As each sensor is unique and can measure variability of pressure applied, feedback through output devices that may include lights and/or sound can be set to have outcomes based on user interaction.

At event 1102, it is determined that any point is pressed on the matrix of the flexible conductive apparatus 702. An indicator is then output to an output device to signal to the user, for example event 1104 to turn specific light color on, and/or event 1106 to retrieve a specific sound file from library and output to a speaker. At event, it is determined that the point pressed on the matrix of the flexible conductive apparatus 702 is released. The corresponding light is turned off (event 1110) and/or the corresponding sound stops (event 1112). At event 1114, it is determined whether a same point on the matrix of the flexible conductive apparatus 702 is being pressed consecutively. If yes, then at event 1116 specific light colors turn on (can be different than the specific lights at event 1104) and/or at event 1118 a second sound file is pulled from the library and output to the speaker. If no, at event 1120 data is collected, and stored and/or sent to the database network 706, 708. At event 1122, the flowchart 1100 loops by repeating to event 1102.

In some embodiments, referring again to FIG. 7, the collection and transmission of pressure data to a data network is accomplished by a wired or wireless connection from the hardware unit 704 to the database network 706, 708. Wired or wireless networks can be more than one type of wireless networks (e.g., LAN, WLAN, radios, Bluetooth). Input values are classified by a timestamp, and the location (X, Y, and/or Z coordinates) by the receiver at each individual sensor area. For example, when contact input is generated at a sensor area, the varying value of that sensor is recorded as well as the time, location, and amount of force/pressure that was applied. In addition, user inputted data such as user information may be saved with the sensor information of the user (e.g., user's age and demographic information) to a database of the database network 706, 708. Data is stored into a database and can be hosted either locally or optionally also to a cloud server. Data from the database is used for multiple purposes, including for example: 1) Notification system for the detection of a set time duration of no change or change exceeding a set threshold of values that a sensor records, 2) Real-time feedback applications, and 3) Analysis of data from contact input for predictive models. All processed data are then stored into new databases and all databases are encrypted.

Raw inputs from the functional textile instrument can be grouped before entering the database to provide a faster collection of inputs. All incoming raw inputs can be set to specified ranges and the indicating pressure in terms of values (increasing or decreasing values) can be predetermined.

Raw data of electrical signals can be processed on the hardware unit 704 for Digital Signal Processing before data is stored to the database network 706, 708. This includes any error correction, to flag outliers, and using statistical calculations for signal processing.

In an example embodiment, error detection and outlier detection may be implemented. Error detection is determined if the incoming value per sensor is unchanged over time or if the values stay within a specified percentage of the total maximum value. Errors are determined if values fall outside a specified range of value and any irregular characters such as alpha and special characters that are created due to sampling from the microcontroller. For example, if the incoming values are set from 0 to 1024 and the incoming values occurs outside 0 or 1024, or wavers between 0-5 (approximately 0.5% of 1024), this is considered an error in the sensor in one example. The locations of the sensors are calibrated, thus, any errors in the sensors can indicate which location of the mat is disabled.

Outliers are determined by using techniques such as moving window, examining residuals to determine if values are greater than a specified interquartile range, or examining values greater than a specified threshold such as a specific standard deviation or using Fourier transforms and spectral density calculations.

Calibration and normalization can also be performed. Calibration is gathered within an initial time window (e.g., first 30 seconds) when no object or person is on the sensors by reading the raw signals. Using the raw signals collected for each sensor, a calibration technique is executed. One technique is to gather the maximum value, the minimum value, mean, standard errors to calculate a standardized score, and standardized residuals for each sensor. One technique for normalization is to calculate the maximum value, minimum value for each sensor during the time window and subtract the minimum value from each value and divide it by the range of the values within the time window. This will turn each sensor value between the range of 0 and 1.

Classification of Movement and No Movement

Returning to FIG. 6A, presence or absence of movement is determined using the electrical signals collected from the flexible conductive apparatus 702. This example embodiment will illustrate detection of movement and no movement of a living being using the flexible conductive apparatus 702.

Step (1) A detection of "contact" versus "no contact". For example, one technique is based on a calculation of meeting an absolute threshold across all sensor areas and meeting a difference threshold that examine a change in values for each sensor area. The first few hundreds of values are calculated to give an initial mean, median, and an initial variation threshold. After, the past (x−1) and current values (x) are always compared for each sensor area. For each sensor area, rolling means and rolling standard deviations are taken for every interval of a specified amount of seconds. If the value is less than a predetermined mean threshold (e.g., <100), it is considered "no contact". If the incoming value is greater than the difference threshold for that sensor and the value is greater than the mean threshold, then the value is considered "contact". Transformations and baseline calibrations (e.g., subtracting the variations of the first hundreds of values when there is no contact) may also be applied to all incoming signals to reduce the "noise" of incoming signals. Other techniques include Fourier Transforms and Power Spectral Density which are also performed for all sensors signals, breaking down the signals into sinusoids functions. The sinusoid function for each sensor is then compared relative to the other corresponding sensors. The ones with the largest or most peak amplitudes in specified frequencies will also indicate when there is contact. An average of all Fourier Transforms for each sensor is integrated to produce one signal per point in time. Transformations to the signals allows amplification of the signals to provide better distinctions of the signals.

Step (2) All the "contact" sensor areas per given time is categorized and divided into multiple regions. A concentrated region, for example, includes the torso area where breathing movement is captured or the region that provides stronger indicating output signals. After examining the mean and the variation of each sensor area over time, sensor areas with the lowest mean, median, and residuals as well as the least variation is determined. Sensor areas with the greatest mean and the most variation are also determined. Area about these identified sensors may additionally be mapped onto a graphical representation, for example a heat map to determine the locations of interest. The greatest variation is considered to be characterization of movement and the least variation is considered to be closer to no movement. In addition, specific frequencies can be specified for respiration and other vital signs such as heart rate with calculations using Fourier Transforms, power spectral density calculations, correlation methods, autoregressive models, power spectral density, and cluster analysis which can determine regions of interest.

Step (3) A target area is highlighted to monitor movement. Importantly, a detection of movement is determined in comparison to readings where there is no movement. The mean and variation is calculated for movement vs. no movement. When there is no movement, the variation threshold is smaller than when there is movement. Optionally, the target area is also mapped by sensor locations and the use of regression models and machine learning models to determine the breathing activity. Frequency for respiration and movements are also different and can be specified to give insights on movements as well.

Timer/Alarm System

In some example embodiments, the system may additionally comprise a timer system for initiating a visual or auditory notification based on a predetermined set of parameters. For example, a timer and alarm system, where an alarm is sounded after a detection of a specified number of seconds of no movement. For detecting an absence of movement, several procedures are considered. Or in another example, an alarm is sounded after a detection of signals above or below a set range of parameters, equating to a determined amount of force/pressure applied. For example, in a compression instrument where a set amount of pressure must be maintained to stop traumatic bleeding, muscular tendencies may constrict over time and an alarm can sound to notify if retightening of the compressing instrument is needed to prevent venous and/or arterial bleeding. A timer may also sound if the compressing instrument had been applied for a prolonged period of time to notify and prevent risk of permanent damage.

When all sensor areas corresponding to the target area display no movement, that is, with minimal variation of the values over a specified predetermined interval, an auditory and/or visual alarm may sound. The minimal variation over the specified interval across sensor areas in the target area will send a signal to the hardware device and triggers an auditory sound and/or a visual alarm on the monitor of an application. This checking of minimal variation is done for each iteration. A timer is set at a specified amount of seconds for each iteration.

Device Compatibility

The system is compatible for the use in both browser and mobile devices. A real time monitoring application interface may provide information and graphical representations about the user, the conditions, timer, the alarm, the breathing rate, the breathing analysis, pressure applied, lack of required pressure, or any such variation that can detect variation through contact input. The interface also allows users to input user information which will be linked to the sensor information output from the hardware. This real-time monitoring application interface will be retrieving information from the database network.

Detection of Object Versus Humans

Means, variations, frequencies of signals are determined over time whether there is a significant change. If values of the "contact" sensors show no change or minimal variation over time and if the raw input values are within a small range, then this triggers the possibility of a still object.

The following examples are further illustrative of various aspects of example embodiments.

The flexible conductive apparatus 702 can be made using various combinations of materials with different combinations of conductive properties depending on the desired level of sensitivity from the hardware component alone.

A 5 volt power source is attached to the flexible conductive apparatus 702, recording output values in a range in one example, from 0-1024 based on measuring the maximum threshold values from a completed circuit with the same amount of force/pressure applied. Different materials will output a different maximum threshold based on the amount of force/pressure, where a high conductive material will reach a maximum threshold that is higher than materials with lower levels of conductivity (see Table 1 below). As threshold values differ by using different material combinations and amount of force/pressure applied, sensitivity can also be adjusted by using the improved 2 layer system rather than the 3 layer system.

As thresholds will not reach a maximum value (e.g. 1024) based on 5V input due to natural resistive elements of current carrying conductors, order and combinations of materials may create time differences for completion of a circuit.

TABLE 1

Material Testing: output value range from 0-1024, 5 V power source

Material List

| | |
|---|---|
| O = | Original Material, Conductive Fabric, 1 sided |
| M = | Resistive Mesh Layer |
| V = | Resistive Plastic Type Layer |
| G = | Green Conductive Fabric, 2 sided |
| S = | Silver Conductive Fabric, 1 sided |

| | Range From: | Maximum Threshold |
|---|---|---|
| Combination: 3 Layer | | |
| O - G - O | 230 | 825 |
| O - V - O | 40 | 823 |
| O - M - O | 8 | 800 |
| S - G - S | 80 | 640 |
| S - V - S | 3 | 370 |
| S - M - S | | 440 |
| G - V - G | 35 | 520 |
| G - M - G | 4 | 410 |
| Combination: 2 Layer | | |
| O - O | | 823 |
| O - G | 300 | 710 |
| S - O | 350 | 680 |
| S - S | 33 | 283 |
| S - G | — | 410 |
| G - G | 292 | 463 |

Conductive Path Designs

Example Design 1: an example of a flexible conductive apparatus setup for a system to detect pressure for a flat, non-compressible surface is a two-layer design with the conductive textile that combines conductive and non-conductive threads that are "weaved/knitted" in a grid-like pattern where non-conductive threads provide separation from the conductive threads, where a first conductive path 302 is set up to run in one direction and a second conductive path is set up to run in an intersecting direction 304, thereby when the two conductive paths are overlaid, a grid pattern results with each intersecting point forming a sensor area 112 that can measure variability based on a first level of resistance of non-conductive threads separating the first and second layers, and the second level of resistance from the non-conductive threads separating the conductive threads on the same layer. As there is separation from the conductive threads, applied pressure from external forces will compress the two layers making contact of the intersecting conductive paths at different points 306 allowing variability of electrical signals to be measured correlating to the amount of pressure applied.

Example Design 2: an example embodiment of a flexible conductive apparatus setup for a system to detect pressure for a surface with changing form factors by way of example as a bed, is a three-layer design with first and second conductive paths 504 and 508 separated by a middle layer 506. The middle layer provides resistance through dispersion from the first and second conductive paths 504 and 508 coming fully into contact for situations such as if portions of the flexible conductive apparatus is bunched closely.

Example Design 3: A third example is where one layer has a spiral design 204 that creates gaps for lower surface area conductivity. The opposing layer 200 would have higher surface area conductivity to eliminate gaps so that variation can be determined from points coming into contact. If the example described were flipped, a small point of contact made at an area where there is a gap may not read an output value similar to the previously demonstrated example.

Example Design 4: A fourth example includes an efficient method for using less materials by combining conductive fabric and thread: an example being a 1.27 cm (0.5 inch) conductive fabric 212 and a conductive thread 214 that are connected in a pattern that would increase the surface area equivalent to a 2.54 cm (1.0 inch) conductive fabric, but using less material (e.g., see FIGS. 2E and 2F).

Figure 12:
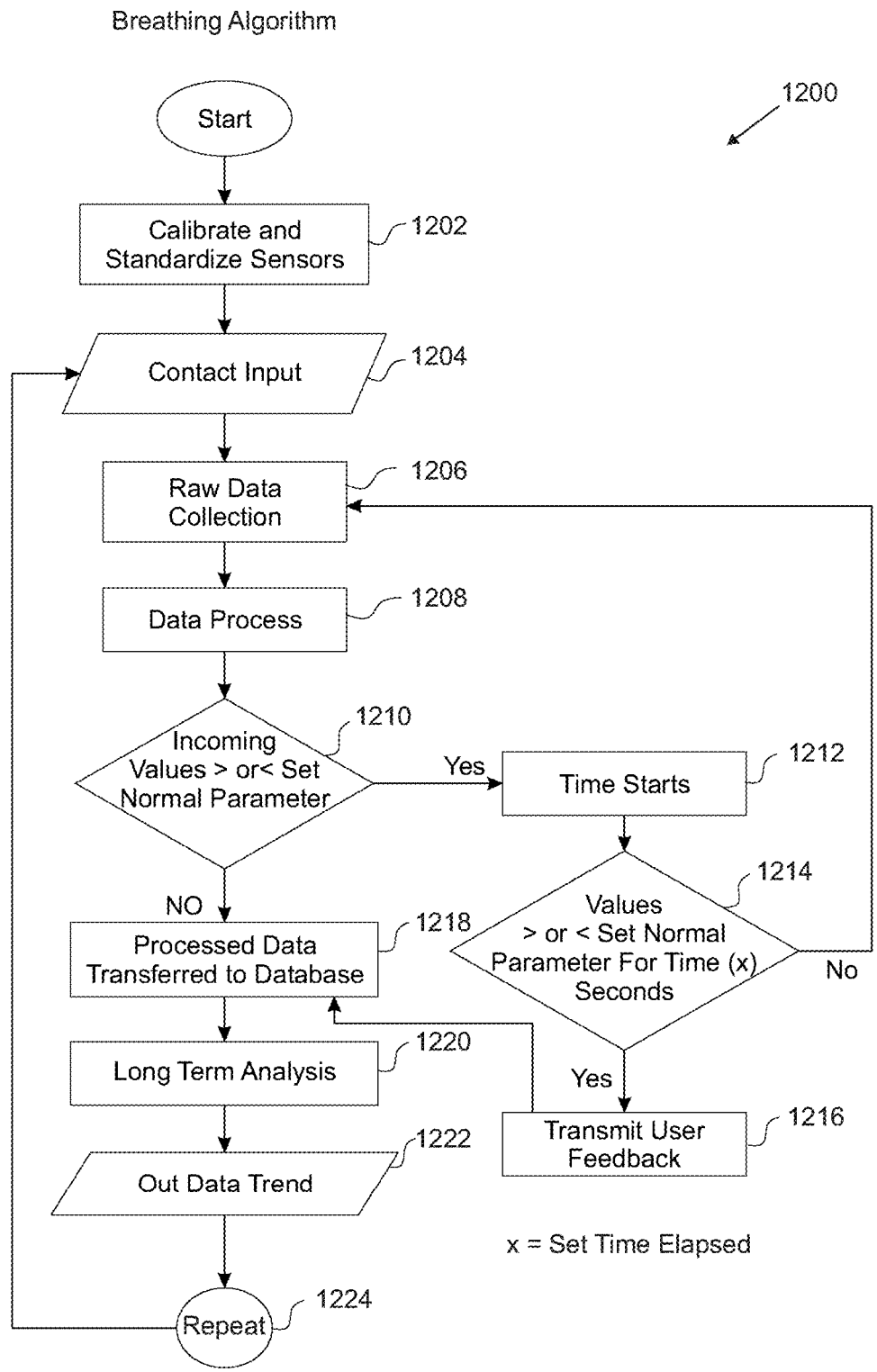
FIG. 12 shows a flow chart for an example breathing monitoring algorithm.

FIG. 12 illustrates a flowchart 1200 of an algorithm for breathing analysis and detecting conditions outside of normal set parameters, using the flexible conductive apparatus 702 and system 700 in an example embodiment. The torso is highlighted (see FIG. 6C) as a target area to monitor breathing activity in comparison to readings where there is no breathing. After errors and outliers are determined and excluded from analysis of breathing, torso regional areas are determined. Variations are calculated for breathing versus no breathing. Fourier Transforms are also conducted for each signal for all sensor points in an example embodiment.

At event 1202, the sensors of each of the flexible conductive apparatus 702 are calibrated and standardized. For example, a baseline signal can be determined when no object or external pressure is present on the flexible conductive apparatus 702. At event 1204, there is contact input detected one or more of the sensors of the flexible conductive apparatus 702. At event 1206, raw data is collected from the sensors of the flexible conductive apparatus 702. At event 1208, the raw data is processed. At event 1210, it is determined whether incoming values are greater or less than a set normal parameter. If yes, then at event 1212 a time starts. Further, at event 1214 it is determined whether the values are greater or less than the set normal parameter for a specified period, e.g. number of seconds. If not, the method loops to event 1206. Referring again to event 1214, if yes then at event 1216 there is transmitted user feedback to an output device such as a speaker, light or visual display, and then data proceeds to event 1218. All events are captured into the database network 706, 708, in an example embodiment.

Referring again to event 1210, if no then at event 1218 the processed data is transferred to a database network 706, 708. At event 1220, there is performed long-term analysis that can be based on the present patient subject, historical information, other patients, big data, etc. at event 1222, long term data trend is output. In an example embodiment, Long Term Analysis data may also be captured in the database network 706, 708. At event 1224, the flowchart 1200 loops by repeating to event 1204.

Figure 13:
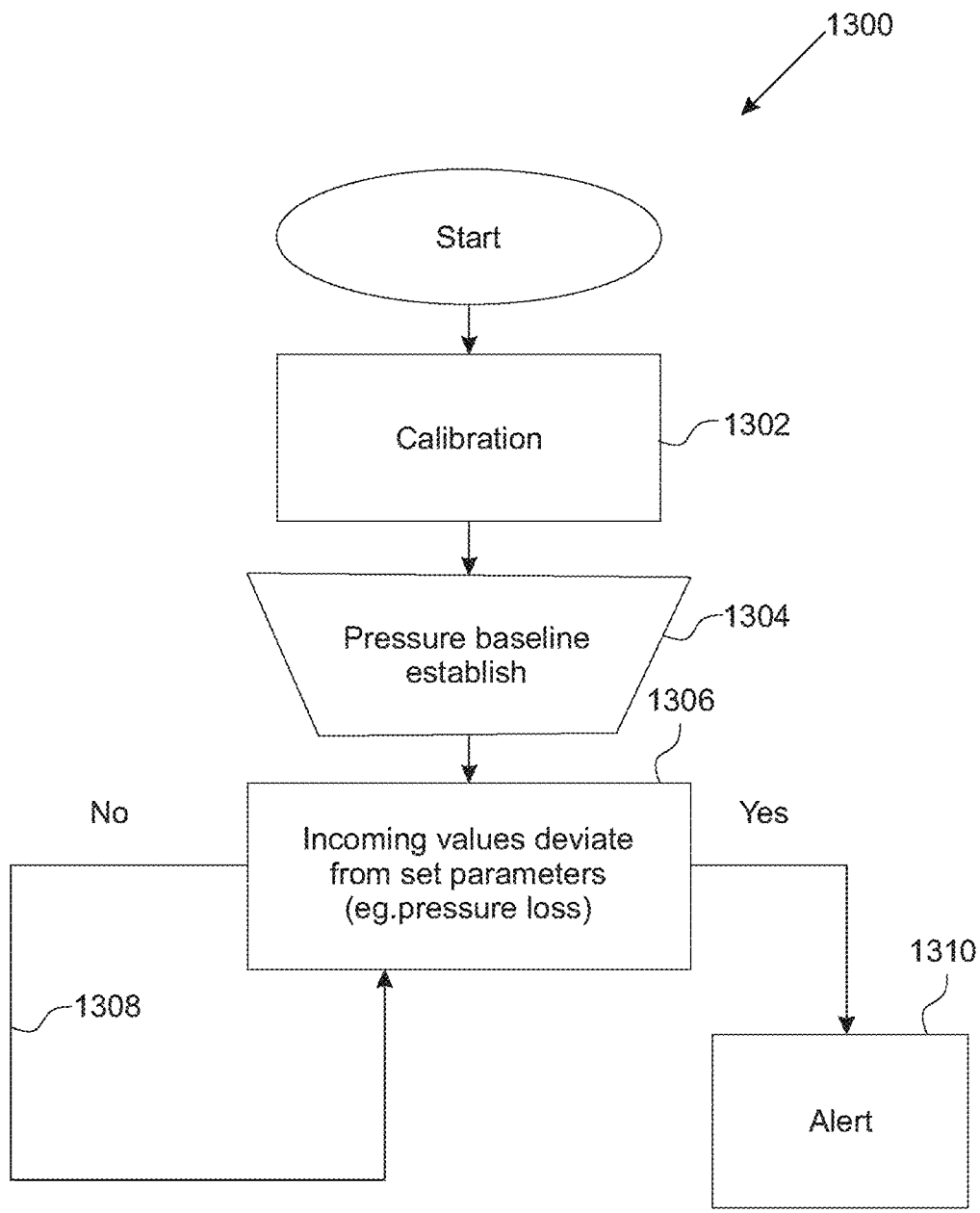
FIG. 13 shows a flow chart for an example system of monitoring pressure loss.

FIG. 13 illustrates a flowchart 1300 of an algorithm for monitoring of pressure using the flexible conductive apparatus system 700 attached to a combat application tourniquet. At event 1302, the system 700 once activated is configured to calibrate to the according pressure level as set by the applicator or through an automated setting of establishing a baseline for the pressure applied at event 1304. At event 1306, it is determined whether incoming values deviate from set parameters, e.g. pressure loss. If so, at event 1310 the system 700 can be configured to alert through an output device if there is a loss in pressure of the tourniquet until correct pressure levels are achieved again. If not, then at event 1308 the flowchart 1300 loops by repeating event 1306.

Figure 14A:
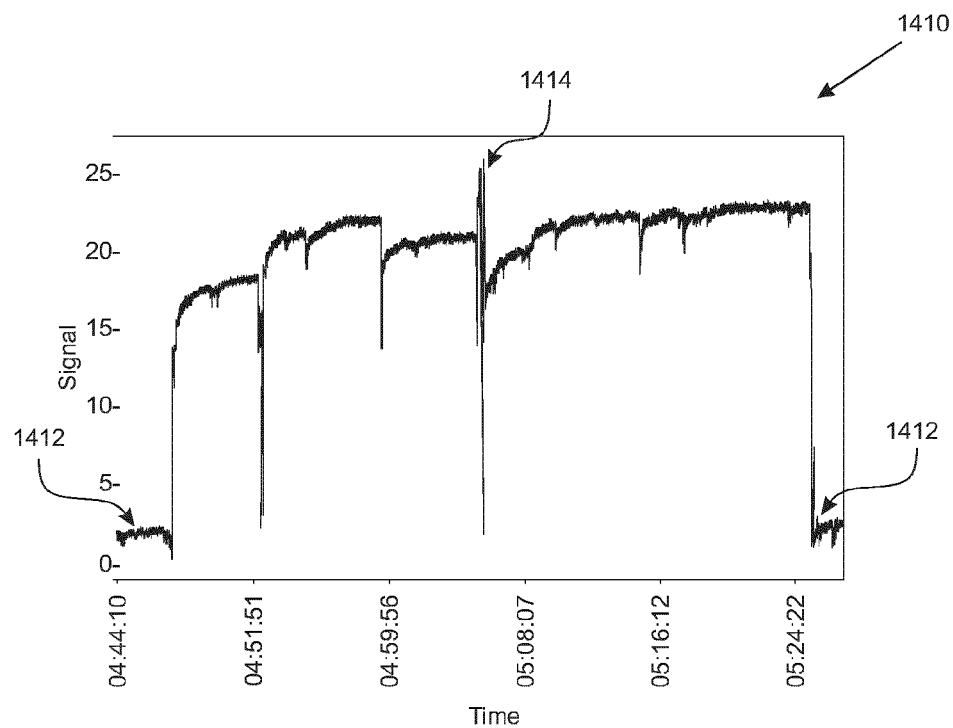
FIGS. 14A and 14B shows experimental results for monitoring breathing patterns using an example embodiment of a flexible conductive apparatus on humans.
Figure 14B:
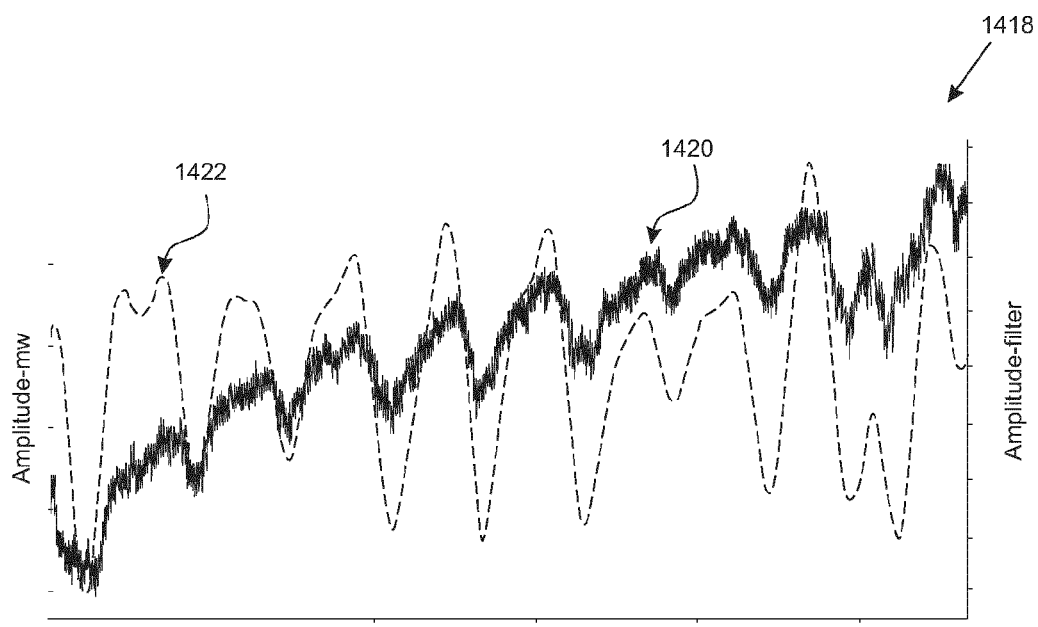

FIGS. 14A and 14B illustrate further results of electrical signals derived from experimental controlled settings that are translated into activity monitoring graph 1410 and respiration graph 1418. Illustrated in FIG. 14A is a monitoring graph 1410 that depicts activity prior to and following when there is an object on the flexible conductive apparatus indicated by signal 1412, and a spike in the signal 1414 indicating sudden movement resulting from a sneeze. Coughs may be determined by example through spikes in the signal that are greater than normalized settings, and less than the large spike 1414 resulting from a sneeze, occurring with higher frequency. Illustrated in FIG. 14B is a graph 1418 that depicts the respiration pattern of the person in the same experimental controlled setting of results from FIG. 14B. The raw signals are shown on the line graph 1420, with filtered and processed signals being shown on line graph 1422.

Figure 15A:
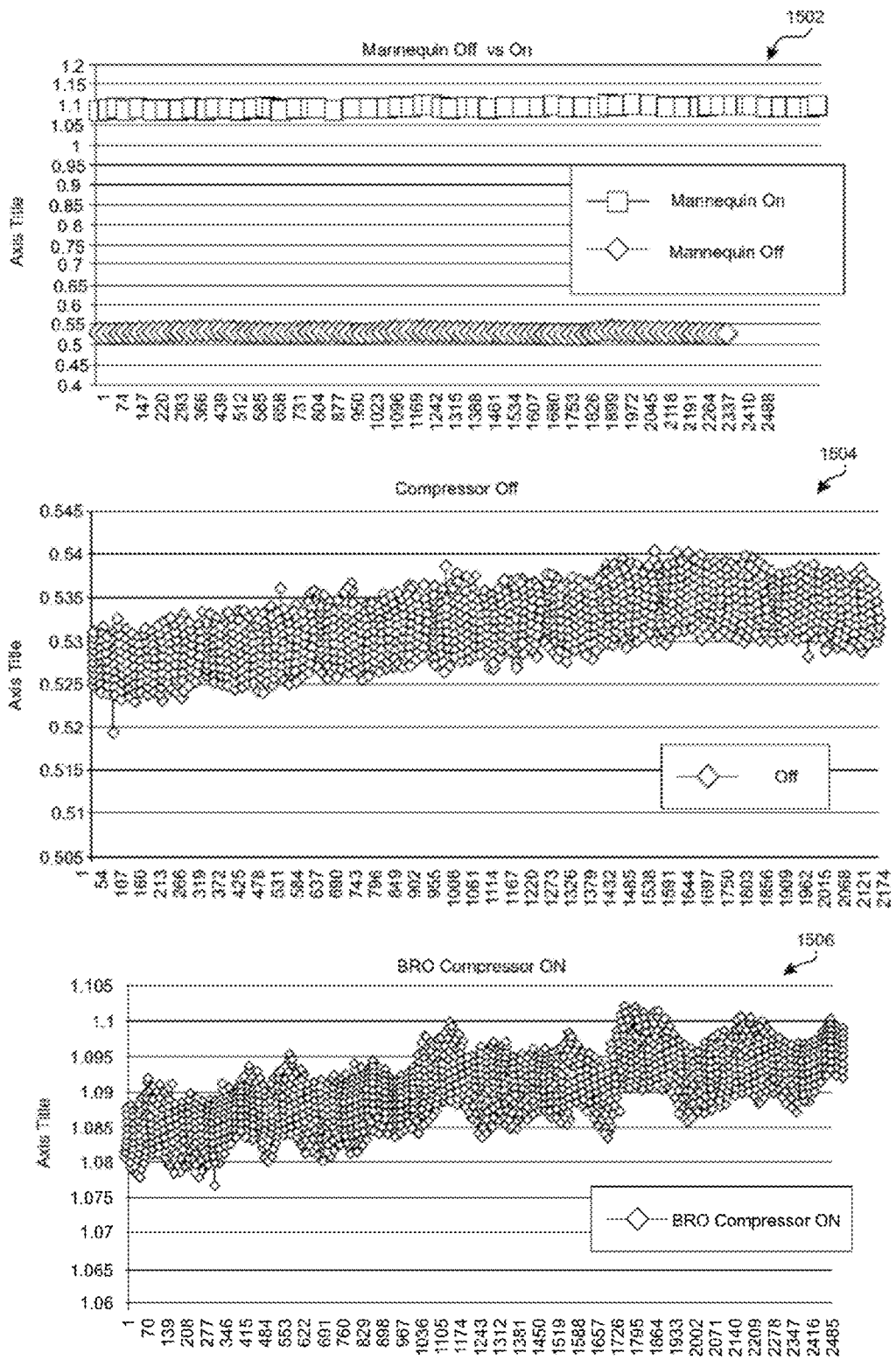
FIGS. 15A and 15B shows another set of experimental results in a clinically controlled setting for monitoring breathing patterns using an example embodiment of a flexible conductive apparatus using high technology mannequins.
Figure 15B:
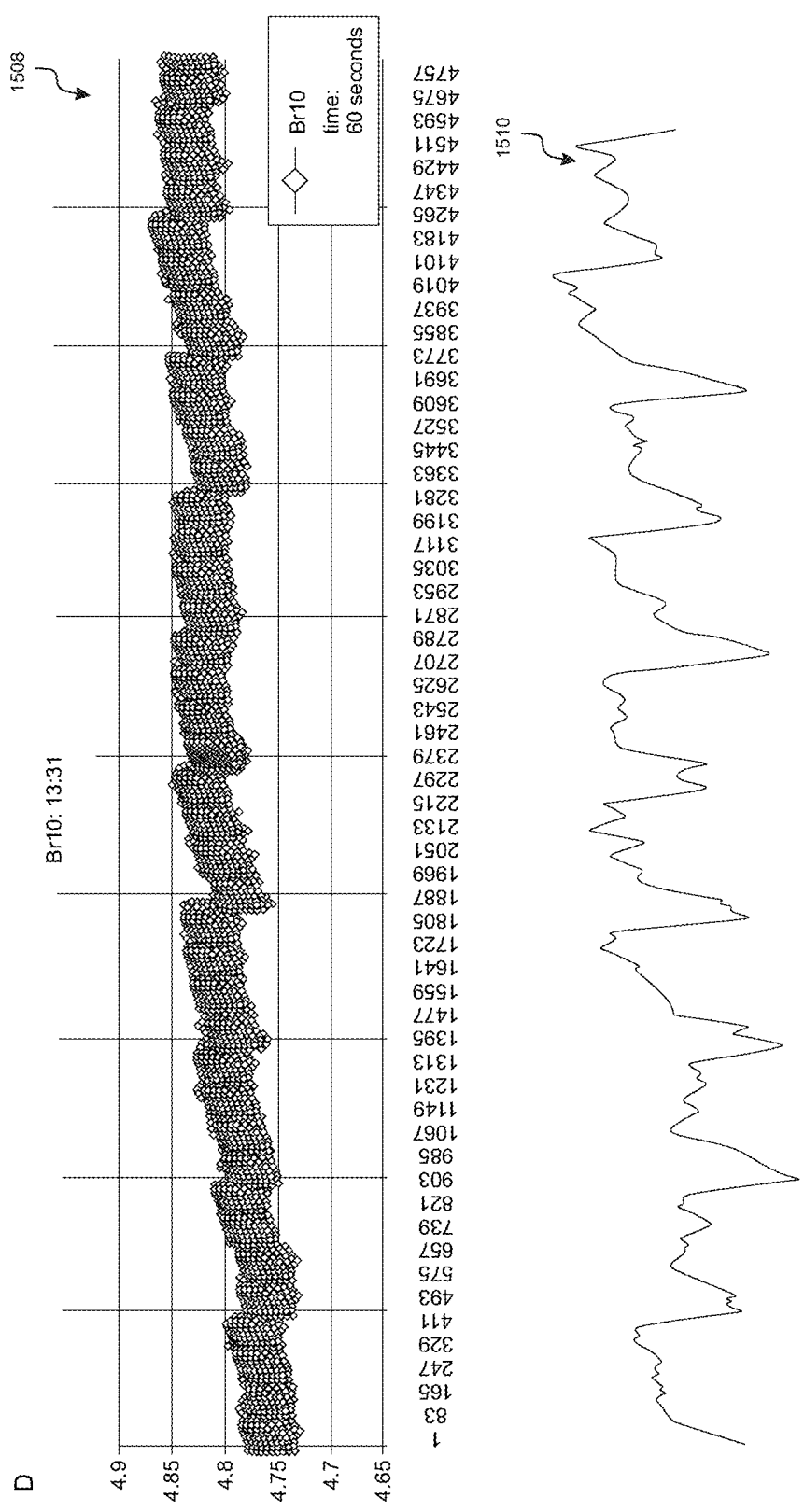

FIGS. 15A and 15B shows another set of experimental results in a clinically controlled setting for monitoring breathing patterns using an example embodiment of a flexible conductive apparatus, illustrating readings or signal values over time. Breathing patterns were simulated using a high technology mannequin with artificial lungs that are inflated by an air compressor, at breath rate zero ("BR0"). Comparison of baseline readings when there was no object versus when there was a mannequin placed on the flexible conductive apparatus is illustrated in graph 1502. Baseline readings of when the air compressor is turned off is illustrated in graph 1504. Baseline readings of when the air compressor is turned on but all vital signs are set to 0 are illustrated in graph 1506 while showing detection of slight vibrations from the air compressor that controls the high technology mannequin. The motor of the air compressor was located on the floor a distance away from the sensors, illustrating the sensitivity of flexible conductive apparatus.

Turning to FIG. 15B is a graph 1508 of another set of experimental results using a mannequin with artificial lungs to simulate breathing, breath rate ten ("BR10"). The volume of air inside the artificial lungs are controlled using an air compressor, which inflates and deflates the artificial lungs to simulate breathing. Illustrated are results from when the air compressor is turned on and simulated breathing is set to 10 breaths per minute in the graph 1508. Illustrated are additional results from when the air compressor is turned on and simulated breathing is set to 10 breaths per minute in signal 1510.

Figure 16A:
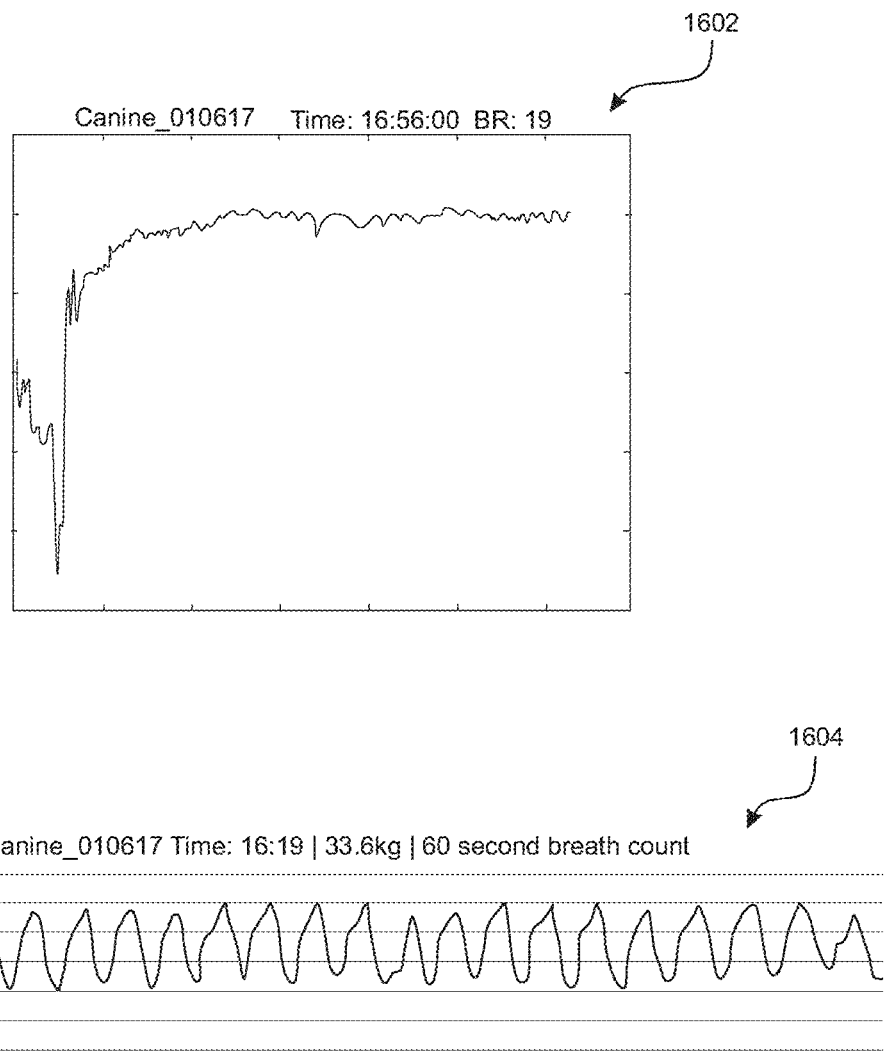
FIGS. 16A and 16B shows another set of experimental results of a controlled test of vital signs for a canine diagnosed with lymphoma.
Figure 16B:
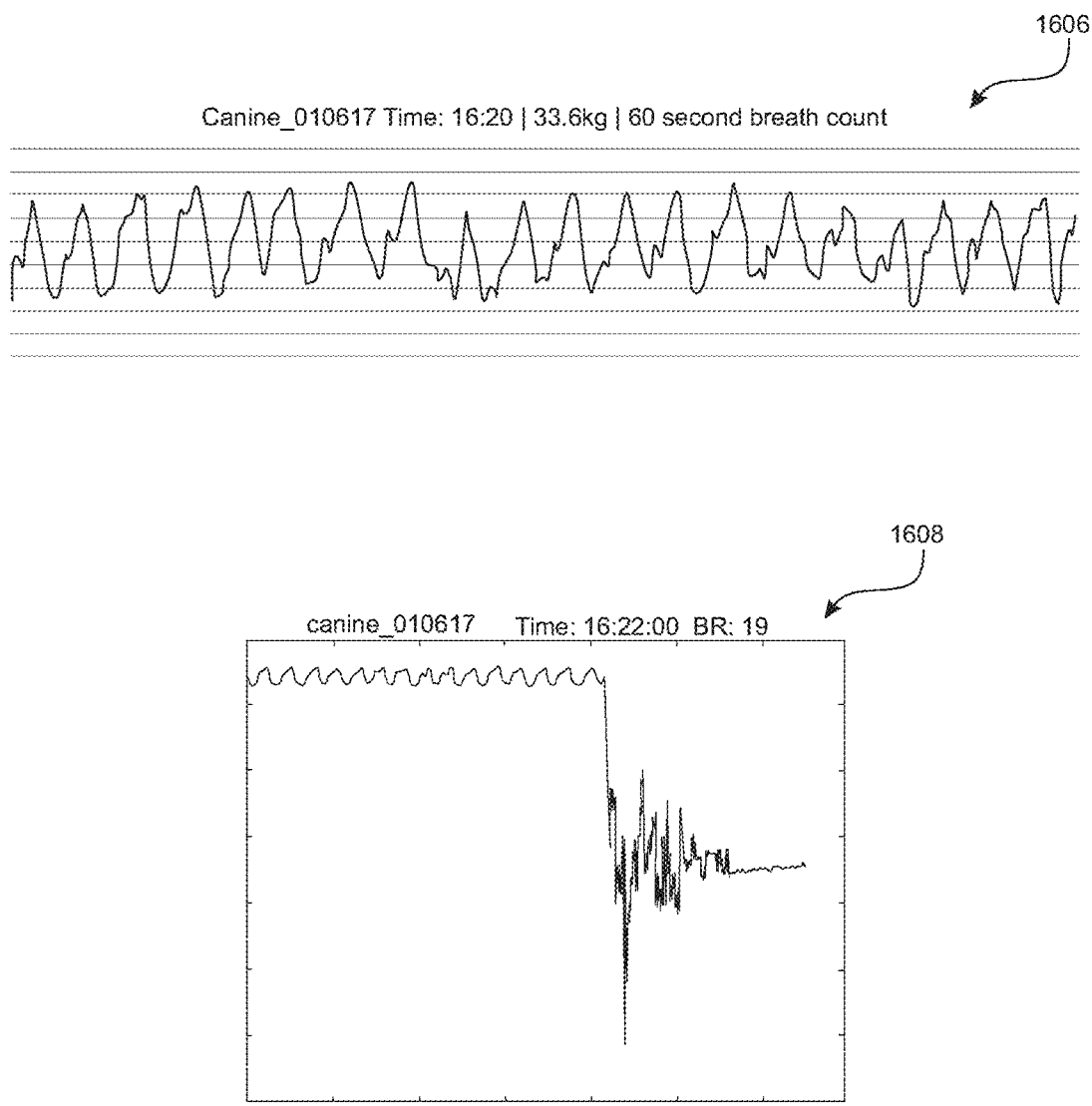

FIG. 16A shows a controlled test of vital signs for a canine diagnosed with lymphoma, at breath rate nineteen ("BR: 19"). Illustrated is a graph 1602 of signal values over time that depicts activity of the canine in the graph 1602 under controlled conditions from initially setting down on the flexible conductive apparatus in one embodiment, where the said apparatus determines the initial change from no object being detected to presence of an object being detected, then begins showing physiological signals after the canine lays down on the said apparatus. Illustrated is a graph 1604 of signal values over time showing the same canine with occasional respiratory difficulties with a recorded manual count of breaths for the first 60 seconds with relatively stable respiration patterns. FIG. 16B shows the same canine following 60 seconds showing irregular respiration patterns in graph 1606 including segments with multiple attempts of inhalation for a full cycle of breath at changing intervals. Breath rate is 22 ("BR: 22"). Illustrated further is a graph that depicts activity of the canine in graph 1608 under controlled conditions leading up to, and getting up and off the flexible conductive apparatus.

Similar analysis and/or methods can be applied to monitoring and detecting heart rate and temperature, in example embodiments.

An example embodiment is variable conductive apparatus responsive to applied external force, comprising: a first conductive path that includes a first conductive surface; a second conductive path that includes a second conductive surface, a part of the second conductive surface having a conductive contact surface area with a part of the first conductive surface when there is no applied external force, another part of the second conductive surface separate from another part of the first conductive surface when there is no applied external force, wherein the applied external force increases the conductive contact surface area between the first conductive surface and the second conductive surface resulting in an increase in conductivity between the first conductive surface and the second conductive surface.

In an example embodiment of any of the above described variable conductive apparatus, wherein the first conductive path is for receiving power from a power supply, and the second conductive path results in a detectable signal in dependence of the conductivity.

In an example embodiment of any of the above described variable conductive apparatus, wherein the received power is a DC voltage.

In an example embodiment of any of the above described variable conductive apparatus, wherein the detectable signal is less than a maximum signal defined by the power supply when there is no applied external force.

In an example embodiment of any of the above described variable conductive apparatus, wherein the detectable signal increases in correlation to the applied external force due to the increase in the conductivity.

In an example embodiment of any of the above described variable conductive apparatus, wherein the detectable signal is a maximum signal defined by the power supply when there is applied external force that maximizes the conductive contact surface area, resulting in maximized conductivity.

In an example embodiment of any of the above described variable conductive apparatus, further comprising the power supply.

In an example embodiment of any of the above described variable conductive apparatus, further comprising a detector for detecting the detected signal.

In an example embodiment of any of the above described variable conductive apparatus, further comprising at least one layer to separate at least part of the first conductive surface and the second conductive surface.

In an example embodiment of any of the above described variable conductive apparatus, wherein the at least one layer comprises conductive threads that provide additional contact surface area for the conductive contact surface area.

In an example embodiment of any of the above described variable conductive apparatus, wherein the at least one layer further comprises non-conductive threads.

In an example embodiment of any of the above described variable conductive apparatus, wherein the at least one layer comprises an insulating layer.

In an example embodiment of any of the above described variable conductive apparatus, wherein the insulating layer comprises air.

In an example embodiment of any of the above described variable conductive apparatus, wherein the at least one layer comprises a compressible layer.

In an example embodiment of any of the above described variable conductive apparatus, further comprising a support layer to receive the applied external force and to support the first conductive path or the second conductive path, wherein the first support layer comprises at least one rigid layer.

In an example embodiment of any of the above described variable conductive apparatus, wherein the increase in conductive contact surface area comprises additional contact points between the first conductive surface and the second conductive surface.

In an example embodiment of any of the above described variable conductive apparatus, wherein the increase in conductive contact surface area comprises an increase in contact surface area of an existing conductive contact point that exists when there is no applied external force.

In an example embodiment of any of the above described variable conductive apparatus, wherein the applied external force reduces a distance between the another part of the first conductive surface and the another part of the second conductive surface.

In an example embodiment of any of the above described variable conductive apparatus, wherein the conductive contact surface area increases in correlation to the applied external force, resulting in the increase in the conductivity.

In an example embodiment of any of the above described variable conductive apparatus, wherein the first conductive path comprises a material having a first conductivity, wherein the second conductive path comprises a material having a second conductivity that is different than the first conductivity.

In an example embodiment of any of the above described variable conductive apparatus, wherein the first conductive path is generally perpendicular to the second conductive path, and the first and second conductive paths overlap in a grid-like pattern.

In an example embodiment of any of the above described variable conductive apparatus, wherein at least one of the first conductive path or the second conductive path is in a spiral pattern.

In an example embodiment of any of the above described variable conductive apparatus, wherein the applied external force increases conductive contact surface area between the another part of the first conductive surface and the another part of the second conductive surface.

In an example embodiment of any of the above described variable conductive apparatus, wherein the applied force comprises vibration.

In an example embodiment of any of the above described variable conductive apparatus, wherein the first conductive path and the second conductive path are comprised of conductive fabrics and/or threads.

An example embodiment is a sensor sheet comprising one or more layers and a plurality of sensors, each of the sensors comprising any of the above described variable conductive; a power supply for providing power to the first conductive paths; and a detector for detecting a detectable signal from the second conductive paths in dependence of the conductivity of the variable conductive apparatuses.

In an example embodiment of any of the above described sensor sheet, wherein each sensor shares the respective first conductive path with the first conductive path of at least one of the other sensors, and wherein each sensor shares the respective second conductive path with the second conductive path of different at least one of the other sensors, wherein power is selectively activatable to each of the first conductive paths one at a time, and a detectable signal from one or more of the second conductive paths results in knowledge of which of the sensors is receiving the applied external force.

In an example embodiment of any of the above described sensor sheet, wherein the sensors are arranged in an array.

In an example embodiment of any of the above described sensor sheet, wherein the first conductive paths of the sensors are arranged in columns and the second conductive paths of the sensors are arranged in rows, wherein power is selectively activatable to each of the first conductive paths one at a time, and a detectable signal from one or more of the second conductive paths results in knowledge of which of the sensors is receiving the applied external force.

In an example embodiment of any of the above described sensor sheet, wherein the at least one layer comprises at least one flexible layer.

In an example embodiment of any of the above described sensor sheet, wherein the at least one layer comprises at least one rigid layer.

Another example embodiment is a variable pressure sensor comprising any of the above described variable conductive apparatus; a power supply for providing power to the first conductive paths; and a detector for detecting a detectable signal from the second conductive paths in dependence of the conductivity of the variable conductive apparatuses.

Another example embodiment is printed circuit board or microchip comprising any of the above described variable conductive apparatus, the printed circuit board or microchip configured to perform digital communication over the variable conductive apparatus over greater than two signal states due to dynamic range of the conductivity of the variable conductive apparatus.

Another example embodiment is a system for monitoring external force comprising: a power supply; one or more variable pressure sensors, each comprising any of the above described variable conductive apparatus for receiving power from the power supply; a detector for detecting a detectable signal from the variable conductive apparatuses in dependence of the conductivity of the variable conductive apparatuses; a processor for processing the detectable signal into external force data, and for sending the external force data to a database or a server for storing and analyzing of the external force data; and an output device controlled by the processor to communicate an output in response to the detectable signal or the analyzed external force data.

In an example embodiment of any of the above described system, further comprising a microcontroller, a single board computer that includes a wireless and wired network capabilities, one or more multiplexers, one or more analog-digital converters, one or more amplifiers, an alerting device, one or more speakers, one or more buzzers, one or more LEDs, one or more LED strips, or a combination or a subcombination thereof.

In an example embodiment of any of the above described system, wherein the output device further comprises a sensory feedback system for user interaction through the output device.

In an example embodiment of any of the above described system, wherein the sensory feedback system comprises an alarm for alerting incidents.

In an example embodiment of any of the above described system, wherein the database is part of a cloud server.

In an example embodiment of any of the above described system, further comprising a timer system for initiating a notification based on a predetermined set of parameters.

In an example embodiment of any of the above described system, wherein the database further comprises a processor for analyzing the external force data.

Another example embodiment is a method of monitoring movement using any of the above described system, the method comprising: determining a baseline external force value when there is no external force applied to the variable conductive apparatus; obtaining signals having values above the baseline external force value; calculating differences between the obtained signals and the baseline external force value; and identifying one or more signals having differences greater than a difference threshold; outputting information to the output device based on said identifying when the one or more signals having differences greater than the difference threshold.

In an example embodiment of any of the above described method, wherein the baseline external force value is an average value.

In an example embodiment of any of the above described method, wherein the baseline external force value is a respective value for each variable pressure sensor.

An example embodiment is a use of any of the above described system for monitoring breathing of a subject, for monitoring heart rate of a subject, for monitoring movement of a subject, for monitoring and tracking location of a subject, or for monitoring pressure level in a compression instrument.

An example embodiment is a use of any of the above described system for monitoring pressure level in a compression instrument tourniquet.

An example embodiment is a use of any of the above described system in a shelf for monitoring inventory levels.

An example embodiment is a use of any of the above described system in artificial exterior skin for providing a sense of touch to a robotic component.

Some embodiments include a projected dielectric sensor with a first conductive path including a first conductive mesh (e.g., first conductive fabric), a second conductive path including a second conductive mesh (e.g., second conductive fabric), and a dielectric gap (e.g., air or fabric) between the first and second conductive paths. A power drive may be connected to the first conductive path, and a collector may be connected to the second conductive path. Conventional capacitive sensors include conductive paths that are arranged on a Y-plane (e.g., top and bottom, transverse, Y1, X1). The present system includes conductive paths that are positioned on the same X-plane (e.g., side-by-side, longitudinal, X1, X2). This configuration allows for improved detection capabilities. This alignment may enhance sensitivity and reduce manufacturing complexity. It would still be possible to include a sensor where the conductive paths are arranged on a Y-plane. Some embodiments may include the use of multiple sensors arranged in a network, these sensors may be all Y-plane, all X-plane, or a combination of the two types of orientations.

Some embodiments may feature a dielectric gap in the projected dielectric sensor as an open circuit when in a resting state. In some embodiments, the gap may be significantly larger compared to traditional capacitive sensors, providing a broader detection range. This design may enable the sensor to detect objects (e.g., conductors, vehicles, humans, baby seats) that are off-axis to the dielectric gap, enhancing its versatility in various applications. This feature may be particularly useful for applications requiring wide-area detection.

Some embodiments include a projected dielectric sensor offering extensive capabilities in various fields. In vehicle applications, the sensor may detect the presence and position of occupants, monitor baby seats, and provide advanced gesture and mid-air control for interior controls and vehicle mobility. Biometric applications may leverage the sensor for shape detection and proximity detection, functioning similarly to radar systems. The system may also include gesture and mid-air control for social interactions, allowing intuitive control of devices and environments based on user movements.

The projected dielectric sensor's capabilities may allow the sensor to be applied across a wide range of applications, enhancing its versatility and functionality. In automotive settings, the sensor may be used to monitor the presence and position of occupants, including passengers and baby seats. Some embodiments can detect off-axis objects, such as a vehicle or a human, enhancing safety features like collision avoidance systems and occupant detection. This sensor may also facilitate gesture and mid-air control for interior vehicle controls, allowing drivers and passengers to adjust settings like temperature, audio, and navigation through simple hand movements. This may promote safer, hands-free operation, improving overall driving experience and safety. The wide detection range and precision offer significant advancements over existing technologies.

Some embodiments may include the sensor being able to detect shapes and proximity to objects and/or entities, making the sensor valuable for security and identification purposes. This may function similarly to radar, providing accurate data on the presence and movements of individuals. This may be particularly useful for access control systems, personal identification, and monitoring of sensitive areas, ensuring that only authorized individuals gain access. Gesture and mid-air control may be another prominent application of the projected dielectric sensor. By recognizing and interpreting hand movements, the sensor may enable intuitive and interactive control of various devices and environments. This may be used in smart home systems for managing lighting, climate control, and security. In industrial settings, gesture and mid-air control may streamline operations and improve efficiency by allowing workers to control machinery and equipment without physical contact. This may reduce the risk of contamination and wear on physical interfaces.

Some embodiments may allow the sensor's data to be integrated into human machine interface and machine learning systems to enhance interactive and adaptive functionalities. By analyzing gestures and movements, machine learning algorithms may provide personalized responses and improve the overall user experience. For example, in a smart home, the system may learn the user's preferences and habits, adjusting settings automatically for optimal comfort and efficiency. Some embodiments of the sensor can perform shape detection and proximity sensing. This capability may help applications requiring precise spatial awareness. In automotive safety systems, shape detection may help identify and classify objects around the vehicle, enhancing obstacle detection and avoidance capabilities. In health monitoring, proximity sensing may track the distance and movements of patients, providing valuable data for health assessments and early detection of potential issues. This integration with AI may significantly enhance automation and user satisfaction.

Some embodiments may incorporate the sensor into environments for social interaction, enhancing communication and interaction in public and private spaces. For instance, the sensor may be used in interactive displays and installations, responding to the presence and movements of people to provide dynamic and engaging experiences. This may be applied in museums, exhibitions, and retail environments to attract and engage visitors. By detecting gestures and movements, the sensor may create responsive environments that react to the presence of individuals. In social settings, such as events or public spaces, the sensor may facilitate interactions between people and technology, making it easier to navigate information kiosks, interactive art installations, or smart public amenities. This technology may be used to transform user engagement in various public and private domains.

Some embodiments include the sensor's ability to monitor vital signs and detect changes in physical activity, which may provide continuous and non-invasive patient monitoring. This may be particularly beneficial for elderly care and chronic disease management, where real-time data may help in timely interventions and improving patient outcomes. The sensor may also be embedded in medical devices such as compression instruments to monitor and maintain consistent pressure, important for emergency situations like controlling bleeding. This capability may ensure critical health parameters are continuously monitored without invasive procedures.

Some embodiments include the sensor's capabilities to improve the precision and efficiency of various tasks in industrial automation. For example, in assembly lines, the sensor may detect the position and orientation of components, ensuring accurate assembly and reducing errors. The sensor may also be used to identify defects and inconsistencies in products, maintaining high standards of production. Some embodiments of the sensor can be integrated into flexible and wearable materials, such as smart fabrics and medical wearables. This may allow for continuous monitoring of physical activity, health metrics, and environmental conditions, providing valuable insights and data for users and healthcare providers. Wearable sensors may be used in fitness tracking, remote health monitoring, and even in military applications for monitoring soldiers' health and performance. This versatility may make the sensor a valuable tool in diverse industrial settings.

Some embodiments of the sensor may enhance interactive and adaptive functionalities by integrating into human machine interface and machine learning systems. The ability to detect and analyze gestures may make the sensor ideal for controlling mobility within a vehicle, wheelchair, or other assistive device used for movement, providing a seamless user experience. The sensor's application may extend to exterior vehicle bumpers, offering proximity detection. This embodiment may or may not include the use of one or more conductive meshes. This aspect may broaden the scope of the sensor's utility, making the sensor a valuable addition to various technological domains.

Some embodiments of the projected dielectric sensor may facilitate social interaction and gesture and mid-air control, particularly in automotive, wheelchair, or other assistive device used for movement settings. For example, drivers and passengers may interact with the vehicle's interior controls or manage the vehicle's mobility through simple gestures. The sensor's capabilities may also include shape detection and proximity detection, making the sensor suitable for a wide range of applications from vehicle safety systems to interactive entertainment.

Some embodiments may include a flexible conductive apparatus which may be utilized in applications such as vehicle, wheelchair, or other assistive device used for movement monitoring systems, gesture and mid-air control interfaces, and advanced human machine interface and machine learning frameworks. Each application may benefit from the sensor's ability to detect and respond to environmental changes, providing real-time data acquisition and interaction. The flexibility and scalability of the conductive apparatus may ensure its adaptability to various industrial and commercial uses, enhancing overall functionality and user experience.

Some embodiments include a first conductive path equipped with a power drive, which may supply the necessary electrical current for the sensor's operation. This power drive may ensure that the sensor remains active and capable of detecting changes in its environment. On the other hand, the second conductive path may include a collector, which gathers the electrical signals generated by the sensor. The interaction between the power drive and the collector may enable the sensor to accurately detect and measure various physical phenomena.

In some examples, the collector can be used to collect signals without requiring the power drive at the source. The signals are reactive to a foreign object or foreign matter at the dielectric without the power drive.

In an example, there is also a resistor between the send/receive pin which creates static resistance for capacitive sensing with delay in buildup of electrical properties, resulting in a continuous signal that changes from LOW to HIGH with conductive interference.

In an example, antennas can be created with extended path of signal resistance from extension of resistor, thereby measuring any impedance from the surrounding environment.

In an example, the textile patterns creates a variable form factor of an extended path of signal resistance from extension of resistor (acting as a collector conductive mesh), thereby allowing dynamic signal measurements without the power drive mesh.

In an example embodiment, the conductive paths are arranged on the same X-plane (e.g., side-by-side, X1, X2). This configuration may allow the sensor to offer improved detection capabilities and a wider range of applications. By having the conductive paths on the same plane, the sensor may more effectively detect objects that are off-axis to the dielectric gap, such as conductors, vehicles, humans, and baby seats.

Some embodiments of the sensor's ability to detect shapes and proximity may make the sensor invaluable in biometric applications. The sensor may function similarly to radar systems, providing accurate and reliable data about the presence and movements of individuals. This capability may be particularly useful in security and identification systems, where detection is important.

Some embodiments include the sensor's application extending to gesture and mid-air control, enabling intuitive and interactive control of devices and environments. For example, within a vehicle, the sensor may facilitate gesture control for interior settings and manage the vehicle's mobility. This may enhance the user experience by providing a seamless and intuitive interface for controlling various functions.

Some embodiments of gesture and mid-air control interfaces enabled by the projected dielectric sensor may significantly enhance protection and safety in various contexts. In smart home systems, these interfaces may detect and respond to gestures, providing an additional layer of security. For instance, a simple gesture may be used to lock doors, activate alarm systems, or call for emergency assistance. The sensor may also detect unauthorized movements or unusual activity around the property, alerting homeowners to potential threats. By integrating with existing security systems, the sensor may help in preventing break-ins and ensuring the safety of the occupants.

Some embodiments of gesture and mid-air control interfaces may contribute to safer driving experiences in automotive applications. Drivers may use hand gestures to control in-vehicle systems like adjusting the temperature, navigating the infotainment system, or answering calls without taking their eyes off the road. This may reduce distractions and help maintain focus on driving. Furthermore, the sensor may detect and respond to driver fatigue or inattentiveness by monitoring gestures and movements, prompting alerts or even taking corrective actions like slowing down the vehicle. Such features may enhance driver awareness and reduce the risk of accidents.

Some embodiments of gesture and mid-air control interfaces powered by the projected dielectric sensor may prevent work accidents and improve overall workplace safety in industrial settings. By predicting and recognizing the motions of workers, the sensor may identify potentially dangerous situations before they occur. For example, if a worker is about to step into a hazardous area or make a risky movement, the system may issue warnings or activate safety protocols to prevent injuries. This predictive capability may be important in environments with heavy machinery or hazardous materials, where quick response times may prevent serious accidents.

Some embodiments of the sensor's gesture and mid-air control capabilities may ensure patient safety and improve care quality in healthcare settings. For example, in a hospital setting, medical staff may use gestures to control medical equipment or call for assistance, minimizing the need for physical contact and reducing the spread of infections. The sensor may also monitor patient movements, detecting signs of distress or abnormal activity, and alerting caregivers to intervene promptly. This real-time monitoring may help in preventing falls and ensuring that patients receive timely care.

Some embodiments may enhance safety in public spaces through the sensor's ability to facilitate social interaction via gesture control. For example, interactive displays and installations that respond to gestures may guide individuals during emergencies, providing clear instructions and safe pathways. In large venues like airports or stadiums, the sensor may manage crowd control by detecting and responding to the movement patterns of people, preventing overcrowding and ensuring orderly evacuation if needed. This application of gesture and mid-air control may help in managing large crowds efficiently and safely.

Some embodiments may include wearable devices equipped with the projected dielectric sensor for personal safety, offering discreet protection. Individuals may use gestures to send distress signals or activate safety features on their wearable devices, such as GPS tracking or emergency calls. This may be particularly useful in situations where speaking or using a phone might not be safe. The sensor's ability to detect and interpret subtle gestures may ensure that users can access safety features quickly and unobtrusively, enhancing their sense of security.

Some embodiments of gesture and mid-air control interfaces enabled by the projected dielectric sensor may offer significant benefits in terms of protection and safety across various applications. From enhancing home security and improving vehicle safety to preventing workplace accidents and ensuring patient care, the sensor's capabilities may provide robust solutions for modern safety challenges. By integrating these advanced gesture control features, the sensor may contribute to a safer and more secure environment for individuals and communities.

Some embodiments of the projected dielectric sensor may be integrated into human machine interface and machine learning systems to enhance their interactive and adaptive functionalities. By analyzing gestures and other detected data, machine learning algorithms may provide more personalized and efficient responses, improving the overall functionality of the system.

Some embodiments of the sensor can allows the sensor to be used in exterior vehicle bumpers, offering proximity detection without the need for conductive mesh. Some embodiments may still include a conductive mesh integrated into the system. This feature may broaden the scope of the sensor's utility, making the sensor a versatile tool in various technological domains. The sensor may detect objects and obstacles around the vehicle, enhancing safety and navigation. Some embodiments may detect object inside the vehicle as well such as baby seats and other critical objects within the vehicle, providing real-time alerts to drivers and enhancing overall safety of passengers.

Some embodiments include the flexibility and scalability of the projected dielectric sensor, making the sensor suitable for a wide range of industrial and commercial applications. The sensor may be adaptable to various environments and requirements, providing robust and reliable performance. The sensor's ability to detect and respond to environmental changes may make the sensor a valuable addition to any system requiring real-time data acquisition and interaction.

Some embodiments of the projected dielectric sensor may position the conductive paths on the same X-plane, which is a significant departure from the conventional capacitive sensors that typically have their conductive paths arranged on a Y-plane. In traditional capacitive sensors, the conductive paths are placed in a stacked configuration (e.g., top and bottom, Y1, X1), which may limit the sensor's detection range and sensitivity, particularly in applications requiring detection of off-axis objects.

Some other embodiments may arrange the conductive paths side-by-side on the same X-plane (e.g., X1, X2). This configuration may enhance the sensor's ability to detect objects and changes in its environment with greater accuracy and reliability. By placing the conductive paths on the same plane, the sensor may effectively detect objects that are not directly aligned with the dielectric gap, such as conductors, vehicles, humans, and baby seats. This side-by-side arrangement may allow for a broader detection range and improved sensitivity, making the sensor highly versatile for various applications.

Some embodiments may provide several advantages over the traditional Y-plane (transverse stack) setup. Firstly, the sensor may reduce the overall thickness of the sensor, making the sensor more suitable for applications where space is a constraint. Secondly, the sensor may enhance the sensor's ability to detect off-axis objects, which may be particularly beneficial in applications such as automotive safety, where detecting the presence of passengers or other objects is important.

The side-by-side conductive paths may improve the sensor's robustness and durability. The simplified structure may minimize the potential points of failure and reduce the complexity of the manufacturing process. This may result in a more reliable sensor that can withstand various environmental conditions and maintain consistent performance.

Some embodiments of the system may open new possibilities for gesture and mid-air control and interactive applications. By detecting the position and movement of objects with high precision, the sensor may be used to create intuitive control interfaces for vehicles, smart homes, and industrial automation. For example, drivers and passengers may use gestures to control interior settings or vehicle functions, enhancing the user experience and providing a safer, hands-free interaction method.

The X-plane configuration may facilitate more accurate shape detection and proximity sensing, similar to radar systems. This capability may be valuable in a wide range of applications, from security and surveillance to health monitoring and interactive entertainment. The sensor may detect and map the shape of objects, monitor their proximity, and provide real-time data for various purposes.

In traditional capacitive sensors, the dielectric gap may be minimized to enhance the sensitivity and responsiveness of the sensor. However, this often limits the sensor's ability to detect objects that are not near the sensing elements. Some embodiments of the projected dielectric sensor may address this limitation by incorporating a larger dielectric gap, which allows the sensor to detect objects and changes in the environment over a broader range. The sensor would still be possible to operate a smaller dielectric gap.

The larger dielectric gap may act as an open circuit in the sensor's resting state, meaning that there is no current flow between the first and second conductive paths when no external force or object is present. This design may ensure that the sensor remains inactive and conserves energy until it is necessary to detect and measure an external stimulus. When an object or force is introduced, the dielectric gap may change, allowing the sensor to become active and generate a corresponding electrical signal.

One of the key benefits of the larger dielectric gap may be its ability to detect objects that are off-axis to the gap itself. This capability may be particularly useful in applications where it is important to sense objects that are not directly aligned with the sensor's conductive paths. This may enhance the sensor's versatility and applicability in real-world scenarios. Some embodiments of the dielectric gap may be adjusted dynamically to alter the sensor's sensitivity and detection range. This can be achieved using variable materials or mechanisms that control the distance between the conductive paths. Such embodiments may allow for real-time customization of the sensor's performance based on specific application needs. The space between the two conductive paths may be customized to fit certain purposes. Some embodiments may also include a way to increase or decrease the gap on the sensor without taking the sensor apart.

Some embodiments may include a multi-layer structure where the dielectric gap comprises multiple layers of varying dielectric materials, formed of matter such as air, liquid, or solid. This can further enhance the sensor's ability to detect a wide range of objects and environmental changes, providing greater flexibility and precision in various applications.

Some embodiments may incorporate environmental compensation features to automatically adjust the dielectric gap to account for changes in temperature, humidity, and other environmental factors. This may ensure consistent performance and reliability of the sensor across different conditions.

The larger dielectric gap may also improve the robustness and durability of the sensor. Traditional capacitive sensors with smaller gaps are often more susceptible to wear and tear, as well as environmental factors such as dust, moisture, and temperature fluctuations. The increased size of the dielectric gap in the projected dielectric sensor may reduce these vulnerabilities, resulting in a more reliable and long-lasting sensor.

The unique design of some embodiments of the dielectric gap may facilitate advanced functionalities such as shape detection and proximity sensing. By leveraging the larger gap, the sensor may accurately measure the distance and orientation of objects. This may make the sensor ideal for applications that require precise spatial awareness, such as gesture and mid-air control interfaces, security systems, and health monitoring devices.

Some embodiments of the projected dielectric sensor may include integration with advanced signal processing algorithms that enhance the sensor's ability to differentiate between various types of objects and movements. For instance, in vehicle safety systems, the sensor can be programmed to recognize specific gestures or motions that indicate potential hazards or emergencies. The sensor may also be programmed to detect certain materials such as cloth, metal, wood, skin, etc. This may help to determine the type of object/entity being detected by the sensor.

Some embodiments of the projected dielectric sensor may be embedded within flexible materials, such as wearable fabrics or medical devices. This integration may allow for continuous monitoring of vital signs or physical activity, providing real-time feedback and alerts based on detected changes. Some embodiments may include a sensor embedded in a medical device for monitoring one or more vital signs such as heart rate, blood pressure, respiratory rate, body temperature, oxygen saturation (SpO2), electrocardiogram (ECG) signals, blood glucose levels, heart rate variability (HRV), end-tidal CO2 (ETCO2), respiratory effort, airflow, cardiac output, blood volume, hematocrit levels, skin conductance (e.g., galvanic skin response), intracranial pressure (ICP), arterial stiffness, or pulse wave velocity (PWV).

Some embodiments of the sensor may be capable of detecting conductors or other vehicles that are adjacent or approaching from different angles. This off-axis detection may be used for advanced driver-assistance systems (ADAS) and autonomous vehicles, where understanding the vehicle's surroundings from multiple perspectives is essential for safe navigation and collision avoidance.

Some embodiments of the sensor may detect human presence and movements for applications in smart homes and buildings. By identifying individuals even when they are not directly in the sensor's line of sight, the system may provide more accurate and responsive control of lighting, climate, and security systems, enhancing both comfort and energy efficiency. Some systems may combine this sensor with audio or voice activated commands. Some embodiments may include the use of audio listening devices to further understand the object/entity or command in addition to the gesture or social interaction. Some embodiments may include the use of AI/ML methods to detect facial expressions and/or body language to execute commands. The software may include executable actions based on these gestures and commands.

In the context of wearable technology and health monitoring, some embodiments of the projected dielectric sensor may monitor vital signs and physical activities even if the sensor is not perfectly aligned with the target area. This flexibility may allow for continuous and non-invasive monitoring of patients, providing valuable data for health assessments and early detection of potential issues. This may also allow patients to wear the sensor on different parts of their body and still get the benefits of the sensing technology. For example, the sensor may detect which part of the body the sensor is sensing and proceed with healthcare analysis based on that part of the patient.

In gesture and mid-air control interfaces, some embodiments of the sensor may recognize hand movements and gestures that are performed off-axis and/or mid-air. This may enable more intuitive and natural interactions with devices and environments, such as controlling smart home systems, consumer electronics, or industrial machinery through simple gestures.

The off-axis detection capability may also extend to industrial automation and robotics, where precise detection of objects and their positions is necessary for tasks such as assembly, packaging, and quality control. Some embodiments of the sensor may ensure that these tasks are performed accurately and efficiently, even when objects are not perfectly aligned with the sensing elements.

Some embodiments of the projected dielectric sensor may be used to detect and interpret gestures for maneuvering vehicles in tight spaces, parking, and navigating complex environments. This application may enhance the safety and convenience of vehicle operation, especially in urban areas and for autonomous vehicles. This may help with autonomous vehicles, self-driving vehicles, and self-parking vehicles. This may also be used to alert the user that they are about to hit another object with their vehicle using one or more alerts. These alerts may include visual indicators on the vehicle's display, audible warnings, and haptic feedback through the steering wheel or seat. The system may also integrate with the vehicle's autonomous control to take corrective action, such as braking or steering adjustments, to prevent collisions.

Some embodiments of the sensor may be integrated into flexible and wearable materials, such as smart fabrics and medical wearables. This may allow for continuous monitoring of physical activity, health metrics, and environmental conditions. This data may be sold to third-parties and/or healthcare providers. Wearable sensors may be used in fitness tracking, remote health monitoring, and even in military applications for monitoring soldiers' health and performance.

Some embodiments may include the sensor's ability to detect shapes and proximity, making the sensor valuable for security and identification purposes. This may be particularly useful for access control systems, personal identification, and monitoring of sensitive areas, ensuring that only authorized individuals gain access. Gesture and mid-air control may be another prominent application of the projected dielectric sensor. By recognizing and interpreting hand movements, the sensor may enable intuitive and interactive control of various devices and environments. This may be used in smart home systems for managing lighting, climate control, and security. In industrial settings, gesture and mid-air control may streamline operations and improve efficiency by allowing workers to control machinery and equipment without physical contact. This may reduce the risk of contamination and wear on physical interfaces. This may also increase worker safety by reducing the amount of time that workers must be in direct contact with heavy and/or dangerous machinery.

Some embodiments of the sensor's gesture and mid-air control capabilities may ensure patient safety and improve care quality in healthcare settings. For example, in a hospital setting, medical staff may use gestures to control medical equipment or call for assistance, minimizing the need for physical contact and reducing the spread of infections. The sensor may also monitor patient movements, detecting signs of distress or abnormal activity, and alerting caregivers to intervene promptly. This real-time monitoring may help in preventing falls and ensuring that patients receive timely care. The system may also monitor the health of a patient and alert caregivers about certain conditions of a patent.

Some embodiments may enhance safety in public spaces through the sensor's ability to facilitate social interaction via gesture and mid-air control. For example, interactive displays and installations that respond to gestures may guide individuals during emergencies, providing clear instructions and safe pathways. In large venues like airports or stadiums, the sensor may manage crowd control by detecting and responding to the movement patterns of people, preventing overcrowding and ensuring orderly evacuation if needed. This application of gesture and mid-air control may help in managing large crowds efficiently and safely. Alerts may activate based on the location of high numbers of individuals, alerting others to avoid certain areas or pathways because they are overpopulated at the time.

Some embodiments may include wearable devices equipped with the projected dielectric sensor for personal safety, offering discreet protection. Individuals may use gestures to send distress signals or activate safety features on their wearable devices, such as GPS tracking or emergency calls. This may be particularly useful in situations where speaking or using a phone might not be safe, such as in a situation where an individual may be getting robbed or stalked. The sensor's ability to detect and interpret subtle gestures may ensure that users can access safety features quickly and unobtrusively, enhancing their sense of security.

Some embodiments of gesture and mid-air control interfaces enabled by the projected dielectric sensor may offer significant benefits in terms of protection and safety across various applications. From enhancing home security and improving vehicle safety to preventing workplace accidents and ensuring patient care, the sensor's capabilities may provide robust solutions for modern safety challenges. By integrating these advanced gesture and mid-air control features, the sensor may contribute to a safer and more secure environment for individuals and communities.

Some embodiments of the projected dielectric sensor may be integrated into human machine interface and machine learning systems to enhance their interactive and adaptive functionalities. By analyzing gestures and other detected data, machine learning algorithms may provide more personalized and efficient responses, improving the overall functionality of the system.

Figure 17:
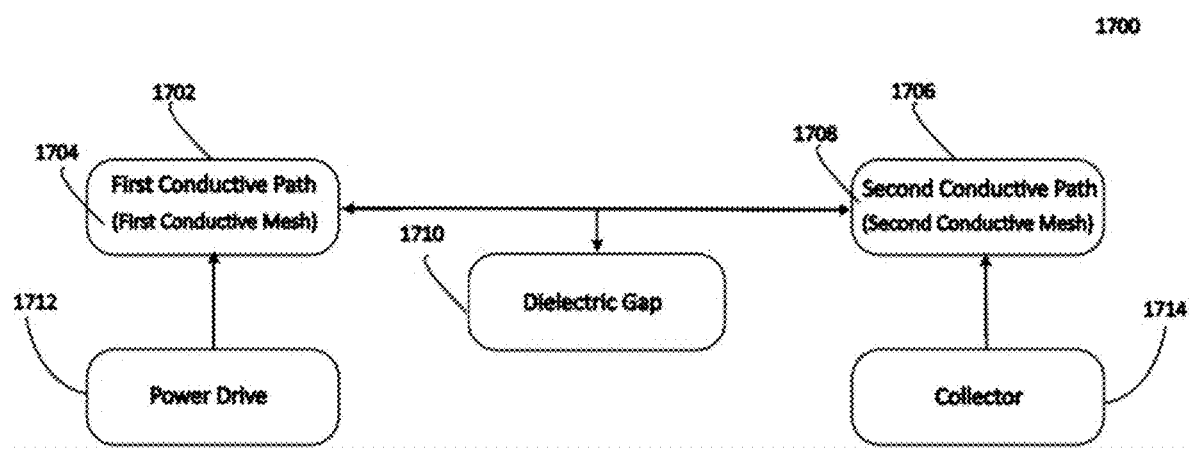
FIG. 17 shows a dielectric sensor system for dynamic capacitance sensing, including a first conductive path and a second conductive path separated by a dielectric gap, with a power drive and a collector at each end.

FIG. 17 shows a dielectric sensor (1700) system for dynamic capacitance sensing, which includes a first conductive path (1702) with a first conductive mesh (1704) and a second conductive path (1706) with a second conductive mesh (1708) separated by a dielectric gap (1710). The system also features a power drive (1712) at one end of the first conductive path (1702) and a collector (1714) at the end of the second conductive path (1706).

In some embodiments, the first conductive path (1702) and second conductive path (1706) consist of conductive mesh materials. These conductive paths are responsible for transmitting and collecting the electrical signal. The dielectric gap (1710) serves to create a capacitive effect between the two paths, allowing the system to detect variations in proximity, pressure, or other environmental factors. The dielectric gap may consist of air, glass, fabric, or other insulating material. The use of insulating material prevents electrical conduction between the two conductive elements, allowing them to maintain their electric field and capacitance properties.

The power drive (1712) supplies the necessary energy to the system to initiate the capacitance sensing process. Once the system is activated, the first conductive path (1702) interacts with objects in proximity to alter the electrical field across the dielectric gap (1710). The altered electrical signal is then transmitted along the second conductive path (1706) to the collector (1714), where the data is processed for further interpretation.

In some embodiments, the first conductive mesh (1704) or second conductive mesh (1708) can vary in size to accommodate different sensing ranges or sensitivities, and the dielectric gap (1710) can also vary in size to accommodate different sensing ranges or sensitivities. By adjusting the gap between the first conductive path (1702) and second conductive path (1706), the system can detect a wide range of conditions, from the presence of conductive materials to changes in the surrounding environment.

In some embodiments, the system may be designed to function without additional components, such as resistors or capacitors, as the dielectric gap (1710) and conductive meshes (1704 and 1708) inherently create the necessary capacitance.

In some embodiments, a dynamic capacitance sensor system may reduce the need for multiple electronic components and post-processing algorithms that are commonly used in capacitance sensing applications such as for data cleaning, filtering, and classification before further analysis can be conducted for machine/deep learning and other artificial intelligence models. By employing dynamic electrical coupling between at least two conductors with a dielectric gap, the system may identify conductive and living objects while optimizing power consumption and latency utilizing pre-edge filtering classification without post-processing analysis. Some embodiments utilize a larger dielectric gap to detect a broader range of interactions, including proximity, vibration, and pressure differential, etc. In some embodiments, the sensor may remain inactive until the sensor detects an object of interest, reducing overall power usage and enhancing the system's efficiency.

Some embodiments may include capacitive sensors that operate beyond the traditional binary output, such as high or low, on or off, etc. by using a dynamic signal output to interpret more than two states. This capability may allow for the detection of multiple states or conditions, providing a more nuanced sensing approach or range of motion of an object that does not depend on post-processing or complex computational models. In some cases, this approach can replace traditional methods that require multiple sensors, machine learning models, or software filtering to achieve similar results.

Some embodiments may use the dynamic capacitance sensor for in-cabin monitoring in vehicles, where the sensor may distinguish between living beings and non-living objects. For example, the system can determine the presence of a human occupant versus a metal object based on the electrical properties of the detected material. This distinction can be used for automotive safety applications, such as the correct deployment of airbags, child presence detection, or other occupant protection systems.

Some embodiments may use the dynamic capacitance sensor for human versus metal differentiation, where it would be distinguishable of human conductivity as a result of active bodily fluids that move throughout the body thereby producing dynamic signals between first and second conductive meshes (1704 and 1708) that may be inconsistent with conductivity, pulse-width, frequency, amplitude, phase, or any other modulation techniques that would otherwise create a conductive disruption to activate the dynamic capacitance sensor, whereas metal objects will create still signals between first and second conductive meshes (1704 and 1708), that are differentiable when activating such dynamic capacitance sensors.

In some embodiments, the dynamic capacitance sensor may function without requiring additional electronic components, such as resistors or capacitors typically used to maintain baseline signal consistency. The sensor may leverage the natural conductive properties of the objects being detected, such as human bodies or metal objects, to act as natural resistors or capacitors, thereby activating a sensing signal. This can reduce the overall cost and complexity of the sensor system, as well as minimize the environmental impact associated with the production and disposal of additional electronic components.

In some embodiments, the sensitivity of the sensor system may be adjustable based on the physical configuration of the conductors, including the gap size between them and their overall dimensions. This flexibility allows for a broad range of applications, from detecting minute physiological signals in healthcare settings to identifying larger objects in industrial automation. Adjustments in software, such as changes in detection time functions, can further refine the system's responsiveness and accuracy.

Some embodiments may include dynamic signals that provide a higher density of output information directly from the sensor level. This approach can reduce potential error rates that are common with binary outputs due to the limited on-off state interpretation. The dynamic signals can include a combination of pulse-width, frequency, and amplitude, offering more accurate sensing capabilities.

In some embodiments, modulation techniques may be used to differentiate various types of sensing data. These embodiments may include the use of low dynamic signals for proximity detection, while a combination of low amplitude and high frequency might indicate vibration of an object. Pressure changes can be represented by high amplitude variations, and in some embodiments, breathing rates can be monitored through specific amplitude patterns.

In some embodiments, the sensor system may be used in industrial automation to monitor the quality of conductive materials or items moving through a production line. For example, two conductors can be placed on either side of a conveyor belt to measure signal consistency as items pass through. Any change in the signal can indicate a variation in the conductive properties of the item, helping to identify defects or inconsistencies of products in real-time.

In some embodiments, the sensor system can also be used for health monitoring applications, such as detecting the presence of a human versus an inanimate object on the floor, in a bed, or chair, or other furnishings. The system can interpret dynamic signals to determine vital signs like heart rate or breathing patterns, distinguishing between a living being and a static object based on differences in electrical conductivity and movement.

Some embodiments may include a method for creating gesture signature patterns that can be used to activate a vehicle engine or perform other functions, thereby preventing theft or unauthorized use. Like how seat positions are programmed for individual users, gesture patterns can be personalized and stored for different occupants, enhancing vehicle security and usability.

Some embodiments may employ semiconductor logic-gate-based circuits, where a decoupling capacitor can function as both a sensor and a logic gate. For example, two electrodes may remain in a neutral state until electrical interference is detected. Depending on which electrode shows greater influence, the sensor would output a corresponding signal, enabling various response applications based on differential sensing.

In some embodiments, the detector comprises a dielectric material positioned between two conductive meshes, with a dielectric gap of at least 10 cm. This configuration enhances the sensor's ability to detect both contact and non-contact proximity values over extended distances, distinguishing the sensor from conventional sensor designs. In some embodiments, the dielectric material is non-vacuum and may include various types of matter such as air, fabric, or other suitable dielectric substances that support field coupling for proximity detection.

The dielectric material may be interweaved or doped with conductive elements providing a medium that allows the detector to function effectively across larger distances, such as those spanning more than 10 cm. This characteristic is used for detecting changes in capacitance or conductivity, which enables the sensor to detect proximity (field coupling), contact, and/or pressure (conductivity) values. The use of a dielectric material between the two conductive meshes ensures optimal sensor performance by maintaining the necessary dielectric properties while allowing for flexibility in different applications.

A larger dielectric gap length is advantageous for applications requiring higher detection ranges, such as in vehicle systems for detecting occupancy, proximity, or external objects. The dielectric gap length contributes to the overall sensitivity and range of the sensor, allowing the sensor to capture a wider array of environmental changes, including the presence of nearby objects or changes in pressure. In examples, the dielectric gap is at least 10 cm, 20 cm, 50 cm, 1 m, 2 m, 3 m, 4 m, or 5 m.

In some embodiments, the choice of dielectric material plays a significant role in enhancing the sensor's detection capabilities. For example, air may provide lower resistance to field coupling, whereas a fabric dielectric may offer a combination of flexibility and moderate resistance, allowing for specific tuning of the sensor's sensitivity and response characteristics. This flexibility in the selection of dielectric materials allows for the sensor to be customized to meet the specific needs of different applications, whether for in-vehicle systems, external monitoring, or gesture recognition.

The detector is designed as a projected/longitudinal/latitudinal sensor, featuring a power drive at one end and a collector at the other, with a dielectric material running along its length. This dielectric material encompasses conductive elements, such as a conductive mesh, to enhance the sensor's capabilities. The configuration allows the detector to cover larger distances (at least 10 cm) enabling the sensor to detect short-range proximity values from various conductors, including parts of the human body, objects, or other vehicles, without direct contact. By deploying multiple detectors in parallel, the system can further enhance its detection capabilities, gathering more comprehensive data over larger areas.

The sensor can attach to any conductor, thereby extending its conductivity range and enhancing its detection capacity. For example, in a vehicle setting, the detector can be attached to the metal frame of a car seat or the frame or the chassis of the car itself. This configuration may enable the seat frame to function as a large-area detector, significantly increasing the sensor's sensitivity and the area the sensor can monitor. The ability to attach to existing conductive structures allows for versatile applications and integration into various environments without requiring substantial modifications.

In some embodiments, the flexibility of the detector is further enhanced by the use of conductive materials such as conductive fabrics within the dielectric. This flexibility makes the sensor suitable for various applications where the sensor needs to conform to different shapes and surfaces. For example, in automotive settings, the detector may be integrated into flexible surfaces, such as car seat cushions, seat covers, or seat belts, without compromising its performance.

In some embodiments, the sensor may determine whether a baby seat is occupied along with the direction of forward or rearward facing, allowing the vehicle to activate appropriate safety measures, such as the addition of airbags with variable force levels or full suppression to prevent harm to smaller occupants or a child in a childseat. Additionally, the detector may be used for gesture and mid-air control, allowing passengers or drivers to interact with vehicle systems through simple hand movements, enhancing safety and convenience by minimizing the need for physical controls.

Figure 19:
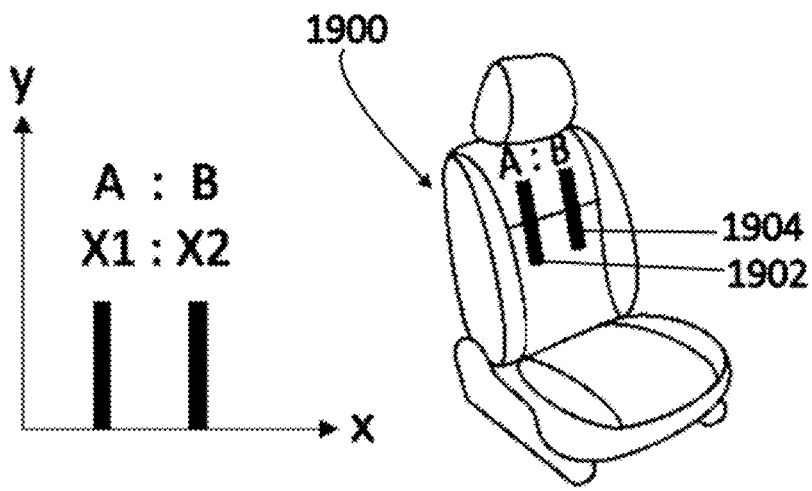
FIG. 19 shows a seat-based capacitive sensor system designed to detect the presence of a passenger in a vehicle seat by measuring changes in capacitance caused by a human body.

FIG. 19 shows a seat-based capacitive sensor system (1900) designed to detect the presence of a passenger in a vehicle seat. The figure includes two conductive paths, labeled as sensor/conductor A (X1) (1902) and sensor/conductor B (X2) (1904). These are used to sense a passenger's proximity by detecting capacitance changes caused by the interference of conductive materials such as the human body. In some embodiments, the seat frame holds the sensor elements in position, allowing the capacitive field generated between points A and B to monitor occupant presence and movement across the X and Y axes.

In some embodiments, the system uses these two conductive paths to triangulate and differentiate the occupant's location by measuring the signal strength between points X1 and X2 (A and B). The system is designed to distinguish between multiple occupant states, including, but not limited to, leaning left, leaning right, or sitting in a neutral position, based on how the capacitance changes between the conductive paths. This allows for enhanced detection and safety mechanisms, such as determining where an airbag should deploy.

Figure 20:
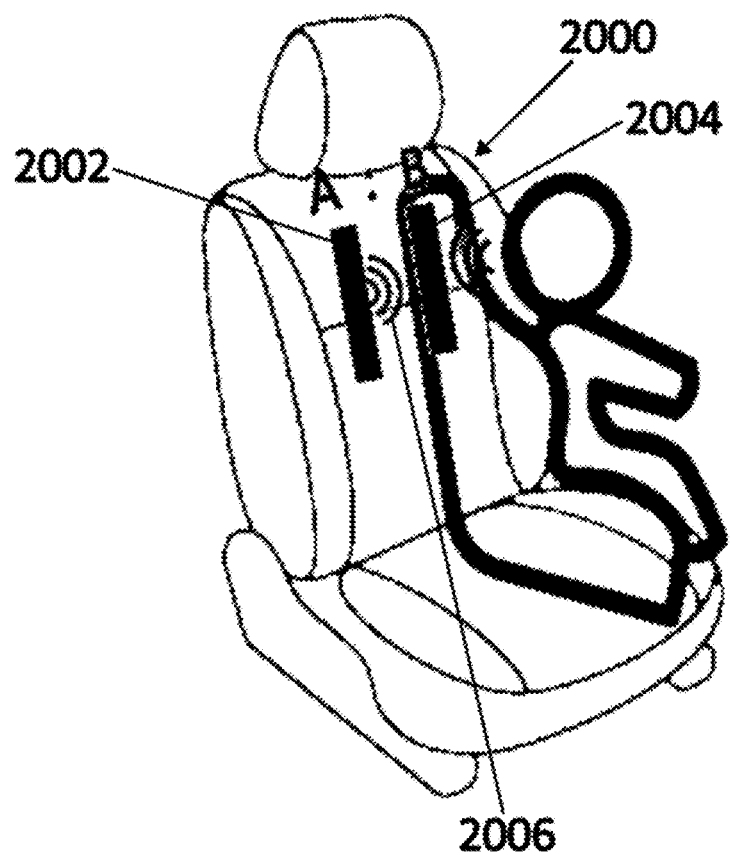
FIG. 20 shows a seat-based capacitive sensor system designed to detect the presence and orientation of a child in a child safety seat, using signals from conductive paths to monitor seating and orientation.

FIG. 20 illustrates a detailed application of a seat-based capacitive sensor system (2000) with a child occupant. In some embodiments, the conductive paths A (2002) and B (2004) are positioned to detect the presence and the orientation of a child in a child safety seat. The system measures signals (2006) for the capacitance disruption caused by the child's body, specifically in relation to conductive surfaces such as seat belts or harness systems. By detecting these changes in capacitance, the system can determine a child's presence, if they are left behind in a parked vehicle, and if they are facing forward or rearward based on the movements detected physically or by way of natural bodily fluid flow, signal strength of capacitance disruption, or other methods comprising of a dynamic signal.

In some embodiments, the sensor system is also capable of detecting whether a child is securely seated or if there is an absence of movement that can indicate a potential safety hazard or problem with the occupant. This system may increase child safety in vehicles, as improper seating or an unbuckled child can trigger alarms or other safety measures to alert the driver.

Beyond the vehicle interior, the detector can be employed externally for applications such as collision detection, precipitation sensing, and security/theft prevention. Its ability to detect proximity values and changes in environmental conditions without direct contact allows for the use of the system in a variety of locations. For example, the sensor can monitor the presence of other vehicles or obstacles, detect raindrops or snowflakes to automatically activate windshield wipers, or sense unauthorized movements around the vehicle to trigger security alarms.

The detector's high sensitivity also makes the sensor useful for detecting physiological signals of a living being. The sensor can measure changes in capacitance between its conductive elements, which may correspond to conductive properties in the blood. This feature may also enable the detector to monitor various physiological signals, such as heart rate or respiration, by detecting small changes in the body's conductive properties from one side of the sensor to the other. This capability is particularly valuable in health monitoring applications, providing a method of non-invasive and continuous monitoring of a patient.

The detector's ability to detect field coupling variations based on human posture allows the sensor to be used for gesture detection. By analyzing changes in capacitance or conductivity across different areas of the sensor, the system may determine directional force or movement. For example, if greater detection occurs in one coupling area compared to another, the sensor can interpret the movement direction and velocity of the object, enabling applications such as gesture-based control interfaces in vehicles, wheelchairs, other assistive and mobility devices, or smart environments.

In some embodiments, the sensor's proximity and contact data may be communicated to the vehicle's electronic control unit (ECU) or other communication devices, such as a passenger's mobile device. This communication enables various functions, such as activating the correct deployment strength of an airbag, issuing a seatbelt warning, alerting for child occupancy, or detecting the directional orientation of a child seat (e.g., forward or rearward facing). The ability to relay real-time data to the vehicle's control systems without post-processing and approximation models often used by machine intelligence decision-making, ensures a more responsive and adaptive safety environment, improving overall vehicle safety and user experience.

Figure 18A:
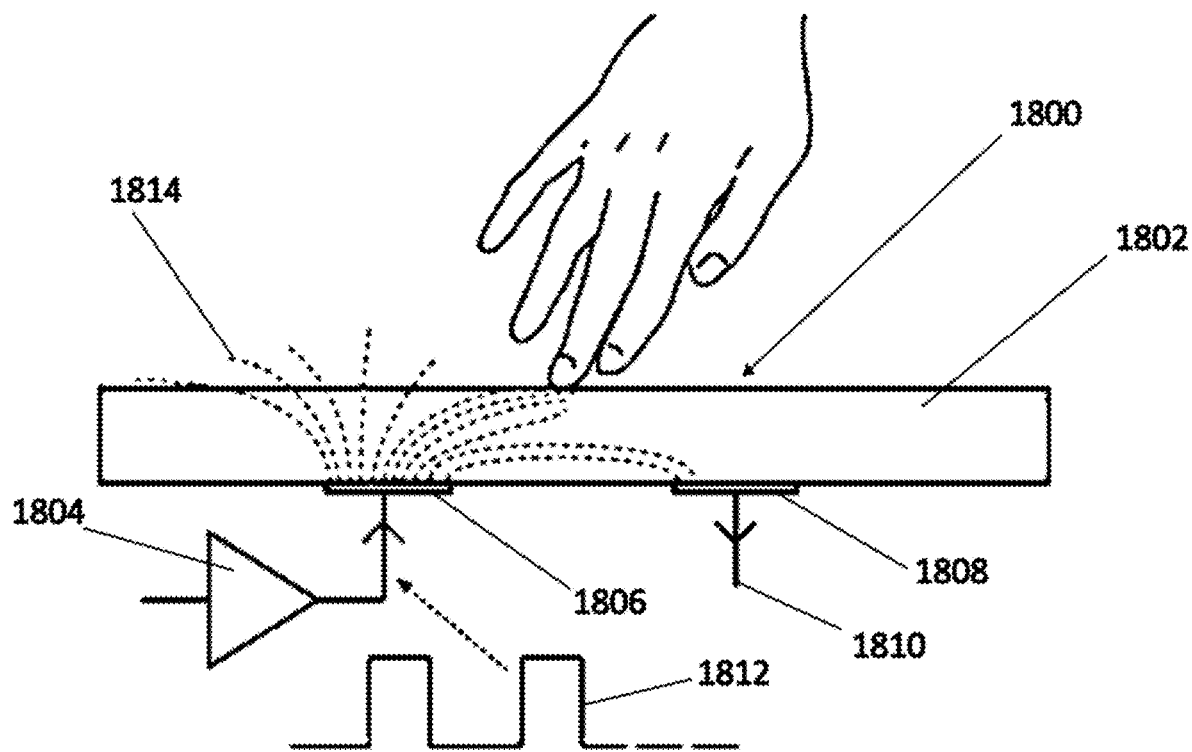
FIG. 18A shows a projected capacitive touchscreen with a dielectric front panel separating a user's touch from internal electrodes, using drive pulses to energize the circuit and detect touch interactions.

FIG. 18A shows a projected capacitive touchscreen (1800) with various components facilitating capacitance-based touch detection. In some embodiments, the dielectric (1802) is formed of matter e.g., material or air, and separates a user's touch from the internal electrodes. The drive buffer (1804) sends signals to the drive electrode (1806), which initiates the sensing process. A receive electrode (1808) collects the signal output, creating a collected charge (1810). This collected charge (1810) results from field coupling (1814) between the drive and receive electrodes, influenced by the proximity of a user's touch. Drive pulses (1812) are used to energize the circuit and detect the touch interaction.

Figure 18B:
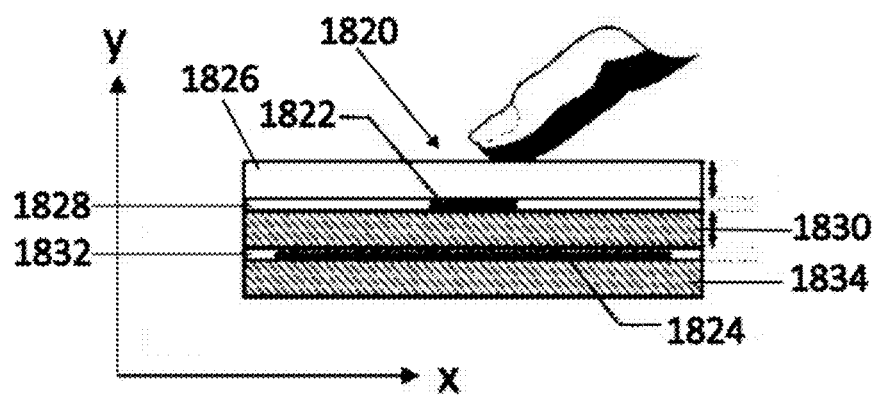
FIG. 18B shows a cross-sectional view of a touchscreen sensor with various layers including conductors, adhesive layers, and substrate layers, which contribute to the structural integrity and function of the capacitive sensing system.

FIG. 18B shows a cross-sectional view of a touchscreen sensor (1820), emphasizing how various layers contribute to touch detection. In some embodiments, the first layer conductor (1822) interacts with a second layer conductor (1824) to create the capacitive sensing field. The panel (1826) covers the sensor system to protect the internal components. The system also includes a first adhesive layer (1828) which binds to a first substrate layer (1830), and a second adhesive layer (1832) which binds to a second substrate layer (1834). These adhesive layers (1828 and 1832), along with the substrate layers (1830 and 1834), ensure that the touchscreen sensor remains structurally sound while detecting a touch. Some embodiments may not include the use of these structural layers in the system.

Figure 21:
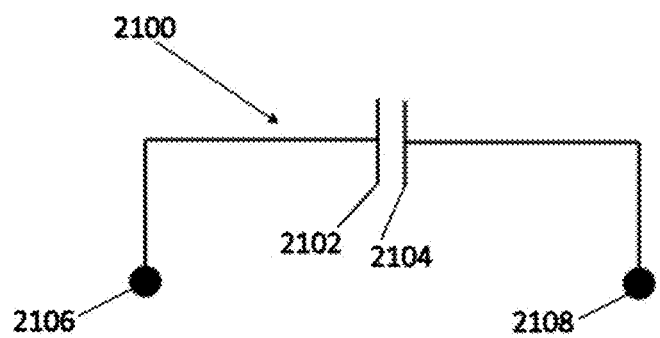
FIG. 21 shows a basic circuit for a dynamic capacitance sensor system with a first capacitor plate and a second capacitor plate separated by a dielectric gap to form the sensing mechanism.

FIG. 21 shows a schematic of a basic circuit for a dynamic capacitance sensor system (2100). In some embodiments, the system includes a first capacitor plate (2102) and a second capacitor plate (2104) separated by a dielectric gap. The dielectric material between the two conductors forms the basis of the capacitance sensing mechanism. In some embodiments, the circuit is configured to send a signal via a send PIN (2106) and receive a signal through a receive PIN (2108). The spacing between the capacitor plates and their interaction with the environment allows for signal detection based on changes in capacitance when a conductor or object interferes with the system. In some embodiments, this configuration may form a capacitive sensor where changes in capacitance are detected as variations in the signal. When the dielectric environment changes, such as when a conductive object enters the capacitive field, the circuit recognizes this disturbance and sends a feedback signal that can be processed further.

In some embodiments, the dielectric gap between the first and second conductors creates a baseline capacitance level, and any disruption in this capacitance (such as the presence of a human or conductive object) may causes a change in the signal. This change in capacitance is then detected and responsive to identify specific environmental or user interactions, depending on the application of the sensor system.

Some embodiments include methods of capacitive sensing that reduce the dependencies on post-processing by allowing for the identification of signals beyond the typical binary outputs. This approach enables detection of more than a single coordinate. By minimizing the number of components, materials, and layers required for such sensing, the system can offer a simpler and more efficient alternative to traditional capacitive sensors, which generally require a top and bottom layer to function properly.

In some embodiments, the capacitive touch sensor may operate by eliminating the Y2 layer, typically used in mutual capacitance systems. Instead of relying on three conductors, including both X and Y coordinates, the system may utilize only the X-plane, comprising X1 and X2 conductive paths. This method allows for the identification of at least two unique coordinates while operating solely on the X plane, thereby simplifying the sensor design. This approach enables a capacitive sensor to function effectively as a seat sensor to determine proper seating position on the Y plane for example leaning left or right, or in other similar applications, whereas the current standard Y plane of top and bottom capacitor plates is limited to detection of presence or absence of a conductive object.

Some embodiments describe a sensor design that uses simplified capacitive touch algorithms to reduce material costs, mitigate production integration and installation errors, and improve detection reliability. By leveraging single-plane detection techniques, these embodiments ensure that at least two unique coordinates can be identified in real-time, which is especially useful in contexts where space constraints or material efficiency are important, such as in vehicle seat sensors or other constrained environments.

Some embodiments use general capacitive circuitry that creates a buildup of temporary electrical energy storage between two plates in close proximity. This arrangement generates a potential difference or utilizes electrical field coupling to detect changes in the surrounding environment. In such configurations, sensors measure disruptions in the potential difference, which can be caused by various external factors, including the presence of conductive materials or objects within the field.

In some embodiments, the capacitive sensor system typically consists of a pair of capacitor plates connected to a send pin and a receive pin. The send pin transmits an electrical signal to one plate, while the receive pin detects any changes in the potential difference caused by interactions between the two plates. When an object enters the capacitive field, the object causes a disturbance in the electrical field, leading to a change in capacitance that is measured by the sensor system.

Some configurations employ capacitive sensing to detect alterations in resistance or disruptions in the electrical field between the capacitor plates. By monitoring the changes in the potential difference, the system can determine the presence or absence of objects, and in some embodiments, even identify their size, shape, or proximity. This detection method is particularly useful in applications where non-contact sensing is required, allowing the sensor to function effectively without direct physical contact with the object.

Other embodiments may utilize the principles of field coupling, where the electric field created between the plates is influenced by nearby conductive objects. The system then measures the variation in field strength or capacitance to infer information about the object's properties or location. This capability allows the sensor to be used in a wide range of applications, such as proximity detection, gesture and mid-air recognition, or environmental monitoring, where accurate detection of conductive materials or objects is important.

In some embodiments, the use of capacitor plates for sensing may involve adjusting the distance or dielectric material between the plates to achieve different levels of sensitivity and detection range. By optimizing these parameters, the sensor can be tuned to specific applications, enhancing its versatility and performance in various environments.

Some embodiments may utilize a wider gap to generally create an open circuit. In these configurations, an external conductive interference, such as a human body, a metal object, or any item with conductive properties, closes the gap, thereby creating a closed circuit through conductive interference. This method allows the system to operate with fewer components, lower power dependencies, and reducing external electrical signal noise interference that is commonly associated with capacitance and radar sensing technologies.

Some embodiments provide benefits in terms of optimal power consumption by only activating the system when there is an intended item to monitor. For example, in automotive applications, the system is designed to monitor occupancy detection, specifically to distinguish between objects such as a baby seat and a human, ensuring that an airbag system is correctly activated.

In some embodiments, the sensitivity of the system can be adjusted based on the size of the conductors or the spacing between them. Adjusting these parameters allows the resistance to change, or the time it takes for a disruption from the power drive to the collector in response to interference from a conductor, which also serves as the dielectric layer in conventional capacitive sensors. This adjustability may help in enhancing the performance and reliability of the sensor system in diverse applications.

Some embodiments demonstrate the use of two conductors (A and B) where a signal is sent from conductor A and received at conductor B. For example, in seating detection applications, different seating positions of an occupant, such as leaning left or right, result in varying signal readings. If a person is leaning left, signal A1 will have a lower reading than signal B1. Conversely, if the person is leaning right, signal A3 will show a lower reading than signal B3. In a neutral seating position, signals A2 and B2 will have similar readings, allowing the system to determine the posture or position of the occupant accurately.

Figure 22:
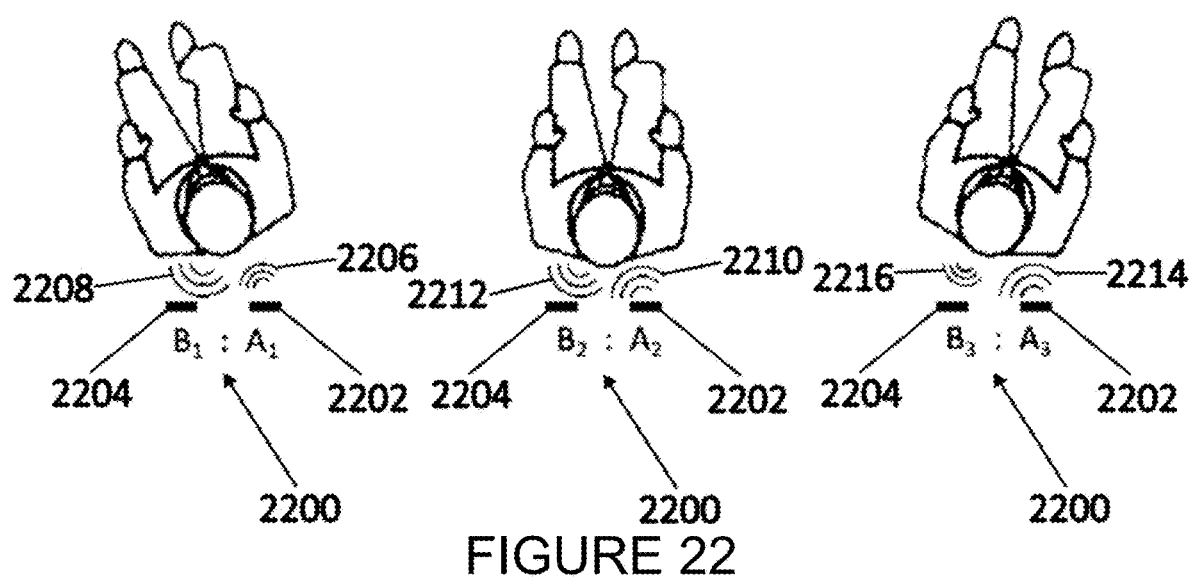
FIG. 22 shows a dynamic occupant detection system within a vehicle using two conductors to detect seating positions or movements of passengers by analyzing the signal between the conductors.

FIG. 22 depicts a dynamic occupant detection system (2200) within a vehicle. The system includes a first Sensor/Conductor A (2202) and a second Sensor/Conductor B (2204) to form a capacitive sensor. This system allows the detection of different seating positions or movements of occupants within the vehicle by analyzing the signal strength between these conductors.

FIG. 22 shows three distinct scenarios. In the first scenario, the occupant is seated more towards Conductor B (leaning left). The capacitive field is more disturbed near Conductor B, resulting in a stronger signal B1 (2208) relative to signal A1 (2206). This indicates that the occupant is leaning towards Conductor B, potentially providing input to systems such as seat adjustment or safety measures like airbag deployment.

The second scenario shows the occupant in a neutral seating position. Both signal B2 (2212) and signal A2 (2210) have equal strength, indicating that the occupant is centrally positioned between Conductors A and B. This balanced capacitive field reflects the occupant's neutral posture, which can be used for standard vehicle operations such as monitoring normal seat occupancy without any adjustment needed.

In the third scenario, the occupant leans more towards Conductor A (leaning right), creating a larger disturbance in the capacitive field near Conductor A. As a result, signal A3 (2214) is stronger than signal B3 (2216), indicating the occupant's proximity to Conductor A. This shift in seating position can trigger various vehicle systems, such as altering seatbelt tension or preparing airbag deployment adjustments to optimize safety based on the occupant's position.

This capacitive sensing setup allows the system to detect and interpret different occupant postures and seating positions without direct physical contact, relying on the variations in the capacitive field between the two conductors. By comparing the relative strengths of the signals (e.g., B1 vs. A1, B2 vs. A2, B3 vs. A3), the system can determine whether the occupant is leaning left, right, or sitting neutrally. This can provide valuable information for vehicle safety systems, such as adjusting airbag deployment zones, adjusting seat position, or even alerting the driver if a passenger is not seated correctly. Some embodiments may include detecting how far an occupant is leaning based on the strength of the signal at each respective conductor.

In some embodiments, the placement of conductors in a vehicle seat can be optimized based on the orientation and type of occupant, such as a child in a child seat. For example, when a child seat is rearward-facing, conductors may be positioned on the upper part of the backrest of the vehicle seat. In this configuration, there would be no signal reading if the child is positioned too far from the conductors, ensuring the system does not mistakenly interpret the presence of a child or other object when they are not close enough to interact with the sensor.

Some embodiments accommodate a forward-facing child seat or adult passengers by positioning the conductors such that a signal reading is generated when the proximity of a child or adult is detected close to the conductors. This arrangement allows the system to accurately determine the presence of an occupant, thereby enhancing the effectiveness of safety systems like airbag deployment and occupancy detection. These sensors may also detect the number of occupants in a vehicle and disclose this information to emergency responders during a vehicle collision to ensure the safety and identification of every occupant.

In automotive applications, where precise detection, passenger classification, and continuous monitoring of seat occupancy is necessary, certain embodiments may only require sensors to be placed in a limited area, such as on the seat backrest, seat pan, or anywhere on the seat itself. This focused placement reduces the need for extensive coverage with sensors, offering a simpler and potentially more reliable solution compared to designs requiring sensors on larger surface areas.

Some embodiments include a method for electrical flow detection and differentiation between objects and humans without the need for post-processing. This method may utilize any conductor as a sensing unit, with the capability to adjust the sensitivity of the sensing by modifying parameters such as conductor size, spacing between conductors, and directional facing of the conductors. These adjustments may allow the system to be tailored to various applications, enhancing its flexibility and accuracy in detecting different types of objects.

In some embodiments, rather than relying on two electrodes to create a single signal, the sensing dynamics can be differentiated based on a bidirectional increase or decrease in the signal. In an example embodiment, when a static conductor, such as metal, is near the right conductor, the signal would register greater than 0.5. If the conductor is closer to the left, the signal would register less than 0.5. When centered between the two conductors, the signal reads 0.5. This numerical evaluation may enable more precise detection and differentiation of objects based on their position relative to the conductors.

Other embodiments may provide for the detection of dynamic conductors, such as humans, with signal ranges varying between 0 and 1. The system may also identify when no conductor is present, maintaining an open circuit and registering no signal. This range of detection allows for the differentiation between objects that are static, dynamic, or absent, thereby enabling various functionalities such as occupancy detection, gesture and mid-air control, and security monitoring in different environments.

Some embodiments may utilize a method for detecting electrical flow and human positioning relative to a sensor. The system can identify when a human is leaning closer to one side, resulting in an asymmetric signal response. The proximity of the human body to one of the conductors causes a greater interference or coupling on that side, altering the signal characteristics. This capability allows for precise monitoring of human movements and positioning, which is useful in applications such as gesture and mid-air detection, seat occupancy monitoring, and adaptive control systems.

Figure 23A:
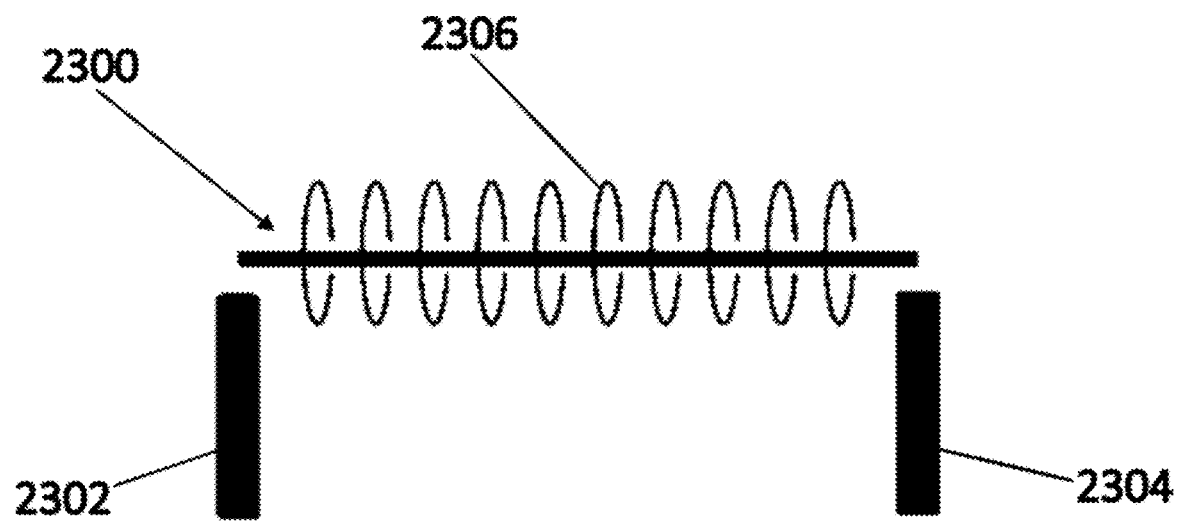
FIG. 23A shows a sensor system with two conductors separated by a dielectric medium, measuring signals traveling across the gap to detect proximity or conductive interactions.

FIG. 23A illustrates a sensor system (2300) with two conductors, Sensor/Conductor A (2302) and Sensor/Conductor B (2304), separated by a dielectric medium. The signals (2306) travel across the dielectric gap, representing the dynamic capacitive interactions that occur when an object or conductor disrupts the electrical field. In some embodiments, the positioning and size of the conductors, as well as the spacing between them, can be adjusted to detect various proximity or conductive interactions.

Figure 23B:
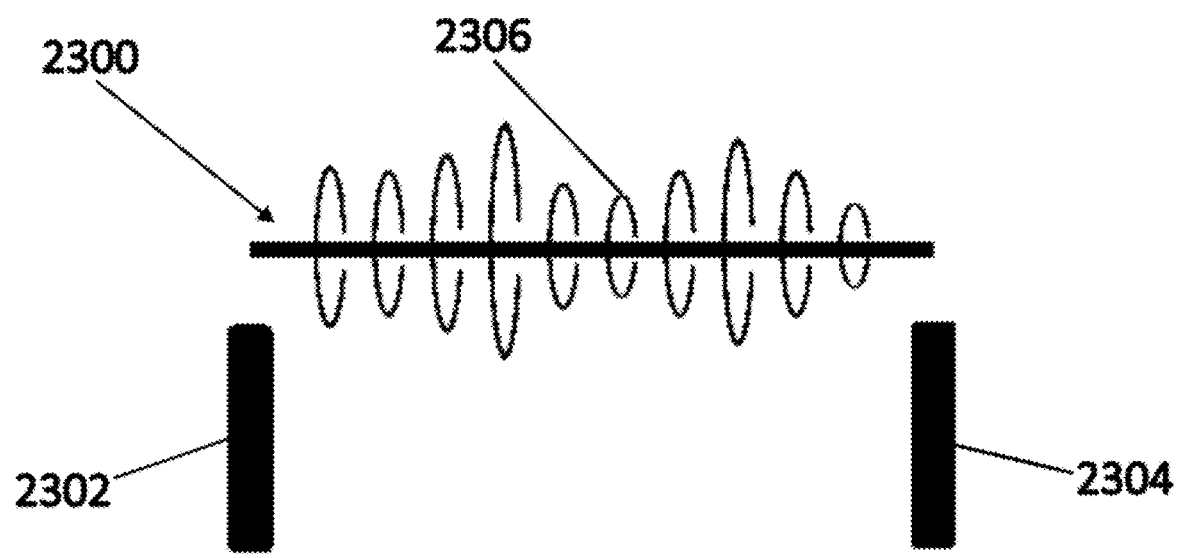
FIG. 23B shows a sensor system where variations in the dielectric gap and signal propagation are used to differentiate between conductive materials, objects, and humans.

FIG. 23B similarly shows a sensor system (2300), with Sensor/Conductor A (2302) and Sensor/Conductor B (2304), but with a variation in the dielectric gap and signal propagation (2306). In some embodiments, this variation in signal amplitude or frequency can be used to distinguish between different types of conductive interference, such as humans or metal objects, based on their conductive properties. In examples, the system can operate without requiring post-processing, offering real-time differentiation based on the signal dynamics.

Figure 23C:
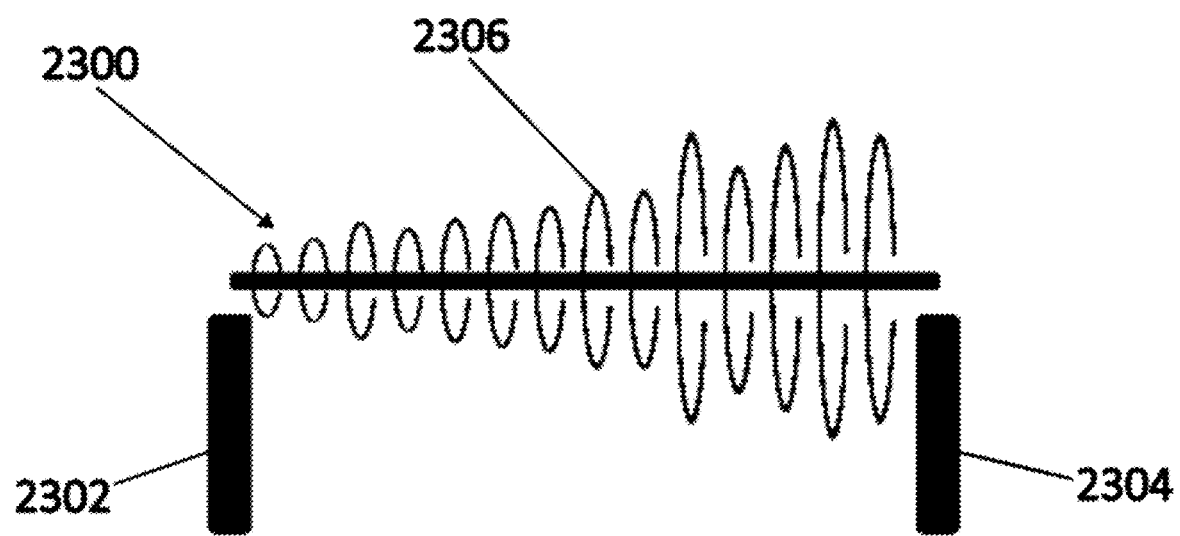
FIG. 23C shows the sensor system detecting the position of an object closer to one conductor, demonstrating how signal changes can indicate the location of an object relative to the conductors.

In FIG. 23C, the object being detected is shown to be closer to one side, indicated by the change in the electric field between the conductors. In some embodiments, the system is capable of distinguishing between a centered object and one leaning to one side, as demonstrated by the asymmetrical electric field (2306). The conductors (2302 and 2304) maintain their positions, and the system outputs different signal levels depending on where the object being detected is located. When the object is closer to conductor (2302), the electric field distribution shifts, and this signal is detected by the system. This configuration allows for more detailed object detection, such as determining the direction in which an object is leaning, based on the strength of the capacitance signal and the disturbance in the electric field.

Some embodiments allow for the detection of vital signs such as heart rate. By utilizing high sampling rates to measure the signal changes over time between two conductors, the system can capture fluctuations in conductivity related to blood flow. As blood, which contains conductive properties like iron, moves through the body, the changes in capacitance can be measured to detect heartbeats. This application enables continuous, non-invasive monitoring of physiological signals, enhancing the ability to assess health and wellness states in real time.

Some embodiments include the use of a radar-type method that utilizes vehicle structural elements (such as the pillars A, B, and C) to create a sensing grid within the vehicle. This method involves installing conductors along multiple pillars, which function similar to in-cabin radar emitters and detectors, allowing for precise detection of objects or individuals within the vehicle's interior. The pillars may be arranged to form a matrix-like network that can accurately determine the position and movement of occupants or objects by using electromagnetic wave propagation and reflection principles.

In some embodiments, the Doppler effect is employed to sense between the pillars, enhancing the system's ability to detect movement, velocity, and direction of objects or individuals within the vehicle. By detecting shifts in frequency caused by the relative motion between the source and the object, the system can interpret changes in the internal environment of the vehicle. This directional sensing method focuses the detection capabilities within the vehicle, reducing interference from external noise and other artifacts commonly associated with conventional radar systems.

Some embodiments may provide a focused sensing capability that limits the detection parameters to the internal environment of the vehicle. This concentrated approach minimizes false positives and enhances the accuracy of object detection by confining the sensing parameters to the conductors located inside the vehicle pillars. In some embodiments, the radar system may differentiate between stationary and moving objects and provide real-time data on the positioning and movement patterns of passengers.

Some embodiments further enhance the detection capabilities by implementing a series of radar-type measurements across different pillar combinations, such as A1 to A2, A1 to B1, A1 to C1, etc., creating a comprehensive detection matrix. This approach allows for simultaneous monitoring of multiple zones within the vehicle, for use in applications such as occupant safety monitoring, automatic airbag deployment adjustment, child presence detection, and gesture and mid-air control systems.

Figure 24A:
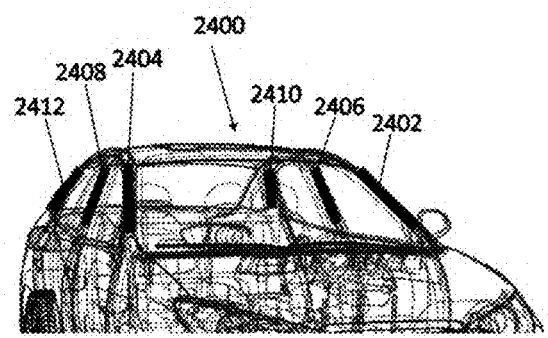
FIG. 24A shows a vehicle with multiple pillars acting as conductors in a dynamic capacitive sensor system to detect objects, people, or conductive materials inside the vehicle.

FIG. 24A illustrates a vehicle (2400) with multiple pillars acting as conductors in the dynamic capacitive sensor system. Pillars A1 (2402), A2 (2404), B1 (2406), B2 (2408), and C1 (2410), and C2 (2412) are placed within the vehicle (2400) structure. In some embodiments, these pillars act as individual conductors or sensing elements that interact with the dielectric space within the vehicle cabin to detect objects, people, or other conductive materials. Some embodiments include multiple positions that work in conjunction with the other pillars to create a multi-point detection system between each of the sensors. The system may detect disturbances between the pillars and determine the position of an object or person within the vehicle by identifying which connections between the pillars are disrupted.

Figure 24B:
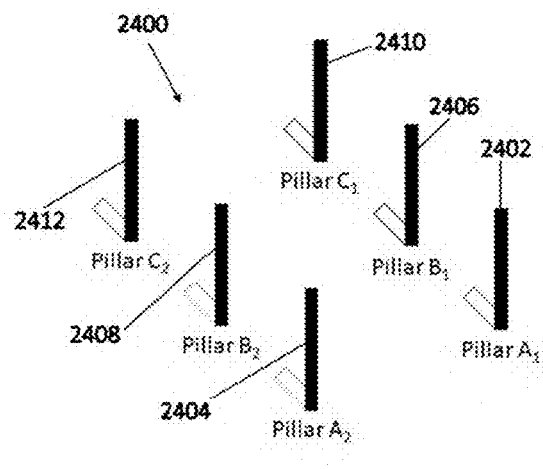
FIG. 24B shows the spatial layout of the pillars within the vehicle, aligning sensors on the pillars to provide coverage across the cabin.

FIG. 24B shows a more detailed configuration of the pillars in relation to their spatial layout. Each pillar includes a sensor that aligns with other sensors on the other pillars to cover different areas of the cabin.

In some embodiments, the pillars form a capacitive sensing network that operates on the X, Y, and Z axes, enabling the detection of objects or living beings. The arrangement of these pillars allows for effective coverage of the entire vehicle interior, increasing the accuracy of detection.

Figure 24C:
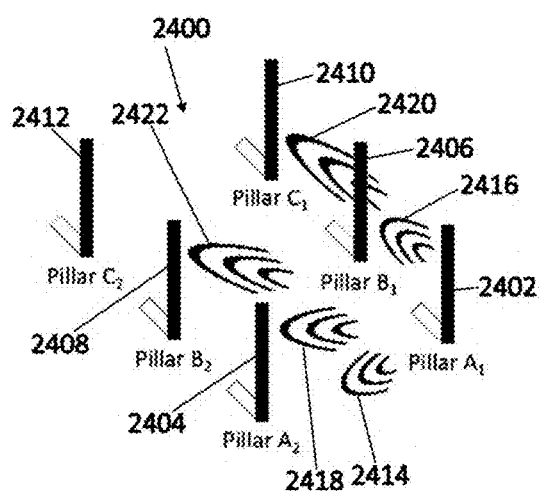
FIG. 24C shows signal propagation between the pillars to detect passengers or objects in the vehicle by measuring the disruptions between the pillars.

FIG. 24C expands on the interaction between the various pillars, illustrating signal propagation and detection points between the pillars. Pillar A1 (2402), pillar B1 (2406), and pillar C1 (2410) work in coordination with signal interactions between them. Pillar A2 (2404), pillar B2 (2408), and pillar C2 (2412) also work in coordination. For example, pillar B2 (2408) may interact with pillar A1 (2402), creating signal wave (2418) that propagate and detect the presence of conductive objects, such as passengers or items, within the vehicle. In some embodiments, these signal waves allow for real-time monitoring of the vehicle interior and can help differentiate between living beings and inanimate objects providing comprehensive coverage. Some embodiments may include more pillars added to the system (D1 and D2) to provide more coverage, any number of pillars may be installed. Some embodiments may include the use of the pillars in other scenarios such as public transportation, airports, smart homes, industrial warehouses, shopping malls, conference rooms, healthcare facilities, parking garages, stadiums/arenas, and/or factories/manufacturing plants.

Figure 24D:
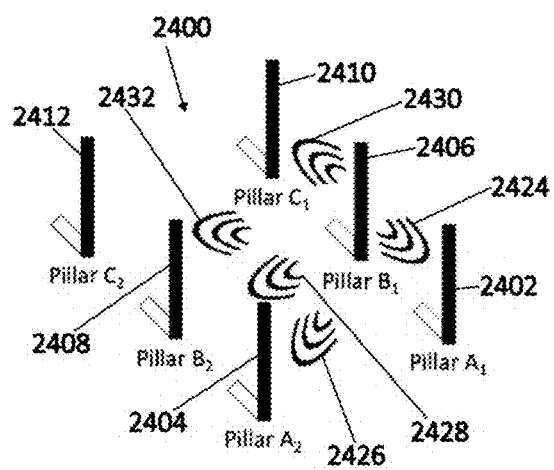
FIG. 24D shows a network of signal propagation between the pillars, detecting changes in proximity and position within the vehicle based on signal transmissions.

FIG. 24D demonstrates a complex network of signal propagation between the pillars. In this figure, pillar B1 (2406) interacts with pillar C1 (2410) and pillar A1 (2402) through signal transmissions (2430, 2424), while pillar B2 (2408), C2 (2412), and A2 (2404) interacts with pillar B1 (2406) through signals (2428, 2432, and 2426) respectively. In some embodiments, the dynamic sensing between these pillars detects changes in the proximity and presence of occupants within the vehicle. As the signals propagate through the system, it can detect when a human is leaning closer to one pillar versus another.

Some embodiments may utilize these sensor values to create a matrix of data points, which offers insight into the spatial arrangement of objects or humans within the vehicle. For example, a high sensor value, such as 1.0, indicates proximity or direct alignment between an occupant and a specific pair of pillars, while lower values (e.g., 0.4 or 0.1) suggest less proximity or alignment. This data may be used to dynamically adjust vehicle systems, such as seat belt tensioners or airbags, based on the detected presence and positioning of occupants, thereby enhancing safety measures tailored to the specific seating arrangement. The detection of objects utilizing the matrix can position each object in space based on their respective values between each pair of conductors.

Some embodiments may include a better resolution for detecting and differentiating between multiple occupants or objects in the vehicle, allowing for enhanced safety protocols and more precise monitoring of the internal environment. This approach also enhances the ability to differentiate between adult and child occupants, as well as recognizing different seating configurations, such as forward or rearward-facing child seats, and adjusting vehicle safety responses accordingly.

In some embodiments, the system uses its capability to detect variations in electrical conductivity in various industrial automation processes. For example, in a conveyor belt setup, conductors (A and B) may be positioned to create a sensing field that identifies and distinguishes between objects based on their conductive properties. The system may continuously monitor objects passing through the detection zone and determines whether the objects contain metal or other conductive materials, and the relative size and velocity of the objects. This application may be useful in sorting or filtering items by material properties in recycling facilities, quality control stations, or automated packaging lines.

The system may also be applied in environments where consistent monitoring of conductive properties is required over long production runs. For example, in electronic textile manufacturing, the system monitors the quality and consistency of conductive yarns by placing multiple conductors (A, B, C, etc.) along the loom in various configurations. This setup allows the system to detect any deviations in conductivity that may indicate flaws or inconsistencies in the yarns. As the conductive yarn moves through the detection fields, the system continuously measures its electrical properties and provides instant feedback to operators or automated controls, enabling immediate adjustments to maintain quality standards and reduce waste.

The system's directional sensing may also reduce the impact of environmental noise, which can interfere with accuracy in conventional detection systems. By focusing the sensing parameters in a specific direction, such as toward the center of the loom or along the conveyor belt, the system minimizes interference from external sources.

In some embodiments, the detection method can differentiate between different grades or types of conductive materials. For example, in a metal sorting facility, the system may identify not just the presence of metal but also its type or grade based on specific conductivity signatures. Similarly, in the textile industry, the system can differentiate between various conductive threads or fibers to ensure that only materials meeting predefined specifications continue in the production process.

In some embodiments, the integration of this system into existing automation infrastructures is possible because of the system's modular and scalable design. Sensors and conductors may be arranged and repositioned with minimal disruption to the production line, allowing adaptation to different product types or quality control requirements. This flexibility enables the technology to be used in a range of industrial contexts, from manufacturing to textile fabrication.

In an example embodiment, the raw sensor signal values are represented using two conductors configured with an outward directional face, resulting in a single signal output that can exist in one of five states. The first state is indicated by a maximum value of 1, which shows that the sensors are active. The second state occurs when the signal is above the mid-range but below the maximum, within a range of 0.6 to 1.0, which represents a proximity closer to the "send" conductor. The third state is defined by a mid-range value of 0.5, signifying a neutral position where the signal is balanced between the two conductors. The fourth state reflects a lower value, below 0.5, indicating proximity closer to the "receive" conductor. The fifth state is represented by a value of 0, which denotes a short circuit condition where no effective sensing takes place. Other embodiments may alert the user in a different range of values, the inverse values, or include more than five states. The numbers used above are for illustration purposes, any numbers/values/ranges may be used in place of the given values herein.

While some of the present embodiments are described in terms of methods, a person of ordinary skill in the art will understand that present embodiments are also directed to various apparatus such as processors, circuitry, and controllers including components for performing at least some of the aspects and features of the described methods, be it by way of hardware components, software or any combination of the two, or in any other manner, as applicable.

In the Figures, as applicable, at least some or all of the illustrated subsystems or blocks may include or be controlled by a processor, which executes instructions stored in a memory or non-transitory computer readable medium. Variations may be made to some example embodiments, which may include combinations and sub-combinations of any of the above. The various embodiments presented above are merely examples and are in no way meant to limit the scope of this disclosure. Example embodiments described herein will be apparent to persons of ordinary skill in the art having the benefit of the example embodiments, such variations being within the intended scope of the present disclosure. In particular, features from one or more of the above-described embodiments may be selected to create alternative embodiments comprised of a sub-combination of features, which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

Certain adaptations and modifications of the described embodiments can be made. Therefore, the above discussed embodiments are considered to be illustrative and not restrictive.

What is claimed is:

1. A dielectric sensor, comprising:
   a first conductive path including a first conductive mesh, the first conductive mesh including a first sheet, wherein the first conductive path terminates at the first sheet;
   a second conductive path including a second conductive mesh, the second conductive mesh including a second sheet, wherein the second conductive path terminates at the second sheet, wherein the first sheet and the second sheet are generally coplanar;
   a dielectric gap formed of matter which physically separates the first conductive path and the second conductive path, wherein the dielectric gap longitudinally separates the first sheet from the second sheet, wherein the dielectric gap is at least 10 cm between the first sheet and the second sheet;
   a power drive directly connected to the first conductive path; and
   a collector directly connected to the second conductive path.

2. The dielectric sensor of claim 1, wherein the dielectric gap does not constitute a vacuum.

3. The dielectric sensor of claim 1, wherein the dielectric gap formed of matter comprises air.

4. The dielectric sensor of claim 1, the dielectric gap formed of matter comprises fabric.

5. The dielectric sensor of claim 1, wherein the first conductive mesh and the second conductive mesh are each made of at least one of conductive fabric, conductive tape, conductive liquid, or conductive metal.

6. The dielectric sensor of claim 1, wherein the first sheet and the second sheet are separated by at least 20 centimeters, 50 centimeters, 1 meter, 2 meters, 3 meters, 4 meters, or 5 meters.

7. The dielectric sensor of claim 1, wherein the second conductive path is not connected to the power drive or any other power drive.

8. The dielectric sensor of claim 1, wherein the dielectric sensor is configured to detect a conductor or second matter that is off-axis to the dielectric gap.

9. The dielectric sensor of claim 1, wherein the dielectric gap is an open circuit of the dielectric sensor in the absence of second matter at the dielectric gap in which no signal is received by the collector.

10. The dielectric sensor of claim 1, wherein the dielectric sensor is configured to detect a vehicle or a human that is off-axis to the dielectric gap.

11. The dielectric sensor of claim 1, wherein the dielectric sensor is in at least one vehicle to detect presence and/or position of at least one occupant.

12. The dielectric sensor of claim 1, wherein the dielectric sensor is integrated into at least one exterior vehicle bumper for proximity detection.

13. The dielectric sensor of claim 1, wherein the dielectric sensor is used for shape detection in at least one biometric application.

14. The dielectric sensor of claim 1, wherein the dielectric sensor is used for proximity detection in at least one biometric application.

15. The dielectric sensor of claim 1, wherein the dielectric sensor is configured to interface with at least one gesture or mid-air control interface.

16. The dielectric sensor of claim 15, wherein the at least one gesture or mid-air control interface is configured to interact with or manage mobility of a vehicle.

17. The dielectric sensor of claim 1, wherein the dielectric sensor is integrated in a medical device configured for monitoring at least one vital sign, the vital sign being one of heart rate, blood pressure, respiratory rate, body temperature, oxygen saturation (SpO2), electrocardiogram (ECG) signals, blood glucose levels, heart rate variability (HRV), end-tidal CO2 (ETCO2), respiratory effort, airflow, cardiac output, blood volume, hematocrit levels, skin conductance, galvanic skin response, intracranial pressure (ICP), arterial stiffness, or pulse wave velocity (PWV).

18. The dielectric sensor of claim 1, wherein the dielectric sensor is integrated into at least one flexible and wearable material for continuous monitoring of at least one of physical activity, health metrics, or environmental conditions.

19. The dielectric sensor of claim 1, wherein the dielectric sensor is a projected dielectric sensor.

20. The dielectric sensor of claim 1, wherein the dielectric gap is an open circuit of the dielectric sensor when in a resting state in which no signal is received by the collector.

21. The dielectric sensor of claim 1, wherein the first sheet is configured to be attached to a first pillar of a frame of a vehicle, wherein the second sheet is configured to be attached to a second pillar of the frame of the vehicle.

22. The dielectric sensor of claim 21, wherein the first sheet is shaped to the first pillar and the second sheet is shaped to the second pillar.

23. The dielectric sensor of claim 1, wherein the dielectric sensor is integrated into a human machine interface and machine learning system.

24. The dielectric sensor of claim 1, wherein the dielectric sensor is configured to detect: 1) short circuit condition; 2) proximity to closer to the first sheet than the second sheet; 3) proximity to closer to the second sheet than the first sheet; and 4) open circuitry condition.

25. A dielectric sensor for a vehicle comprising:
a first conductive path including a first conductive mesh, the first conductive mesh including a first sheet, wherein the first conductive path terminates at the first sheet, wherein the first sheet is configured to be attached to a first pillar of a frame of the vehicle;
a second conductive path including a second conductive mesh, the second conductive mesh including a second sheet, wherein the second conductive path terminates at the second sheet, wherein the second sheet is configured to be attached to a second pillar of the frame of the vehicle;
a dielectric gap formed of matter which physically separates the first conductive path and the second conductive path,
wherein the dielectric gap longitudinally separates the first sheet from the second sheet,
wherein the first sheet and the second sheet are separated by at least 10 cm by the dielectric gap;
a power drive directly connected to the first conductive path; and
a collector directly connected to the second conductive path.

26. The dielectric sensor of claim 25, wherein the first sheet and the second sheet are generally coplanar.

27. The dielectric sensor of claim 25, wherein the first sheet and the second sheet are separated by at least 20 centimeters, 50 centimeters, 1 meter, 2 meters, 3 meters, 4 meters, or 5 meters.

28. The dielectric sensor of claim 25, wherein the first sheet is shaped to the first pillar and the second sheet is shaped to the second pillar.

* * * * *